(12) United States Patent
Jones et al.

(10) Patent No.: US 11,367,605 B2
(45) Date of Patent: Jun. 21, 2022

(54) AMBIENT IONIZATION MASS SPECTROMETRY IMAGING PLATFORM FOR DIRECT MAPPING FROM BULK TISSUE

(71) Applicant: Micromass UK Limited, Wilmslow (GB)

(72) Inventors: Emrys Jones, Manchester (GB); Steven Derek Pringle, Darwen (GB); Zoltan Takats, Cambridge (GB)

(73) Assignee: MICROMASS UK LIMITED, Wilmslow (GB)

( * ) Notice: Subject to any disclaimer, the term of this patent is extended or adjusted under 35 U.S.C. 154(b) by 67 days.

(21) Appl. No.: 15/555,818

(22) PCT Filed: Mar. 7, 2016

(86) PCT No.: PCT/GB2016/050626
§ 371 (c)(1),
(2) Date: Sep. 5, 2017

(87) PCT Pub. No.: WO2016/142696
PCT Pub. Date: Sep. 15, 2016

(65) Prior Publication Data
US 2018/0047551 A1    Feb. 15, 2018

(30) Foreign Application Priority Data

Mar. 6, 2015  (GB) ..................................... 1503863
Mar. 6, 2015  (GB) ..................................... 1503864
(Continued)

(51) Int. Cl.
*H01J 49/04*    (2006.01)
*A61B 90/13*    (2016.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
None
See application file for complete search history.

(56) References Cited

U.S. PATENT DOCUMENTS 3,479,545 A    11/1969  Wilson et al.
3,770,954 A    11/1973  Davis
(Continued)

FOREIGN PATENT DOCUMENTS

CA    2527886 A1    12/2004
CA    2876731 A1    12/2013
(Continued)

OTHER PUBLICATIONS

Trimpin, S. et al. New Ionization Method for Analysis on Atmospheric Pressure Ionization Mass Spectrometers Requiring Only Vacuum and Matrix Assistance, Analytical Chemistry, vol. 85, pp. 2005-2009 (Year: 2013).*

(Continued)

*Primary Examiner* — Xiaoyun R Xu

(57) ABSTRACT

A method of ion imaging is disclosed that includes automatically sampling a plurality of different locations on a sample using a front device which is arranged and adapted to generate aerosol, smoke or vapour from the sample. Mass spectral data and/or ion mobility data corresponding to each location is obtained and the obtained mass spectral data and/or ion mobility data is used to construct, train or improved a sample classification model.

11 Claims, 28 Drawing Sheets

(30) Foreign Application Priority Data

| | | | |
|---|---|---|---|
| Mar. 6, 2015 | (GB) | .................... | 1503867 |
| Mar. 6, 2015 | (GB) | .................... | 1503876 |
| Mar. 6, 2015 | (GB) | .................... | 1503877 |
| Mar. 6, 2015 | (GB) | .................... | 1503878 |
| Mar. 6, 2015 | (GB) | .................... | 1503879 |
| Sep. 9, 2015 | (GB) | .................... | 1516003 |
| Oct. 16, 2015 | (GB) | .................... | 1518369 |

(51) Int. Cl.

| | |
|---|---|
| *A61B 1/04* | (2006.01) |
| *A61B 1/273* | (2006.01) |
| *A61B 5/00* | (2006.01) |
| *A61B 5/01* | (2006.01) |
| *A61B 5/0507* | (2021.01) |
| *A61B 5/055* | (2006.01) |
| *A61B 6/03* | (2006.01) |
| *A61B 8/13* | (2006.01) |
| *A61B 10/00* | (2006.01) |
| *A61B 10/02* | (2006.01) |
| *A61B 17/00* | (2006.01) |
| *A61B 17/32* | (2006.01) |
| *A61B 18/00* | (2006.01) |
| *A61B 18/04* | (2006.01) |
| *A61B 18/14* | (2006.01) |
| *A61B 18/18* | (2006.01) |
| *A61B 18/20* | (2006.01) |
| *A61F 13/38* | (2006.01) |
| *C12Q 1/02* | (2006.01) |
| *C12Q 1/04* | (2006.01) |
| *C12Q 1/18* | (2006.01) |
| *C12Q 1/24* | (2006.01) |
| *G01N 1/22* | (2006.01) |
| *G01N 3/00* | (2006.01) |
| *G01N 9/00* | (2006.01) |
| *G01N 27/622* | (2021.01) |
| *G01N 27/624* | (2021.01) |
| *G01N 30/72* | (2006.01) |
| *G01N 33/487* | (2006.01) |
| *G01N 33/68* | (2006.01) |
| *G01N 33/92* | (2006.01) |
| *H01J 49/00* | (2006.01) |
| *H01J 49/02* | (2006.01) |
| *H01J 49/06* | (2006.01) |
| *H01J 49/10* | (2006.01) |
| *H01J 49/14* | (2006.01) |
| *H01J 49/16* | (2006.01) |
| *H01J 49/24* | (2006.01) |
| *H01J 49/26* | (2006.01) |
| *G16H 10/40* | (2018.01) |
| *G16H 15/00* | (2018.01) |
| *G16H 50/20* | (2018.01) |
| *G16B 20/00* | (2019.01) |
| *A61B 1/00* | (2006.01) |
| *A61B 1/31* | (2006.01) |
| *A61B 5/145* | (2006.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/0404* (2013.01); *H01J 49/044* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(56) References Cited

U.S. PATENT DOCUMENTS

| | | |
|---|---|---|
| 4,408,125 A | 10/1983 | Meuzelaar |
| H414 H | 1/1988 | Young et al. |
| 4,835,383 A | 5/1989 | Mahoney et al. |
| 4,845,367 A | 7/1989 | Kmirav et al. |
| 4,883,958 A | 11/1989 | Vestal |
| 4,935,624 A | 6/1990 | Henion et al. |
| 5,033,541 A | 7/1991 | D'Silva |
| 5,053,343 A | 10/1991 | Vora et al. |
| 5,210,412 A | 5/1993 | Levis et al. |
| 5,257,991 A | 11/1993 | Fletcher et al. |
| 5,308,977 A | 5/1994 | Oishi et al. |
| 5,374,755 A | 12/1994 | Neue et al. |
| 5,454,274 A | 10/1995 | Zhu |
| 5,509,916 A | 4/1996 | Taylor |
| 5,559,326 A | 9/1996 | Goodley et al. |
| 5,663,561 A | 9/1997 | Franzen et al. |
| 5,696,352 A | 12/1997 | Kourimsky |
| 5,800,597 A | 9/1998 | Perrotta et al. |
| 5,828,062 A | 10/1998 | Jarrell et al. |
| 5,830,214 A | 11/1998 | Flom et al. |
| 5,836,909 A | 11/1998 | Cosmescu |
| 5,969,352 A | 10/1999 | French et al. |
| 5,989,015 A | 11/1999 | Guerin et al. |
| 6,032,673 A | 3/2000 | Savage |
| 6,333,632 B1 | 12/2001 | Yang et al. |

(56) References Cited

U.S. PATENT DOCUMENTS

| | | |
|---|---|---|
| 6,348,688 B1 | 2/2002 | Vestal |
| 6,825,464 B2 | 11/2004 | De La Mora |
| 6,998,622 B1 | 2/2006 | Wang et al. |
| 7,057,168 B2 | 6/2006 | Miller et al. |
| 7,238,936 B2 | 7/2007 | Okamura et al. |
| 7,247,845 B1 | 7/2007 | Gebhardt et al. |
| 7,329,253 B2 | 2/2008 | Brounstein et al. |
| 7,335,897 B2 | 2/2008 | Takats et al. |
| 7,365,309 B2 | 4/2008 | Denny et al. |
| 7,517,348 B2 | 4/2009 | Vetter et al. |
| 7,564,028 B2 | 7/2009 | Vestal |
| 7,718,958 B2 | 5/2010 | Shiea et al. |
| 7,828,948 B1 | 11/2010 | Hatch et al. |
| 7,947,039 B2 | 5/2011 | Sartor |
| 7,960,711 B1 | 6/2011 | Sheehan et al. |
| 8,156,151 B2 | 4/2012 | Sidman |
| 8,193,487 B2 | 6/2012 | Briglin et al. |
| 8,232,520 B2 | 7/2012 | Cristoni |
| 8,253,098 B2 | 8/2012 | Hiraoka et al. |
| 8,286,260 B2 | 10/2012 | Vertes et al. |
| 8,314,382 B2 | 11/2012 | Takats |
| 8,334,504 B2 | 12/2012 | Finlay et al. |
| 8,431,409 B1 | 4/2013 | Meinhart et al. |
| 8,448,493 B2 | 5/2013 | McIntyre et al. |
| 8,481,922 B2 | 7/2013 | Musselman |
| 8,778,695 B2 | 7/2014 | Caprioli |
| 8,803,085 B2 | 8/2014 | Ouyang et al. |
| 8,834,462 B2 | 9/2014 | Johnson et al. |
| 8,970,840 B2 | 3/2015 | Kulkarni et al. |
| 8,980,577 B2 | 3/2015 | Maier |
| 9,046,448 B2 | 6/2015 | Takats |
| 9,053,914 B2 | 6/2015 | Pringle et al. |
| 9,082,603 B2 | 7/2015 | Bajic |
| 9,120,083 B2 | 9/2015 | Wyndham et al. |
| 9,255,907 B2 | 2/2016 | Heanue et al. |
| 9,281,174 B2 | 3/2016 | Takats |
| 9,287,100 B2 | 3/2016 | Szalay et al. |
| 9,709,529 B2 | 7/2017 | Takats |
| 9,731,219 B2 | 8/2017 | Wang et al. |
| 9,947,524 B2 | 4/2018 | Pringle et al. |
| 10,077,461 B2 | 9/2018 | Beaulieu et al. |
| 10,186,626 B2 | 1/2019 | Song et al. |
| 2002/0008871 A1 | 1/2002 | Poustka et al. |
| 2002/0070338 A1 | 6/2002 | Loboda |
| 2002/0076824 A1 | 6/2002 | Haglund, Jr. et al. |
| 2003/0001084 A1 | 1/2003 | Bateman et al. |
| 2003/0008404 A1 | 1/2003 | Tomita et al. |
| 2003/0015657 A1 | 1/2003 | Takada et al. |
| 2003/0042412 A1 | 3/2003 | Park |
| 2003/0080278 A1 | 5/2003 | Okada et al. |
| 2003/0119193 A1 | 6/2003 | Hess et al. |
| 2003/0135222 A1 | 7/2003 | Baska |
| 2003/0136918 A1 | 7/2003 | Hartley |
| 2003/0193023 A1 | 10/2003 | Marsh |
| 2004/0007673 A1 | 1/2004 | Coon et al. |
| 2004/0079881 A1 | 4/2004 | Fischer et al. |
| 2004/0124352 A1 | 7/2004 | Kashima et al. |
| 2004/0197899 A1 | 10/2004 | Gomez et al. |
| 2004/0217274 A1 | 11/2004 | Bai et al. |
| 2004/0235395 A1 | 11/2004 | Hashish et al. |
| 2005/0017091 A1 | 1/2005 | Olsen et al. |
| 2005/0032471 A1 | 2/2005 | Pfarr et al. |
| 2005/0061779 A1 | 3/2005 | Blumenfeld |
| 2005/0067565 A1 | 3/2005 | Takada et al. |
| 2005/0072916 A1 | 4/2005 | Park |
| 2005/0074361 A1 | 4/2005 | Tanoshima et al. |
| 2005/0077644 A1 | 4/2005 | Bryan et al. |
| 2005/0124986 A1 | 6/2005 | Brounstein et al. |
| 2005/0138861 A1 | 6/2005 | O'Connor |
| 2005/0154490 A1 | 7/2005 | Blaine et al. |
| 2005/0159765 A1 | 7/2005 | Moutafis et al. |
| 2005/0178962 A1 | 8/2005 | Guevremont et al. |
| 2005/0178975 A1 | 8/2005 | Glukhoy |
| 2005/0179366 A1 | 8/2005 | Rose et al. |
| 2005/0230611 A1 | 10/2005 | Denny et al. |
| 2005/0230634 A1 | 10/2005 | Bajic et al. |
| 2005/0230635 A1 | 10/2005 | Takats et al. |
| 2005/0258358 A1 | 11/2005 | Thakur |
| 2005/0269518 A1 | 12/2005 | Bajic et al. |
| 2005/0274885 A1 | 12/2005 | Brown et al. |
| 2006/0035570 A1 | 2/2006 | Chisum et al. |
| 2006/0054806 A1 | 3/2006 | Yamada et al. |
| 2006/0091308 A1 | 5/2006 | Boyle et al. |
| 2006/0097084 A1 | 5/2006 | Gromer et al. |
| 2006/0108539 A1 | 5/2006 | Franzen |
| 2006/0113463 A1 | 6/2006 | Rossier et al. |
| 2006/0122593 A1 | 6/2006 | Jun |
| 2006/0138321 A1 | 6/2006 | Ahem et al. |
| 2006/0145089 A1 | 7/2006 | Cristoni et al. |
| 2006/0186334 A1 | 8/2006 | Jolliffe et al. |
| 2006/0250138 A1 | 11/2006 | Sparkman et al. |
| 2006/0255264 A1 | 11/2006 | Belford |
| 2007/0023631 A1 | 2/2007 | Takats et al. |
| 2007/0023677 A1 | 2/2007 | Perkins et al. |
| 2007/0094389 A1 | 4/2007 | Nussey et al. |
| 2007/0114388 A1 | 5/2007 | Ogawa et al. |
| 2007/0114394 A1 | 5/2007 | Combs et al. |
| 2007/0114437 A1 | 5/2007 | Kovtoun |
| 2007/0176092 A1 | 8/2007 | Miller et al. |
| 2007/0176113 A1 | 8/2007 | Shiea et al. |
| 2007/0181802 A1 | 8/2007 | Yamada et al. |
| 2008/0001081 A1 | 1/2008 | Jindai et al. |
| 2008/0015278 A1 | 1/2008 | Malik et al. |
| 2008/0042056 A1 | 2/2008 | Fischer et al. |
| 2008/0067352 A1 | 3/2008 | Wang |
| 2008/0073503 A1 | 3/2008 | Wu |
| 2008/0073512 A1 | 3/2008 | Siuzdak et al. |
| 2008/0132890 A1 | 6/2008 | Woloszko et al. |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0312651 A1 | 12/2008 | Pope et al. |
| 2009/0065714 A1 | 3/2009 | Keady |
| 2009/0082637 A1 | 3/2009 | Galperin |
| 2009/0088772 A1 | 4/2009 | Blumenkranz |
| 2009/0126891 A1 | 5/2009 | Koivunen et al. |
| 2009/0159790 A1 | 6/2009 | Kostiainen et al. |
| 2009/0272893 A1 | 11/2009 | Hieftje et al. |
| 2009/0294660 A1 | 12/2009 | Whitehouse et al. |
| 2009/0302211 A1 | 12/2009 | Takats |
| 2010/0012830 A1 | 1/2010 | Cristoni |
| 2010/0072359 A1 | 3/2010 | Briglin et al. |
| 2010/0078550 A1 | 4/2010 | Wiseman et al. |
| 2010/0101304 A1 | 4/2010 | McIntyre et al. |
| 2010/0176290 A1 | 7/2010 | Vidal-de-Miguel |
| 2010/0186524 A1 | 7/2010 | Ariessohn et al. |
| 2010/0229263 A1 | 9/2010 | Vertes et al. |
| 2010/0273666 A1 | 10/2010 | Bernatchez et al. |
| 2011/0036978 A1 | 2/2011 | Franzen |
| 2011/0049352 A1 | 3/2011 | Ding et al. |
| 2011/0059554 A1 | 3/2011 | Albers et al. |
| 2011/0087308 A1 | 4/2011 | Morgan |
| 2011/0121173 A1 | 5/2011 | Koenig et al. |
| 2011/0295250 A1 | 12/2011 | Johnson et al. |
| 2012/0018628 A1 | 1/2012 | Wuijckhuijse et al. |
| 2012/0048264 A1 | 3/2012 | Finlay et al. |
| 2012/0074306 A1 | 3/2012 | Jesse et al. |
| 2012/0079894 A1 | 4/2012 | Van Berkel et al. |
| 2012/0080592 A1 | 4/2012 | Wiseman et al. |
| 2012/0085649 A1 | 4/2012 | Sano et al. |
| 2012/0119079 A1 | 5/2012 | Ouyang et al. |
| 2012/0141789 A1 | 6/2012 | Wyndham et al. |
| 2012/0149009 A1 | 6/2012 | Levis et al. |
| 2012/0156712 A1 | 6/2012 | Takats |
| 2012/0201846 A1 | 8/2012 | Rehm et al. |
| 2012/0295276 A1 | 11/2012 | Cooks et al. |
| 2012/0308555 A1 | 12/2012 | Polakiewicz et al. |
| 2013/0123919 A1 | 5/2013 | Goldstein et al. |
| 2013/0178845 A1 | 7/2013 | Smith et al. |
| 2013/0181126 A1 | 7/2013 | Jong |
| 2013/0303846 A1 | 11/2013 | Cybulski et al. |
| 2013/0306856 A1 | 11/2013 | Trimpin et al. |
| 2014/0039480 A1 | 2/2014 | Van Wyk |

(56) References Cited

U.S. PATENT DOCUMENTS

| | | |
|---|---|---|
| 2014/0151547 A1 | 6/2014 | Bajic |
| 2014/0268134 A1 | 9/2014 | O'Connor |
| 2014/0276775 A1 | 9/2014 | Funk et al. |
| 2014/0291506 A1 | 10/2014 | Tikhonski |
| 2014/0297201 A1 | 10/2014 | Knorr et al. |
| 2014/0299577 A1 | 10/2014 | Chung |
| 2014/0303449 A1 | 10/2014 | Balog |
| 2014/0326865 A1 | 11/2014 | Pringle et al. |
| 2014/0336456 A1 | 11/2014 | Demers et al. |
| 2014/0350534 A1 | 11/2014 | Kircher et al. |
| 2014/0353488 A1 | 12/2014 | Takats |
| 2014/0353489 A1 | 12/2014 | Szalay et al. |
| 2015/0021469 A1 | 1/2015 | Bajic |
| 2015/0048255 A1 | 2/2015 | Jarrell |
| 2015/0144782 A1 | 5/2015 | Fogwill et al. |
| 2015/0192590 A1 | 7/2015 | Sodeoka et al. |
| 2015/0201913 A1 | 7/2015 | Takats |
| 2015/0340215 A1 | 11/2015 | Pringle et al. |
| 2016/0002696 A1 | 1/2016 | Galiano |
| 2016/0133450 A1 | 5/2016 | Green et al. |
| 2016/0215322 A1 | 7/2016 | Goodlett et al. |
| 2016/0247668 A1 | 8/2016 | Szalay et al. |
| 2016/0341712 A1 | 11/2016 | Agar |
| 2016/0372313 A1 | 12/2016 | Brown et al. |
| 2017/0103880 A1 | 4/2017 | Syage |
| 2018/0047551 A1 | 2/2018 | Jones et al. |
| 2018/0053644 A1 | 2/2018 | Jones et al. |
| 2018/0136091 A1 | 5/2018 | Ryan et al. |
| 2018/0254177 A1 | 9/2018 | Gao et al. |
| 2018/0256239 A1 | 9/2018 | Johnson et al. |

FOREIGN PATENT DOCUMENTS

| | | |
|---|---|---|
| CA | 2882003 A1 | 2/2014 |
| CN | 1672238 A | 9/2005 |
| CN | 101073137 A | 11/2007 |
| CN | 101170043 A | 4/2008 |
| CN | 101178381 A | 5/2008 |
| CN | 101223625 A | 7/2008 |
| CN | 101288146 A | 10/2008 |
| CN | 101372502 A | 2/2009 |
| CN | 101413905 A | 4/2009 |
| CN | 101490524 A | 7/2009 |
| CN | 201266145 Y | 7/2009 |
| CN | 101657158 A | 2/2010 |
| CN | 101819179 A | 9/2010 |
| CN | 101871914 A | 10/2010 |
| CN | 102026709 A | 4/2011 |
| CN | 102121921 A | 7/2011 |
| CN | 102137618 A | 7/2011 |
| CN | 102164675 A | 8/2011 |
| CN | 102169791 A | 8/2011 |
| CN | 102264404 A | 11/2011 |
| CN | 102367424 A | 3/2012 |
| CN | 102445544 A | 5/2012 |
| CN | 102483369 A | 5/2012 |
| CN | 102768236 A | 11/2012 |
| CN | 102800553 A | 11/2012 |
| CN | 102879453 A | 1/2013 |
| CN | 102924993 A | 2/2013 |
| CN | 102928610 A | 2/2013 |
| CN | 103295873 A | 9/2013 |
| CN | 103335984 A | 10/2013 |
| CN | 103426712 A | 12/2013 |
| CN | 103456595 A | 12/2013 |
| CN | 103597574 A | 2/2014 |
| CN | 103748233 A | 4/2014 |
| CN | 103764812 A | 4/2014 |
| CN | 104062348 A | 9/2014 |
| CN | 104254772 A | 12/2014 |
| CN | 104254901 A | 12/2014 |
| CN | 104284984 A | 1/2015 |
| CN | 104582616 A | 4/2015 |
| EP | 0169469 A2 | 1/1986 |
| EP | 0437358 A2 | 7/1991 |
| EP | 1225616 A1 | 7/2002 |
| EP | 1530721 A2 | 5/2005 |
| EP | 1855306 A1 | 5/2006 |
| EP | 1730519 B1 | 7/2010 |
| EP | 3265817 A1 | 1/2018 |
| EP | 3266035 A1 | 1/2018 |
| EP | 3265818 B1 | 2/2020 |
| GB | 2420008 B | 5/2006 |
| GB | 2425178 A | 10/2006 |
| GB | 2462190 A | 2/2010 |
| GB | 2491484 A | 12/2012 |
| GB | 2491486 A | 12/2012 |
| GB | 2507298 A | 4/2014 |
| GB | 2523873 A | 9/2015 |
| JP | S63243864 A | 10/1988 |
| JP | 03001435 A | 1/1991 |
| JP | H0785834 A | 3/1995 |
| JP | H07130325 A | 5/1995 |
| JP | H10247472 A | 9/1998 |
| JP | 10302710 A | 11/1998 |
| JP | H1164283 A | 3/1999 |
| JP | 2000097913 A | 4/2000 |
| JP | 2000180413 A | 6/2000 |
| JP | 2001183345 A | 7/2001 |
| JP | 2002170518 A | 6/2002 |
| JP | 2004264043 A | 9/2004 |
| JP | 2005205181 A | 8/2005 |
| JP | 2006329710 A | 12/2006 |
| JP | 2007-51934 A | 3/2007 |
| JP | 2007170870 A | 7/2007 |
| JP | 2007218916 A | 8/2007 |
| JP | 2010169454 A | 8/2010 |
| JP | 2014515831 A | 7/2014 |
| JP | 2015503109 A | 1/2015 |
| JP | 2015504160 A | 2/2015 |
| KR | 20020013544 A | 4/2007 |
| KR | 1020100106336 A | 10/2010 |
| WO | 9734534 A1 | 9/1997 |
| WO | 0160265 A1 | 8/2001 |
| WO | 2009070555 A1 | 6/2009 |
| WO | 2010075265 A2 | 7/2010 |
| WO | 2010136887 A1 | 12/2010 |
| WO | 2011114902 A1 | 9/2011 |
| WO | 2012143737 A1 | 10/2012 |
| WO | 2012164312 A2 | 12/2012 |
| WO | 2012174437 A1 | 12/2012 |
| WO | 2013093517 A1 | 6/2013 |
| WO | 2013098642 A2 | 7/2013 |
| WO | 2013098645 A2 | 7/2013 |
| WO | 2013102670 A1 | 7/2013 |
| WO | WO 2013/098642 | * 7/2013 |
| WO | 2013/148162 | 10/2013 |
| WO | 2014/106165 A1 | 7/2014 |
| WO | 2014128629 A1 | 8/2014 |
| WO | 2014139018 A1 | 9/2014 |
| WO | 2014140601 A1 | 9/2014 |
| WO | 2014142926 A1 | 9/2014 |
| WO | 2014202828 A1 | 12/2014 |
| WO | 2015004457 A1 | 1/2015 |
| WO | 2015132579 A1 | 9/2015 |
| WO | 2016046748 A1 | 3/2016 |
| WO | 2016142674 A1 | 9/2016 |
| WO | 2016156615 A1 | 10/2016 |
| WO | 2018142091 A2 | 8/2018 |

OTHER PUBLICATIONS

Cha, S. Laser desorption/ionization mass spectrometry for direct profiling and imaging of small molecules from raw biological materials, Doctoral dissertation, Iowa State University. (Year: 2008).*

Jackson, S. N. et al. On-line laser desorption/ionization mass spectrometry of matrix-coated aerosols, Rapid Communications in Mass Spectrometry, vol. 18, pp. 2041-2045 (Year: 2004).*

Agar, Nathalie et al., "*Development of Stereotactic Mass Spectrometry for Brain Tumor Surgery*", Biosis, Neurosurgery Online, vol. 68, No. 2, (2011).

(56) References Cited

OTHER PUBLICATIONS

Ahif, Dorothy R. et al., "Correlated Mass Spectrometry Imaging and Confocal Raman Microscopy for Studies of Three-Dimensional Cell Culture Sections", Analyst, vol. 139, No. 18, pp. 4578 (2014).
Azimzadeh, Omid et al., "Formalin-Fixed Paraffin-Embedded (FFPE) Proteome Analysis Using Gel-Free and Gel-Based Proteomics", Journal of Proteome Research, vol. 9, No. 9, pp. 4710-4720 (2010).
Balgley, Brian M. et al., "Evaluation of Archival Time on Shotgun Proteomics of Formalin-Fixed and Paraffin-Embedded Tissues", Journal of Proteome Research, vol. 8, No. 2, pp. 917-925 (2009).
Balog, Julia et al., "Identification of Biological Tissues by Rapid Evaporative Ionization Mass Spectrometry", Analytical Chemistry, vol. 82, No. 17, pp. 7343-7350 (2010).
Balog, Julia et al., "Supporting Information for Identification of Biological Tissues by Rapid Evaporative Ionization Mass Spectrometry", pp. S1-S9, http://pubs.acs.org/doi/suppl/10.1021/ac101, (2013).
Balog, J. et al., "Intraoperative Tissue Identification Using Rapid Evaporative Ionization Mass Spectrometry", Science Translational Medicine, vol. 5, No. 194, pp. 194ra93 (2013).
Balog, J. et al., "Supplementary Materials: Intraoperative Tissue Identification Using Rapid Evaporative Ionization Mass Spectrometry", Science Translational Medicine, vol. 5, No. 194, pp. 194ra93 (2013).
Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B, vol. 901, pp. 41-46 (2012).
Bellet, V. et al., "Proteomic Analysis of RCL2 Paraffin-Embedded Tissues", Journal of Cellular and Molecular Medicine, vol. 12, No. 5B, pp. 2027-2036 (2008).
Bocklitz, T.W. et al., "Deeper Understanding of Biological Tissue: Quantitative Correlation of MALDI-TOF and Raman Imaging", Analytical Chemistry, vol. 85, No. 22, pp. 10829-10834 (2013).
Cole, Laura M. et al., "Mass Spectrometry Imaging for the Proteomic Study of Clinical Tissue", Proteomics-Clinical Applications, vol. 9, No. 3-4, pp. 335-341 (2015).
Crawshaw, Benjamin et al., "Gastrointestinal Surgery: Real-Time Tissue Identification During Surgery", Nature Review/Gastroenterology & Hepatology Nature, vol. 10, No. 11. pp. 624-625.
Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers in Surgery and Medicine, vol. 44, No. 5, pp. 406-412 (2012).
Davies, T.J. et al., "Volatile Products from Acetylcholine as Markers in the Rapid Urine Test Using Head-Space Gas-Liquid Chromatography B: Biomedical Sciences and Applications", Journal of Chromatography, vol. 307, pp. 11-21 (1984).
European Commission, "ISD Report Summary", http://cordis.europa.eu/result/ren/163435_e, (2016).
Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).
Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (2012).
Golf, Ottmar et al., "Rapid Evaporative Ionization Mass Spectrometry Imaging Platform for Direct Mapping from Bulk Tissue and Bacterial Growth Media", Analytical Chemistry, vol. 87, No. 5, pp. 2527-2534 (2015).
Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (2014).
Guenther, Sabine et al., "Electrospray Post-Ionization Mass Spectrometry of Electrosurgical Aerosols", Journal of the American Society for Mass Spectrometry, vol. 22, No. 11, pp. 2082-2089 (2011).
Gustafsson, Ove J.R. et al., "Proteomic Developments in the Analysis of Formalin-Fixed Tissue", Biochimica et Biophysica Acta, vol. 1854, No. 6, pp. 559-580.
Hobbs, S.K. et al., "Magnetic Resonance Image-Guided Proteomics of Human Glioblastoma Multiforme", Journal of Magnetic Resonance Imaging, vol. 18, pp. 530-536 (2003).
Hsu, Cheng-Chih et al., "Visualizing Life with Ambient Mass Spectrometry", Current Opinion in Biotechnology, vol. 31, pp. 24-34 (2015).
Jadoul, L. et al., "Matrix-Assisted Laser Desorption/Ionization Mass Spectrometry and Raman Spectroscopy: An Interesting Complementary Approach for Lipid Detection in Biological Tissues", European Journal of Lipid Science and Technology. vol. 116, No. 8, pp. 1080-1086 (2014).
Jain, M. et al., "Metabolite Profiling Identifies a Key Role for Glycine in Rapid Cancer Cell Proliferation", American Association for the Advancement of Science, vol. 336, No. 6084, pp. 1040-1044 (2012).
Jarmusch, Alan K et al., "Detection of Strep Throat Causing Bacterium Directly from Medical Swabs by Touch Spray-Mass Spectrometry", Analyst, vol. 139, No. 19, pp. 4785 (2014).
Jarmusch, Alan K. et al., "Supplemental Information Detection of Strep Throat Causing Bacterium Directly from Medical Swabs by Touch Spray-Mass Spectrometry", http://www.rsc.org/suppdata/an/c4/c4an00959(2016).
Lazova, Rossitza et al., "Imaging Mass Spectrometry—A New and Promising Method to Differentiate Spitz Nevi From Spitzoid Malignant Melanomas", American Journal of Dermatopathology, vol. 34, No. 1, pp. 82-90 (2012).
Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, pp. 15 (2013).
Lieuwe, D.J. et al., "Volatile Metabolites of Pathogens: A Systematic Review", PLoS Pathogens, vol. 9, No. 5, pp. 1003311.
Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (1996).
McCullough, Bryan J. et al., "On-Line Reaction Monitoring by Extractive Electrospray Ionisation", Rapid Communications in Mass Spectrometry, vol. 25, No. 10, pp. 1445-1451 (2011).
Murray, Patrick R, "What Is New in Clinical Microbiology-Microbial Identification by MALDI-TOF Mass Spectrometry", Journal of Molecular Diagnostics, vol. 14, No. 5, pp. 419-423 (2012).
Nicholson, Jeremy K. et al., "Metabolic Phenotyping in Clinical and Surgical Environments", Nature, vol. 491, No. 7424 pp. 384-392 (2012).
Pirro, Valentina et al., "Direct Drug Analysis from Oral Fluid Using Medical Swab Touch Spray Mass Spectrometry", Analytica Chimica Acta, vol. 861, pp. 47-54.
Plata, N. et al., "Aerosols Sampling Using a New Cryogenic Instrument", Journal of Aerosol Science, vol. 37, No. 12, pp. 1871-1875 (2006).
Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).
Schafer, Karl-Christian et al., "In Vivo, In Situ Tissue Analysis Using Rapid Evaporative Ionization Mass Spectrometry", Angewandte Chemie International, vol. 48, No. 44, pp. 8240-8242 (2009).
Shane, Ellis R. et al., "Surface Analysis of Lipids by Mass Spectrometry: More Than Just Imaging", Progress in Lipid Research Pergamon Press, vol. 52, No. 4, pp. 329-353.
Shoemaker, Robert H., "The NCI60 Human Tumour Cell Line Anticancer Drug Screen", (2013).
Strittmatter, N. et al., "Anaylsis of Intact Bacteria Using Rapid Evaporative Ionisation Mass Spectrometry", Chemical Communications, vol. 49, No. 55, pp. 6188 (2013).
Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (2014).

(56) References Cited

OTHER PUBLICATIONS

Strittmatter, N. et al., "*Taxon-Specific Markers for the Qualitative and Quantitative Detection of Bacteria in Human Samples*", http://www.msacl.org/2015_US_Long Abstract.
Tait, Emma et al., "*Identification of Volatile Organic Compounds Produced by Bacteria Using HS-SPME-GC-MS*", Journal of Chromatographic Sci, pp. 1-11.
Uribe, D.O. et al., "*Piezoelectric Self-Sensing System for Tactile Intraoperative Brain Tumor Delineation in Neurosurgery*", Proceedings of the 31$^{st}$ Annual International Conference of the IEEE Engineering in Medicine and Biology Society: Engineering the Future of BioMedicine, pp. 737-740 (2009).
Vander Wilp, W. et al., "*Lead in Micro-Samples of Whole Blood by Rhenium-Cup in-Torch Vaporization-Inductively Coupled Plasma-Atomic Emission Spectrometry (ITV-ICP-AES)*", Fresenius' Journal of Analytical Chemistry, vol. 368, No. 7, pp. 734-736 (2000).
Vircks, Kyle E. et al., "*Rapid Screening of Synthetic Cathinones as Trace Residues and in Authentic Seizures Using a Portable Mass Spectrometer Equipped with Desorption Electrospray Ionization*", Rapid Communications in Mass Spectrometry, vol. 26, No. 23, pp. 2665-2672 (2012).
Summons to Attend Oral Proceedings Pursuant to Rule 115(1) EPC of EP Application No. 12726643.5, dated Apr. 20, 2018, 7 pages.
Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.
Chen, H., et al: "Neutral desorption sampling coupled to extractive electrospray ionization mass spectrometry or rapid differentiation of biosamples by metabolomic fingerprinting", Journal of Mass Spectromety, vol. 42, No. 9, Sep. 1, 2007 pp. 1123-1135.
Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998 (Aug. 1, 1998), pp. 1017-1019.
Moot, A. et al: "Composition of Volatile Organic Compouds in Diathermy Plume as Detected by Selected Ion Flow Tube Mass Spectrometry", ANZ Journal of Surgery, vol. 77, No. 1-2, (Jan. 2007) pp. 20-23.
Strittmatter, N.: "Home—Miss Nicole Strittmatter" Retrieved from the Internet URL: http://www.imperial.ac.uk/people/n.strittmatter12 [retrieved on May 19, 2016] the whole document.
Wehofsky, et al ("Automated deconvolution and deisotoping of electrospray mass spectra" J. Mass Spectrom. 2002; 37: pp. 223 - 229).
Al Sahaf et al., "Chemical Composition of Smoke Produced by High-Frequency Electrosurgery", Irish Journal of Medical Science, vol. 176, No. 3, pp. 229-232, 2007.
Barrett et al., "Surgical Smoke: A Review of the Literature", Surgical Endoscopy, vol. 17, No. 6, pp. 979-987, 2003.
Down, "A DESI-Rable Ionization Revolutionizes Mass Spectrometry", Base Peak, 2005.
International Search Report and Written Opinion for International Application. No. PCT/IB2012/003009, dated Aug. 14, 2013, 17 pages
PCT International Search Report and Written Opinion for International Appln. No. PCT/IB2010/001261, dated Sep. 21, 2010, 5 pages.
PCT International Search Report and Written Opinion for International Appln. No. PCT/IB2012/002995, dated Sep. 10, 2013, 3 pages.
Diao et al., "Electrostatic-Spray Ionization Mass Spectrometry", Analytical Chemistry, vol. 84, No. 17, pp. 7422-7430, 2012.
Na, et al., "Development of a Dielectric Barrier Discharge Ion Source for Ambient Mass Spectrometry", Journal of The American Society for Mass Spectrometry, Elsevier Science Inc, vol. 18, No. 10, pp. 1859-1862, Sep. 20, 2007.
Lee et al., "Thermally Assisted Electrospray Interface for Liquid Chromatography/Mass Spectrometry", Rapid Communications in Mass Spectrometry, vol. 6, pp. 727-733, 1992.
McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.
Sakairi et al., "Characteristics of a Liquid Chromatograph/Atmospheric Pressure Ionization Mass Spectrometer", Anal. Chem., vol. 60, pp. 774-780, 1988.
Takats et al., "Characterization of DESI-FTICR Mass Spectrometry—From ECD to Accurate Mass Tissue Analysis", Journal of Mass Spectrometry, vol. 43, pp. 196-203, 2008.
Eagles, et al., "Fast Atom Bombardment Mass Spectrometry of Amine Mixtures", John Wiley & Sons, Ltd, 1988.
Slemr et al., Concentration Profiles of Diamines in Fresh and aerobically Stored Park and Beef, American Chemical Society, 1985.
Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).
Van Berkel, "Thin-Layer Chromatography and El3ectrospray Mass Spectrometry Coupled Using a Surface Sampling probe". Anal. Chem. 2002.
Takats et al., "Mass Spectrometry Sampling Under Ambient Conditions with Desorption Electrospray Ionization", Science, vol. 306, 2004.
Tottszer et al., "Laser Heating Versus Resistive Heating in the Field-Desorption Mass Spectrometry of Organic Polymers", J. Phys. D: Appl. Phys., vol. 21, pp. 1713-1720, 1988.
Hsu, et al., "Microscopy ambient ionization top-down mass spectrometry reveals developmental patterning", Proceedings of the National Academy of Sciences, vol. 110, No. 37, pp. 14855-14860, Aug. 22, 2013.
Zhou, X., et al., "Development of miniature mass spectrometry systems for bioanalysis outside the conventional laboratories." Bioanalysis, 6 (11) 1497-1508 (2014).
Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).
McJimpsey, E.L., et al., "Parameters Contributing to Efficient Ion Generation in Aerosol MALDI Mass Spectrometry," American Society for Mass Spectrometry pp. 1044-0305 (2007).
Mutters, N.T., et al., "Performance of Kiestra Total Laboratory Automation Combined with MS in Clinical Microbiology Practice," Annals of Laboratory Medicine 34: 111-117 (2014).
Longuespee, R., et al., Tissue Proteomics for the Next Decade? Towards a Molecular Dimension in Histology, OMICS A Journal of Integrative Biology 28(9): 539-552 (2014).
Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).
Suarez, S., et al., Ribosomal proteins as biomarkers for bacterial identification by mass spectrometry in the clinical microbiology laboratory, Journal of microbiological Methods, 94: 390-396 (2013).
Schäfer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.
International Search Report and Written Opinion for International Application No. PCT/GB2016/052956, dated Jan. 26, 2017, 16 pages.
Asano et al., "Self-aspirating atmospheric pressure chemical ionization source for direct sampling of analytes on Surfaces in liquid solution", Rapid Communications in Mass Spectrometry 2005.
International Search Report and Written Opinion for application No. PCT/GB2017/051050, dated Jun. 27, 2017, 15 pages.
Gerbig, Stefanie et al, "Spatially resolved investigation of systemic and contact pesticides in plant material by desorption electrospray ionization mass spectrometry imagine", Analytical and Bioanalytical Chemistry, 407 (24):7379-7389 (2015).

(56) References Cited

OTHER PUBLICATIONS

Lesiak, A., et al., "Rapid detection by direct analysis in real time-mass spectrometry (DART-MS) of psychoactive plant drugs of abuse: the case of Mitragyna speciosa aka "Kratom"", 242:210-218 (2014).
Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).
Nielen, M et al., "Desorption electrospray ionization mass spectrometry in the analysis of chemical food contaminants in food", Trac Trends in Analytical Chemistry, 30(2)165-180 (2011).
Boughton, B. et al., "Mass spectrometry imaging for plant biology: a review", Phytochemistry Reviews, 15(3):445-488 (2015).
Cho, YT., et al. "Differentiation of Virulence of Helicobacter Pyloriby Matrix-Assited Laser Desorption/Ionization Mass Spectrometry and Multivariate Analyses" Clinica Chimica ACTA, Elsevier BV, 424:123-130, May 26, 2013.
Dong, Y., et al., "Sample Preparation for Mass Spectrometry Imaging of Plant Tissues: A Review", Frontiers in Plant Science 7(60): 1-16 (2016).
Communication pursuant to Article 94(3) EPC, for application No. 16710788.7, dated Jun. 13, 2019, 9 pages.
Examination Report under Section 18(3), for application No. GB1714122.7, dated May 9, 2019, 6 pages.
Bagley, B.M., et al., "Evaluation of archival time on shotgun proteomics of formalin-fixed and paraffin-embedded tissues", Journal of Proteome Research 8(2):917-925, (2009).
Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.
Hachmoeller et al., "Element bioimaging of liver needle biopsy specimens from patients with Wilson's disease by laser ablation-inductively coupled plasma-mass spectrometry", Journal of Trace Elements in Medicine and Biology, 35:97-102, Feb. 10, 2016.
Guenther et al., "Spatially Resolved Metabolic Phenotyping of Breast Cancer by Desorption Electrospray Ionization Miass Spectrometry", Cancer Research, 75:1828-1837, Feb. 17, 2015.
Chipuk, J. E., et al., "Transmission Mode Desorption Electrospray Ionization", Journal of the American Society for Mass Spectrometry, 19(11):1612-1620, Nov. 1, 2008.
Santagata, S., et al., "Intraoperative mass spectrometry mapping of an onco-metabolite to guide brain tumor surgery", Proceedings of the National Academy of Sciences (PNAS), 111 (30): 11121-11126, Jun. 30, 2014.
Kohler, M. et al. "Characterization of lipid extracts from brain tissue and tumors using Raman spectroscopy and mass spectrometry," Anal Bioana Chem, 393:1513-1520, Jan. 20, 2009.
Harry, K. H., et al. "Effect of protein coating of flocked swabs on the collection and release of clinically important bacteria", Indian Journal of Medical Microbiology, 32(3):301-303 (2014).
Blais, B. W., "Swab-Based Enzyme Immunoassay System for Detection of Meat Residues on Food Contact Surfaces as a Hygiene Monitoring Tool", Journal of Food Protection, 62(4):386-389 (1999).
Farhat, S. E., et al., "Efficacy of a Swab Transport System in Maintaining Viability of Neisseria gonorrhoeae and *Streptococcus pneumoniae*", Journal of Clinical Microbiology, 39(8):2958-2960 (2001).
Chen, H., et al., "What Can We Learn from Ambient Ionization Techniques?", Journal of the American Society for Mass Spectrometry, 20:1947-1963, (2009).
Ganesh, S., et al., "Common Uses and Cited Complications of Energy in Surgery", Surg Endosc., 27:3056-3072, (2013).
Rau, H.G., et al., "The use of water-jet dissection in open and laparoscopic liver resection", HPB, 10: 275280, (2008).
Chen et al. "Desorption Electrospray Ionization Mass spectrometry for high-throughput analysis of Pharmaceutical samples in the ambient environment" (2005).

Vemury, S., and Pratsinis, S.E., "Charging and Coagulation During Flame Synthesis of Silica", Journal of Aerosol Science 27(6)1951-966 (1996).
Examination Report under Section 18(3), for application No. GB1715787.6, dated Jun. 1, 2020, 6 pages.
Panpradist, N., et al., "Swab Sample Transfer for Point-Of-Care Diagnostics: Characterization of Swab types and Manual Agitation Methods", PLOS One 9(9):1-11 (2014).
CNOA 201680026285.3 dated Jun. 12, 2020, 12 pages.
Partial European Search Report for EP20181905.9, dated Aug. 27, 2020, 14 pages.
Roddy, T., et al., "Imaging of Freeze-Fractured Cells with in Situ Fluorescence and Time-of-Flight Secondary Ion Mass Spectrometry", Analytical Chemistry 74(16):4011-401 9 (2002).
Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78 (23)17959-7966 (2006).
Ablonczy, Z., et al., "The utilization of fluorescence to identify the components of lipofuscin by imaging mass spectrometry", Proteomics 14(7-8)1936-944.
Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).
Extended EP search report for EP Application No. 20172634.6, dated Sep. 14, 2020, 8 pages.
Adams, F., et al., "Inorganic Mass Spectrometry", (1993) Abstract.
Dong, Y.M.B.A., "Polymer Analysis Handbook", China Petromchemical Press (2004) 8 pages.
CNOA for application No. CN201680025801.0 dated Oct. 12, 2020 for corresponding app original document and translation.
Office Action for CN Patent Application No. 201680025801.0 dated Apr. 7, 2020.
Office Action for CN Patent Application No. 201680025801.0 dated Apr. 7, 2020 [translation].
Adams, F., et al., "Inorganic Mass Spectrometry", copyright John Wiley Sons, Inc. pp. 174-180 (1988).
Sankaranarayanan, G., et al., "Common Uses and Cited Complications of Energy in Surgery", Surg Endosc., 27:3056-3072, (2013).
Examination Report under Section 18(3) for Application No. GB1714165.6, dated Mar. 22, 2021, 6 pages.
Examination Report under Section 18(3) for Application No. GB1715750.4 dated Mar. 22, 2021, 5 pages.
Arena, K., et al., "Exploration of Rapid Evaporative-Ionization Mass Spectrometry as a Shotgun Approach for the Comprehensive Characterization of Kigelia Africana (Lam) Beth. Fruit", Molecules 25(4) 19 pages (2020).
Combined Search and Examination Report under Sections 17 and 18(3), for Application No. GB2110454.2, dated Aug. 19, 2021, 9 pages.
CNOA for Application No. 201910350273.1 dated May 8, 2021, 15 pages.
Dixit, et al., "Development of a High Sensitivity Rapid Sandwich ELISA Procedure and Its Comparison with the Conventional Approach", Anal Chem 82(16):7049-7052 (2010).
Gholami, A.M., et al., "Global Proteome Analysis of the NCI-60 Cell Line Panel", Cell Reports 4(3):609-620 (2013).
Hanson, et al., "Polymer-coated reversed-phase packings in high-performance liquid chromatography", J Chromat. A656:369-380 (1993). Abstract.
Herog, R., et al., "LipidXplorer: A Software for Consensual Cross-Platform Lipidomics" PloS ONE 7(1): e29851.
Hillenkamp, F., et al., "Matrix-Assisted Laser Desorption/Ionization Mass Spectrometry of Biopolymers", Anal Chem 63 (24): 1193A-1203A (1991). Abstract.
Hrabak, J., et al., "Matrix-Assisted Laser Desorption Ionizataion-Time of Flight (MALDI-TOF) Mass Spectrometry for Detection of Antibiotic Resistance Mechanisms: from Research to Routine Diagnosis", CMR Journal 26(1): 103-114 (2013).
Kind, T., et al., "LipidBlast—in-silico tandem mass spectrometry database for lipid identification", Nat Methods 10 (8):755-758 (2013).

(56) References Cited

OTHER PUBLICATIONS

Knockenmuss, R., "Ion Formation Mechanisms in UV-MALDI" Analyst 131:966-986 (2006).

Krishtalik, Lev I., "The mechanism of the proton transfer: an outline", Biochimica et Biophysica Acta (BBA)—Bioenergetics 1458(1):6-27 (2000).

Lipid Maps® [online] [retrieved on Jul. 2, 2021]. Retrieved from URL: http://www.lipidmaps.org , 3 pages.

Shamir, E.R., Ewald, A.J., "Three-dimensional organotypic culture: experimental models of mammalian biology and disease", Nature Rev Mol Cell Biol 15(10):647-664 (2014).

Shoemaker, Robert H., "The NCI60 Human Tumour Cell Line Anticancer Drug Screen", Nature Reviews Cancer 6:813-823(2006).

Weinstein, "Integromic analysis of the NCI-60 cancer cell lines", Breast Dis 19:11-22 (2004). Abstract.

White, D.C., et al., "Fatty Acid Composition of the Complex Lipids of *Staphylococcus aureus* During the Formation of Membrane-bound Electron Transport System", Journal of Bacteriology 95:2198-2209 (1968).

CNOA for Application No. 201680026939.2, dated Apr. 27, 2021, original 10 pp.

Examination Report under Section 18(3) for Application No. GB1715750.4, dated Oct. 11, 2021, 5 pages.

Office Action for Chinese Application No. CN20191104563.7, dated Oct. 11, 2021, original document 14 pages.

Chen Liru, "Ambient Mass Spectrometry for Fast Identification of Lung Cancer", Chinese Doctoral Dissertations Wasters Theses Full-text Database (Master) Medicine and Health Sciences—Nanchang University Jun. 7, 2014, original document and translation, 13 pages.

Chinese office action for application No. CN202010611251.9, dated Dec. 10, 2021, original document, 22 pages.

Chinese office action for application No. 201910350273.1 dated Dec. 3, 2021, original document 19 pages.

\* cited by examiner

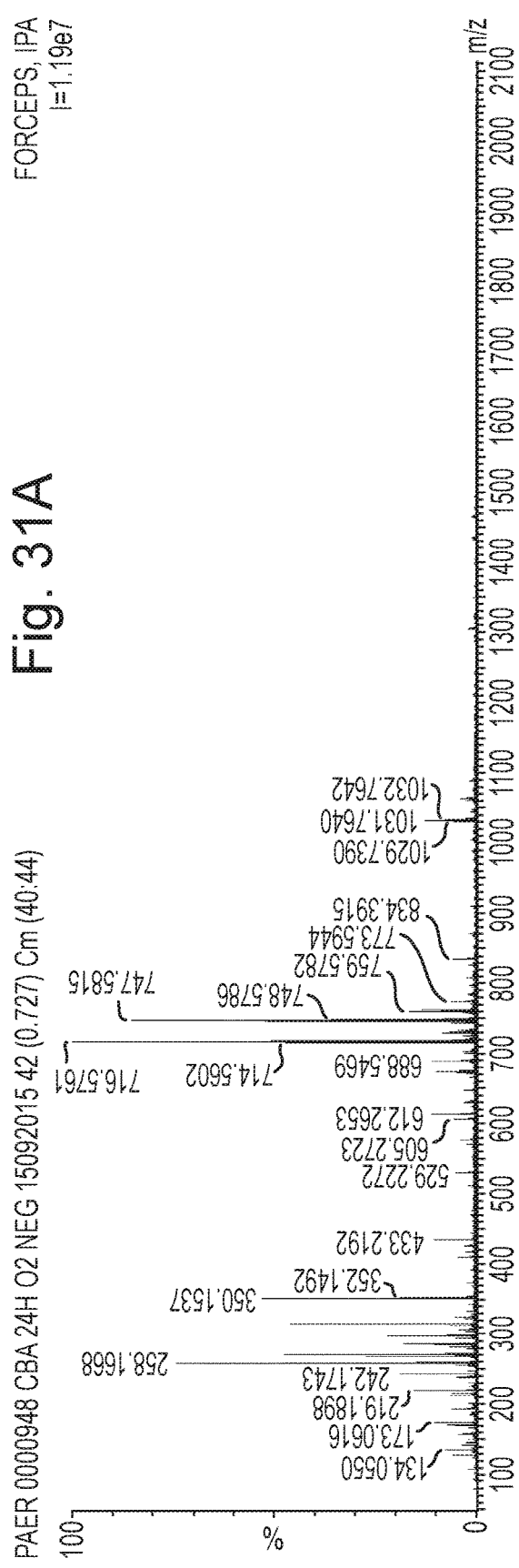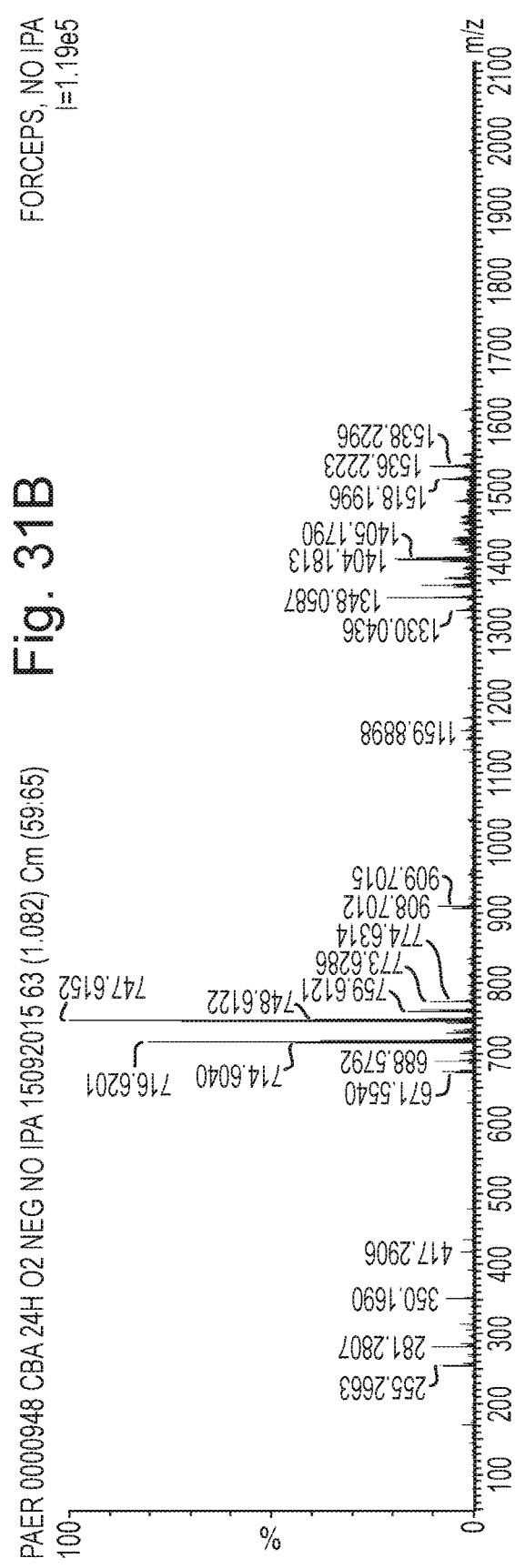

AMBIENT IONIZATION MASS SPECTROMETRY IMAGING PLATFORM FOR DIRECT MAPPING FROM BULK TISSUE

CROSS-REFERENCE TO RELATED APPLICATION

This application represents the U.S. National Phase of International Application number PCT/GB2016/050626 entitled "Ambient Ionization Mass Spectrometry Imaging for Direct Mapping From Bulk Tissue" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention generally relates to mass spectrometry, and in particular to methods of ion imaging, methods of electrosurgery, ion imagers, mass spectrometers and electrosurgical devices. Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

Mass spectrometry imaging ("MSI") analysis of biological samples is known and allows simultaneous and spatially resolved detection of metabolites, proteins and lipids directly from biological tissue sections.

The technique has gained significant momentum during the course of the last two decades with the introduction of new techniques such as matrix assisted laser desorption/ionization ("MALDI"), secondary ion mass spectrometry ("SIMS") and desorption electrospray ionization ("DESI").

The spatially resolved nature of the resulting data allows its use as a supplemental layer of information for histopathological characterization and classification of tissues including the possibility of cancer biomarker discovery.

Rapid evaporative ionization mass spectrometry ("REIMS") may be used for the real time identification of tissues e.g., during surgical interventions. Coupling of mass spectrometry with a surgical diathermy device has resulted in a technology known as intelligent knife ("iKnife") technology which has an intra-operative tissue identification accuracy of 92-100%.

iKnife technology allows surgeons to more efficiently resect tumours intra-operatively through minimizing the amount of healthy tissue removed whilst ensuring that all the cancerous tissue is removed.

Rapid evaporative ionization mass spectrometry analysis of biological tissue has been shown to yield phospholipid profiles showing high histological and histopathological specificity—similar to Matrix Assisted Laser Desorption Ionisation ("MALDI"), Secondary Ion Mass Spectrometry ("SIMS") and Desorption Electrospray Ionisation ("DESI") imaging. A mass spectrometric signal is obtained by subjecting the cellular biomass to alternating electric current at radiofrequency which causes localized Joule-heating and the disruption of cells along with desorption of charged and neutral particles. The resulting aerosol or surgical smoke is then transported to a mass spectrometer and/or ion mobility spectrometer for on-line mass spectrometric and/or ion mobility analysis.

Conventional rapid evaporative ionization mass spectrometry profiling applications require a spectral library of reference mass spectra in order to build multivariate classification models which are necessary for pattern-based identification.

Current iKnife technology reference mass spectra are obtained by manual electrosurgical sampling of ex vivo tissue specimens followed by the histopathological examination of the remaining material. Although the conventional workflow provides satisfactory data, there is a degree of uncertainty involved at the validation step since the tissue part producing the spectral data cannot be investigated since it is evaporated during the course of the analysis. Hence, conventionally all identifications are based on interpolation of the histological environment of the evaporated tissue.

It is desired to provide an improved method of ion imaging.

SUMMARY

According to an aspect there is provided a method of ion imaging. The method includes automatically sampling a plurality of different locations on a sample using a first device arranged and adapted to generate aerosol, smoke or vapour from the sample, obtaining mass spectral data and/or ion mobility data corresponding to each location, and using the obtained mass spectral data and/or ion mobility data to construct, train or improve a sample classification model.

In contrast to the known manual data collection approach, exemplary embodiments relate to an automated computer-controlled method of ambient ionization mass spectrometry (including rapid evaporation mass spectrometry ("REIMS")) sampling of tissue specimens wherein the 3D tissue environment may be used for histological validation.

In some embodiments, an ambient ionization mass spectrometry imaging device may be used in a minimally invasive fashion for the analysis of macroscopic tissue slices (not histological sections) and both the adjacent slice and the remaining tissue material may be fixed, embedded, sectioned, stained and histologically examined.

Although the very cells giving the spectral data may still be evaporated, the complete 3-dimensional adjacent environment gives sufficient information about their histological classification. Exemplary embodiments provide an imaging platform for systematic ambient ionization mass spectrometry data and/or ion mobility data collection which can serve as a basis for iKnife technology applications.

Further embodiments provide a mass spectrometric imaging platform for sample preparation-free ambient imaging MS analysis of biological samples.

Rapid evaporation ionization mass spectrometry ("REIMS") technology allows real time intra-operative tissue classification. In order to create spectral libraries for training the classification models, reference data needs to be acquired in large quantities as classification accuracy generally improves as a function of number of training samples.

Various aspects provide automated high-throughput methods for collecting ambient ionization mass spectrometry data and/or ion mobility data from heterogeneous organic tissue.

In exemplary embodiments, the instrumentation includes a 2D stage with an additional high-precision z-axis actuator which may be equipped with an electrosurgical diathermy-based sampling probe.

The sample may include a biological sample, a biological tissue, human tissue, animal tissue biological matter, a bacterial colony, a fungal colony or one or more bacterial strains. In general, the method may comprise a non-surgical or non-therapeutic method of ion imaging.

The sample can comprise native or unmodified sample material.

The native or unmodified sample material may be unmodified by the addition of a matrix or reagent.

The biological tissue may comprise in vivo biological tissue, ex vivo biological tissue or in vitro biological tissue.

The biological tissue comprises either: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The sample classification model may include a biological sample classification model, a biological tissue classification model, a human tissue classification model, an animal tissue classification model, a biological matter classification model, a bacterial colony classification model, a fungal colony classification model or a bacterial strain classification model.

Constructing, training or improving the sample classification model may be in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of sample material; (v) to determine whether or not one or more desired or undesired substances are present in the sample; (vi) to confirm the identity or authenticity of the sample; (vii) to determine whether or not one or more impurities, illegal substances or undesired substances are present in the sample; (viii) to determine whether a human or animal patient is at an increased risk of suffering an adverse outcome; (ix) to make or assist in the making a diagnosis or prognosis; and (x) to inform a surgeon, nurse, medic or robot of a medical, surgical or diagnostic outcome.

Using the obtained mass spectral data and/or ion mobility data to construct, train or improve the sample classification model may comprise performing a supervised or unsupervised multivariate statistical analysis of the mass spectral data and/or ion mobility data.

The multivariate statistical analysis may be selected from the group consisting of: (i) principal component analysis ("PCA"); and (ii) linear discriminant analysis ("LDA").

The method may further comprise analysing a profile of the aerosol, smoke or vapour or a profile of ions derived from the aerosol, smoke or vapour.

The profile may be selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

In some embodiments, the method may further include automatically translating the sample relative to the first device before and/or during and/or after obtaining mass spectral data and/or ion mobility data from at least some of the locations on the sample.

The first device may comprise or form part of an ambient ion or ionization source or the first device may generate the aerosol, smoke or vapour for subsequent ionization by an ambient ion or ionization source or other ionization source.

The first device may be arranged and adapted to generate aerosol, smoke or vapour from the sample without the sample requiring prior preparation.

The first device may comprise an ion source selected from the group consisting of: (i) a rapid evaporative ionization mass spectrometry ("REIMS") ion source; (ii) a desorption electrospray ionization ("DESI") ion source; (iii) a laser desorption ionization ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionization ion source; (x) an easy ambient sonic-spray ionization ("EASI") ion source; (xi) a desorption atmospheric pressure photoionization ("DAPPI") ion source; (xii) a paperspray ("PS") ion source; (xiii) a jet desorption ionization ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionization ("PESI") ion source; (xix) a solid-probe assisted electrospray ionization ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The first device may include one or more electrodes or one or more electrosurgical tips and the step of automatically sampling the plurality of different locations on the sample using the first device may further comprise contacting the sample with the one or more electrodes or the one or more electrosurgical tips at each location.

The one or more electrodes or the one or more electrosurgical tips may include a monopolar device. In some embodiments, a separate return electrode can also be provided.

The one or more electrodes or the one or more electrosurgical tips may include a bipolar device or a multi phase RF device, wherein the method optionally further comprises providing a separate return electrode or electrodes.

The one or more electrodes or the one or more electrosurgical tips may comprise a rapid evaporation ionization mass spectrometry ("REIMS") device.

The step of automatically sampling a plurality of different locations on the sample may further include applying an AC or RF voltage to the one or more electrodes or the one or more electrosurgical tips.

The step of applying the AC or RF voltage to the one or more electrodes or the one or more electrosurgical tips may further comprise applying one or more pulses of the AC or RF voltage to the one or more electrodes or the one or more electrosurgical tips.

The step of applying the AC or RF voltage to the one or more electrodes or the one or more electrosurgical tips may cause heat to be dissipated into the sample.

In exemplary embodiments, the amplitude, peak to peak voltage, or RMS voltage of the RF voltage, a peak to peak voltage or a RMS voltage is selected from the group consisting of: (i) <about 100 V; (ii) about 100-200 V; (iii) about 200-300 V; (iv) about 300-400 V; (v) about 400-500 V; (vi) about 500-600 V; (vii) about 600-700 V; (viii) about 700-800 V; (ix) about 800-900 V; (x) about 900-1000 V; and (xi) >about 1 kV.

In exemplary embodiments, the RF voltage may have a frequency selected from the group consisting of: (i) <about 1 kHz; (ii) about 1-2 kHz; (iii) about 2-3 kHz; (iv) about 3-4 kHz; (v) about 4-5 kHz; (vi) about 5-6 kHz; (vii) about 6-7 kHz; (viii) about 7-8 kHz; (ix) about 8-9 kHz; (x) about 9-10 kHz; (xi) about 10-20 kHz; (xii) about 20-30 kHz; (xiii) about 30-40 kHz; (xiv) about 40-50 kHz; (xv) about 50-60 kHz; (xvi) about 60-70 kHz; (xvii) about 70-80 kHz; (xviii) about 80-90 kHz; (xix) about 90-100 kHz; (xx) about 100-200 kHz; (xxi) about 200-300 kHz; (xxii) about 300-400 kHz; (xxiii) about 400-500 kHz; (xxiv) about 500-600 kHz; (xxv) about 600-700 kHz; (xxvi) about 700-800 kHz; (xxvii) about 800-900 kHz; (xxviii) about 900-1000 kHz; (xxix) about 1-2 MHz; and (xxx) >about 2 MHz.

The first device may be arranged and adapted to generate aerosol, smoke or vapour from the sample by direct evaporation or vaporisation of target material from the sample by Joule heating or diathermy.

The aerosol, smoke or vapour may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol is in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The first device may comprise a point of care ("POC"), diagnostic or surgical device.

The method may further comprise ionizing at least some of the aerosol, smoke or vapour so as to generate analyte ions.

Exemplary methods include aspirating the aerosol, smoke or vapour produced from the sample. In some embodiments, the method may further include aspirating the aerosol, smoke or vapour in a substantially pulsed, discontinuous or irregular manner. The method may further include aspirating the aerosol, smoke or vapour substantially only when an electrosurgical cutting applied voltage or potential is supplied to the one or more electrodes or the one or more electrosurgical tips. In some embodiments, the method may further include varying an aspiration duty cycle during the course of a surgical, non-surgical or other procedure.

In exemplary embodiments, the method may further include passing the aerosol, smoke or vapour into a vacuum chamber of a mass spectrometer and/or ion mobility spectrometer. The method may further comprise ionizing at least some of the aerosol, smoke or vapour within a or the vacuum chamber of the mass spectrometer and/or ion mobility spectrometer so as to generate analyte ions. In some embodiments, the method may further include causing at least some of the aerosol, smoke or vapour to impact upon a collision surface located within a vacuum chamber of the mass spectrometer and/or ion mobility spectrometer.

At least some of the aerosol, smoke or vapour may be ionized upon impacting the collision surface so as to generate analyte ions.

In some embodiments, the method may further include heating the collision surface.

The step of heating the collision surface may include heating the collision surface to a temperature selected from the group consisting of: (i) <about 100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) >about 1100° C.

In exemplary embodiments, the method can also include mass analysing and/or ion mobility analysing the analyte ions in order to obtain the mass spectral data and/or ion mobility data corresponding to each location.

The method may further comprise mass analysing and/or ion mobility analysing the aerosol, smoke or vapour or ions derived from the aerosol, smoke or vapour in order to obtain the mass spectral data and/or ion mobility data corresponding to each location.

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

In some embodiments, the method may further include adding a matrix to the aerosol, smoke or vapour. The matrix may be added to the aerosol, smoke or vapour prior to the aerosol, smoke or vapour impacting upon the collision surface. In exemplary embodiments, the matrix may be selected from the group consisting of: (i) a solvent for the aerosol, smoke or vapour; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; (xvii) an aldehyde; (xviii) a ketone; (xiv) non-polar molecules; (xx) hexane; (xxi) chloroform; (xxii) butanol; and (xxiii) propanol. In some embodiments, the matrix may include a lockmass or calibration compound.

In exemplary embodiments, the method may further include operating the first device in a cutting mode of operation. In such embodiments, the first device may form one or more substantially continuous cuts in the sample. In some embodiments, the method may further include maintaining the first device at substantially the same height over the sample whilst performing the one or more substantially continuous cuts in the sample. In some embodiments, the method may further include maintaining the first device in substantially continuous contact with the sample whilst performing the one or more substantially continuous cuts in the sample. In some embodiments, the method may further include operating the first device in a pointing mode of operation. In some embodiments, the method may further include lowering the first device so as to contact the sample and to acquire mass spectral data and/or ion mobility data and then raising the first device after contacting the sample and prior to acquiring further mass spectral data and/or ion mobility data.

In exemplary embodiments, the method may further include obtaining an optical image of the sample. In some embodiments, the method may further include substantially co-registering the optical image and an ion image. In some embodiments, the method may further include defining one or more regions of interest in the optical image and/or the ion image. The method can include, in some embodiments, determining a class or classification of one or more regions of interest. For example, the class or classification may include a healthy status, a pre-cancerous status, a cancerous status or a bacterial strain.

Another aspect provides a method that includes sampling a plurality of different locations of a sample using a first device arranged and adapted to generate aerosol, smoke or vapour from the sample to obtain mass spectral data and/or ion mobility data at each location, and using a sample classification model which was previously constructed, trained or improved according to a method of ion imaging as described above in order to classify the sample at each location.

A further aspect provides a method of electrosurgery. The method includes using one or more electrodes or one or more electrosurgical tips to acquire a sample from a plurality of different locations of a biological tissue using a first device arranged and adapted to generate aerosol, smoke or vapour from the biological tissue, obtaining mass spectral data and/or ion mobility data at each location, and using a biological tissue classification model which was previously constructed, trained or improved according to a method of ion imaging as described above in order to classify the biological tissue at each location.

Another aspect provides an ion imager. The ion imager includes a first device arranged and adapted to generate aerosol, smoke or vapour from a sample and a control system. The control system is arranged and adapted to automatically sample a plurality of different locations on the sample using the first device and to obtain mass spectral data and/or ion mobility data corresponding to each location and to use the obtained mass spectral data and/or ion mobility data to construct, train or improve a sample classification model.

In exemplary embodiments, the sample may include a biological sample, a biological tissue, human tissue, animal tissue, biological matter, a bacterial colony, a fungal colony or one or more bacterial strains. Corresponding sample classification models may include a biological sample classification model, a biological tissue classification model, a human tissue classification model, an animal tissue classification model, a biological matter classification model, a bacterial colony classification model, a fungal colony classification model or a bacterial strain classification model.

In some embodiments, the ion imager may further include a device arranged and adapted to automatically translate the sample relative to the first device any one or more of before, during, and after obtaining mass spectral data and/or ion mobility data from at least some of the locations on the sample.

The first device may comprise or form part of an ambient ion or ionization source or wherein the first device generates the aerosol, smoke or vapour for subsequent ionization by an ambient ion or ionization source or other ionization source.

The first device may comprise an ion source selected from the group consisting of: (i) a rapid evaporative ionization mass spectrometry ("REIMS") ion source; (ii) a desorption electrospray ionization ("DESI") ion source; (iii) a laser desorption ionization ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionization ion source; (x) an easy ambient sonic-spray ionization ("EASI") ion source; (xi) a desorption atmospheric pressure photoionization ("DAPPI") ion source; (xii) a paperspray ("PS") ion source; (xiii) a jet desorption ionization ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionization ("PESI") ion source; (xix) a solid-probe assisted electrospray ionization ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

Exemplary first devices may include one or more electrodes or one or more electrosurgical tips and may be arranged and adapted to generate aerosol, smoke or vapour from the sample by contacting the sample with the one or more electrodes or the one or more electrosurgical tips at each location. The one or more electrodes or the one or more electrosurgical tips may include a monopolar device and, in some embodiments, a separate return electrode. In other embodiments, the one or more electrodes or the one or more electrosurgical tips may include a bipolar device or a multi phase RF device. The ion imager optionally further comprise a separate return electrode or electrodes The one or more electrodes or the one or more electrosurgical tips may comprise a rapid evaporation ionization mass spectrometry ("REIMS") device.

The ion imager may further include a device arranged and adapted to apply an AC or RF voltage to the one or more electrodes or the one or more electrosurgical tips. In exemplary embodiments, amplitude, peak to peak voltage, or RMS voltage of the RF voltage is selected from the group consisting of: (i) <about 100 V; (ii) about 100-200 V; (iii) about 200-300 V; (iv) about 300-400 V; (v) about 400-500 V; (vi) about 500-600 V; (vii) about 600-700 V; (viii) about 700-800 V; (ix) about 800-900 V; (x) about 900-1000 V; and (xi) >about 1 kV. In exemplary embodiments, the RF voltage has a frequency selected from the group consisting of: (i) <about 1 kHz; (ii) about 1-2 kHz; (iii) about 2-3 kHz; (iv) about 3-4 kHz; (v) about 4-5 kHz; (vi) about 5-6 kHz; (vii) about 6-7 kHz; (viii) about 7-8 kHz; (ix) about 8-9 kHz; (x) about 9-10 kHz; (xi) about 10-20 kHz; (xii) about 20-30 kHz; (xiii) about 30-40 kHz; (xiv) about 40-50 kHz; (xv) about 50-60 kHz; (xvi) about 60-70 kHz; (xvii) about 70-80 kHz; (xviii) about 80-90 kHz; (xix) about 90-100 kHz; (xx) about 100-200 kHz; (xxi) about 200-300 kHz; (xxii) about 300-400 kHz; (xxiii) about 400-500 kHz; (xxiv) about 500-600 kHz; (xxv) about 600-700 kHz; (xxvi) about 700-800 kHz; (xxvii) about 800-900 kHz; (xxviii) about 900-1000 kHz; (xxix) about 1-2 MHz; and (xxx) >about 2 MHz.

Exemplary embodiments of the ion imager may further include a device arranged and adapted to aspirate the aerosol, smoke or vapour produced from the sample. In some embodiments, the device may be arranged and adapted to aspirate the aerosol, smoke or vapour in a substantially pulsed, discontinuous or irregular manner. The device can also be arranged and adapted to aspirate the aerosol, smoke or vapour substantially only when an electrosurgical cutting applied voltage or potential is supplied to the one or more electrodes or the one or more electrosurgical tips. In some embodiments, the ion imager may further include a control system which is arranged and adapted to vary an aspiration duty cycle during the course of a surgical, non-surgical or other procedure.

In exemplary embodiments, the ion imager may further include a control system which is arranged and adapted to operate the first device in a cutting mode of operation. In such embodiments, the first device can form one or more substantially continuous cuts in the sample. In some embodiments, the ion imager may further include a control system which is arranged and adapted to maintain the first device at substantially the same height over the sample whilst performing the one or more substantially continuous cuts in the sample. In some embodiments, the ion imager may further include a control system which is arranged and adapted to maintain the first device in substantially continuous contact with the sample whilst performing the one or more substantially continuous cuts in the sample. In some embodiments, the ion imager may further include a control system which is arranged and adapted to operate the first device in a pointing mode of operation. In some embodiments, the control system may be arranged and adapted to lower the first device so as to contact the sample and to acquire mass spectral data and/or ion mobility data and then raise the first device after contacting the sample and prior to acquiring further mass spectral data and/or ion mobility data.

In exemplary embodiments, the ion imager may further include a control system which is arranged and adapted to obtain an optical image of the sample. In some embodiments, the control system may be arranged and adapted to substantially co-register the optical image and an ion image. In some embodiments, the control system may be arranged and adapted to define one or more regions of interest in the optical image and/or the ion image. In some embodiments, the control system may be arranged and adapted to determine a class or classification of one or more regions of interest.

The class or classification may include a healthy status, a pre-cancerous status, a cancerous status or a bacterial strain.

Another aspect provides a mass spectrometer and/or ion mobility spectrometer including an ion imager as described above.

In exemplary embodiments, the mass spectrometer and/or ion mobility spectrometer may further include tubing or other means which is arranged and adapted to pass the aerosol, smoke or vapour into a vacuum chamber of the mass spectrometer and/or ion mobility spectrometer. In some embodiments, the mass spectrometer and/or ion mobility spectrometer may further include a collision surface located within a vacuum chamber of the mass spectrometer and/or ion mobility spectrometer. For example, in use, at least some of the aerosol, smoke or vapour may be caused to impact upon the collision surface. At least some of the aerosol, smoke or vapour may be ionized upon impacting the collision surface so as to generate analyte ions.

The mass spectrometer and/or ion mobility spectrometer can also include a heater which is arranged and adapted to heat the collision surface.

The heater may be arranged and adapted to heat the collision surface to a temperature selected from the group consisting of: (i) <about 100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) >about 1100° C.

In exemplary embodiments, the mass spectrometer and/or ion mobility spectrometer may further include a mass analyser and/or ion mobility analyser for mass analysing and/or ion mobility analysing the analyte ions.

In some embodiments, the mass spectrometer and/or ion mobility spectrometer may further include a device which is arranged and adapted to add a matrix to the aerosol, smoke or vapour. The device may be arranged and adapted to add the matrix to the aerosol, smoke or vapour prior to the aerosol, smoke or vapour impacting upon the collision surface. In exemplary embodiments, the matrix may be selected from the group consisting of: (i) a solvent for the aerosol, smoke or vapour; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; (xvii) an aldehyde; (xviii) a ketone; (xiv) non-polar molecules; (xx) hexane; (xxi) chloroform; (xxii) butanol; and (xxiii) propanol. In some embodiments, the matrix may include a lockmass or calibration compound.

Another provides an apparatus including a first device arranged and adapted to generate aerosol, smoke or vapour from a sample and a control system. The control system is arranged and adapted to sample a plurality of different locations of the sample using the first device and to obtain mass spectral data and/or ion mobility data at each location, and to use a sample classification model which was previously constructed, trained or improved according to a method of ion imaging as described above in order to classify the sample at each location.

Another aspect provides an electrosurgical apparatus. The electrosurgical apparatus includes a first device arranged and adapted to generate aerosol, smoke or vapour from a biological tissue comprising one or more electrodes or one or more electrosurgical tips which are arranged and adapted to sample a plurality of different locations of the biological tissue, a mass spectrometer and/or ion mobility spectrometer arranged and adapted to obtain mass spectral data and/or ion mobility data at each location, and a control system which is arranged and adapted to use a biological tissue classification model which was previously constructed, trained or improved according to a method of ion imaging as described above in order to classify the biological tissue at each location.

Using the obtained mass spectral data and/or ion mobility data to construct, train or improve a sample classification model may comprise analysing one or more sample spectra of said mass spectral data and/or ion mobility data so as to classify an aerosol, smoke or vapour sample.

Analysing the one or more sample spectra so as to classify the aerosol, smoke or vapour sample may comprise supervised analysis of the one or more sample spectra and/or unsupervised analysis of the one or more sample spectra.

Analysing the one or more sample spectra so as to classify the aerosol, smoke or vapour sample may comprise using one or more of: univariate analysis; multivariate analysis; principal component analysis (PCA); linear discriminant analysis (LDA); maximum margin criteria (MMC); library-based analysis; soft independent modelling of class analogy (SIMCA); factor analysis (FA); recursive partitioning (decision trees); random forests; independent component analysis (ICA); partial least squares discriminant analysis (PLS-DA); orthogonal (partial least squares) projections to latent structures (OPLS); OPLS discriminant analysis (OPLS-DA); support vector machines (SVM); (artificial) neural networks; multilayer perceptron; radial basis function (RBF) networks; Bayesian analysis; cluster analysis; a kernelized method; and subspace discriminant analysis.

Analysing the one or more sample spectra so as to classify the aerosol, smoke or vapour sample may comprise developing a classification model or library using one or more reference sample spectra.

Analysing the one or more sample spectra so as to classify the aerosol, smoke or vapour sample may comprise performing linear discriminant analysis (LDA) after performing principal component analysis (PCA).

Analysing the one or more sample spectra so as to classify the aerosol, smoke or vapour sample may comprise performing a maximum margin criteria (MMC) process after performing principal component analysis (PCA).

Analysing the one or more sample spectra so as to classify the aerosol, smoke or vapour sample may comprise defining one or more classes within a classification model or library.

Analysing the one or more sample spectra so as to classify the aerosol, smoke or vapour sample may comprise defining one or more classes within a classification model or library manually or automatically according to one or more class or cluster criteria.

The one or more class or cluster criteria for each class may be based on one or more of: a distance between one or more pairs of reference points for reference sample spectra within a model space; a variance value between groups of reference points for reference sample spectra within a model space; and a variance value within a group of reference points for reference sample spectra within a model space.

The one or more classes may each be defined by one or more class definitions.

The one or more class definitions may comprise one or more of: a set of one or more reference points for reference sample spectra, values, boundaries, lines, planes, hyperplanes, variances, volumes, Voronoi cells, and/or positions, within a model space; and one or more positions within a class hierarchy.

Analysing the one or more sample spectra so as to classify the aerosol, smoke or vapour sample may comprise using a classification model or library to classify one or more unknown sample spectra.

Analysing the one or more sample spectra so as to classify the aerosol, smoke or vapour sample may comprise classifying one or more sample spectra manually or automatically according to one or more classification criteria.

The one or more classification criteria may comprise one or more of:

a distance between one or more projected sample points for one or more sample spectra within a model space and a set of one or more reference points for one or more reference sample spectra, values, boundaries, lines, planes, hyperplanes, volumes, Voronoi cells, or positions, within the model space being below a distance threshold or being the lowest such distance;

a position for one or more projected sample points for one or more sample spectra within a model space being one side or other of one or more reference points for one or more reference sample spectra, values, boundaries, lines, planes, hyperplanes, or positions, within the model space;

a position for one or more projected sample points for one or more sample spectra within a model space being within one or more volumes or Voronoi cells within the model space; and a probability or classification score being above a probability or classification score threshold or being the highest such probability or classification score.

Various embodiments are contemplated which relate to generating smoke, aerosol or vapour from a sample or a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the sample or the target in real time.

According to an embodiment the first device for generating aerosol, smoke or vapour from the sample or the target may comprise a tool which utilises an RF voltage, such as a continuous RF waveform.

Other embodiments are contemplated wherein the first device for generating aerosol, smoke or vapour from the sample or the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the sample or the target. Argon gas is emitted from the probe and is then ionized by a high voltage discharge (e.g., 6 kV). High-frequency electric current is then conducted through the jet of gas, resulting in coagulation of the sample or the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatanated with negative ion mode spectrometric data. Negative ion mode can provide particularly useful spectra for classifying aerosol, smoke or vapour samples, such as aerosol, smoke or vapour samples from samples or targets comprising lipids.

Ion mobility spectrometric data may be obtained using different ion mobility drift gases, or dopants may be added to the drift gas to induce a change in drift time of one or more species. This data may then be combined or concatenated.

It will be apparent that the requirement to add a matrix or a reagent directly to a sample may prevent the ability to perform in vivo analysis of tissue and also, more generally, prevents the ability to provide a rapid simple analysis of sample or target material.

According to other embodiments the ambient ionisation ion source may comprise an ultrasonic ablation ion source or a hybrid electrosurgical—ultrasonic ablation source that generates a liquid sample which is then aspirated as an aerosol. The ultrasonic ablation ion source may comprise a focused or unfocussed ultrasound.

Optionally, the first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device. Another aspect provides a method of ion imaging. In exemplary embodiments, the method includes automatically sampling a plurality of different locations on a sample using a rapid evaporation ionization mass spectrometry ("REIMS") device and obtaining mass spectral data corresponding to each the location, and using the obtained mass spectral data to construct, train or improve a sample classification model.

In contrast to the known manual data collection approach, exemplary embodiments relate to an automated computer-controlled method of rapid evaporative ionization mass spectrometry sampling of tissue specimens wherein the 3D tissue environment may be used for histological validation.

In some embodiments, a rapid evaporative ionization mass spectrometry imaging device may be used in a minimally invasive fashion for the analysis of macroscopic tissue slices (not histological sections) and both the adjacent slice and the remaining tissue material may be fixed, embedded, sectioned, stained and histologically examined.

Although the very cells giving the spectral data are still evaporated, the complete 3-dimensional adjacent environment gives sufficient information about their histological classification. Exemplary embodiments provide an imaging platform for systematic rapid evaporative ionization mass spectrometry data collection which can serve as a basis for iKnife technology applications.

Further embodiments provide a mass spectrometric imaging platform for sample preparation-free ambient imaging MS analysis of biological samples.

Rapid evaporation ionization mass spectrometry ("REIMS") technology allows real time intra-operative tissue classification. In order to create spectral libraries for training the classification models, reference data needs to be acquired in large quantities as classification accuracy generally improves as a function of number of training samples.

Various aspects provide automated high-throughput methods for collecting rapid evaporative ionization mass spectrometry data from heterogeneous organic tissue.

In exemplary embodiments, the instrumentation includes a 2D stage with an additional high-precision z-axis actuator which may be equipped with an electrosurgical diathermy-based sampling probe.

The sample may include a biological sample, a biological tissue, human tissue, animal tissue, biological matter, a bacterial colony, a fungal colony or one or more bacterial strains. In general, the method may comprise a non-surgical or non-therapeutic method of ion imaging.

The sample classification model may include a biological sample classification model, a biological tissue classification model, a human tissue classification model, an animal tissue classification model, a biological matter classification model, a bacterial colony classification model, a fungal colony classification model or a bacterial strain classification model.

In some embodiments, the method may further include automatically translating the sample relative to the rapid evaporative ionization mass spectrometry device before and/or during and/or after obtaining mass spectral data from at least some of the locations on the sample.

The rapid evaporative ionization mass spectrometry device may include one or more electrodes or one or more electrosurgical tips.

The one or more electrodes or the one or more electrosurgical tips may include a monopolar device. In some embodiments, a separate return electrode can also be provided.

The one or more electrodes or the one or more electrosurgical tips may include a bipolar device.

The step of automatically sampling a plurality of different locations on the sample may further include applying an RF voltage to the one or more electrodes or the one or more electrosurgical tips.

In exemplary embodiments, the amplitude, peak to peak voltage, or RMS voltage of the RF voltage, a peak to peak voltage or a RMS voltage is selected from the group consisting of: (i) <about 100 V; (ii) about 100-200 V; (iii) about 200-300 V; (iv) about 300-400 V; (v) about 400-500 V; (vi) about 500-600 V; (vii) about 600-700 V; (viii) about 700-800 V; (ix) about 800-900 V; (x) about 900-1000 V; and (xi) >about 1 kV.

In exemplary embodiments, the RF voltage has a frequency selected from the group consisting of: (i) <about 1 kHz; (ii) about 1-2 kHz; (iii) about 2-3 kHz; (iv) about 3-4 kHz; (v) about 4-5 kHz; (vi) about 5-6 kHz; (vii) about 6-7 kHz; (viii) about 7-8 kHz; (ix) about 8-9 kHz; (x) about 9-10 kHz; (xi) about 10-20 kHz; (xii) about 20-30 kHz; (xiii) about 30-40 kHz; (xiv) about 40-50 kHz; (xv) about 50-60 kHz; (xvi) about 60-70 kHz; (xvii) about 70-80 kHz; (xviii) about 80-90 kHz; (xix) about 90-100 kHz; (xx) about 100-200 kHz; (xxi) about 200-300 kHz; (xxii) about 300-400 kHz; (xxiii) about 400-500 kHz; (xxiv) about 500-600 kHz; (xxv) about 600-700 kHz; (xxvi) about 700-800 kHz; (xxvii) about 800-900 kHz; (xxviii) about 900-1000 kHz; (xxix) about 1-2 MHz; and (xxx) >about 2 MHz.

Exemplary methods include aspirating analyte, smoke, fumes, liquid, gas, surgical smoke, aerosol or vapour produced from the sample. In some embodiments, the method may further include aspirating the analyte, smoke, fumes, liquid, gas, surgical smoke, aerosol or vapour in a substantially pulsed manner. The method may further include aspirating the analyte, smoke, fumes, liquid, gas, surgical smoke, aerosol or vapour substantially only when an electrosurgical cutting applied voltage or potential is supplied to the one or more electrodes or the one or more electrosurgical tips. In some embodiments, the method may further include varying an aspiration duty cycle during the course of a surgical, non-surgical or other procedure.

In exemplary embodiments, the method may further include passing the analyte, smoke, fumes, liquid, gas, surgical smoke, aerosol or vapour into a vacuum chamber of a mass spectrometer. In some embodiments, the method may further include causing at least some of the analyte, smoke, fumes, liquid, gas, surgical smoke, aerosol or vapour to impact upon a collision surface located within a vacuum chamber of the mass spectrometer.

At least some of the analyte, smoke, fumes, liquid, gas, surgical smoke, aerosol or vapour may be ionized upon impacting the collision surface so as to form analyte ions.

In some embodiments, the method may further include heating the collision surface.

The step of heating the collision surface may include heating the collision surface to a temperature selected from the group consisting of: (i) <about 100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) >about 1100° C.

In exemplary embodiments, the method can also include mass analysing the analyte ions.

In some embodiments, the method may further include adding a matrix to the analyte, smoke, fumes, liquid, gas, surgical smoke, aerosol or vapour. The matrix may be added to the analyte, smoke, fumes, liquid, gas, surgical smoke, aerosol or vapour prior to the analyte, smoke, fumes, liquid, gas, surgical smoke, aerosol or vapour impacting upon the collision surface. In exemplary embodiments, the matrix may be selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile. In some embodiments, the matrix may include a lockmass or calibration compound.

In exemplary embodiments, the method may further include operating the rapid evaporative ionization mass spectrometry device in a cutting mode of operation. In such embodiments, the rapid evaporative ionization mass spectrometry device can form one or more substantially continuous cuts in the sample. In some embodiments, the method may further include maintaining the rapid evaporative ionization mass spectrometry device at substantially the same height whilst performing the one or more substantially continuous cuts in the sample. In some embodiments, the method may further include maintaining the rapid evaporative ionization mass spectrometry device in substantially continuous contact with the sample whilst performing the one or more substantially continuous cuts in the sample. In some embodiments, the method may further include operating the rapid evaporative ionization mass spectrometry device in a pointing mode of operation. In some embodiments, the method may further include lowering the rapid evaporative ionization mass spectrometry device so as to contact the sample and to acquire mass spectral data and then raising the rapid evaporative ionization mass spectrometry device after contacting the sample and prior to acquiring further mass spectral data.

In exemplary embodiments, the method may further include obtaining an optical image of the sample. In some embodiments, the method may further include substantially co-registering the optical image and an ion image. In some embodiments, the method may further include defining one or more regions of interest in the optical image and/or the ion image. The method can include, in some embodiments, determining a class or classification of one or more regions of interest. For example, the class or classification may include a healthy status, a pre-cancerous status, a cancerous status or a bacterial strain.

Another aspect provides a method that includes sampling a plurality of different locations of a sample using a rapid evaporation ionization mass spectrometry ("REIMS") device and obtaining mass spectral data at each the location, and using a sample classification model which was previously constructed, trained or improved according to a method of ion imaging as described above in order to classify the sample at each the location.

A further aspect provides a method of electrosurgery. In exemplary embodiments, the method includes using one or more electrodes or one or more electrosurgical tips to acquire a sample from a plurality of different locations of a biological tissue using a rapid evaporation ionization mass spectrometry ("REIMS") device and obtaining mass spectral data at each the location; and using a biological tissue classification model which was previously constructed, trained or improved according to a method of ion imaging as described above in order to classify the biological tissue at each the location.

Another aspect provides an ion imager. In exemplary embodiments, the ion imager includes a rapid evaporation ionization mass spectrometry ("REIMS") device and a control system. The control system may be arranged and adapted to automatically sample a plurality of different locations on a sample using the rapid evaporation ionization mass spectrometry ("REIMS") device and to obtain mass spectral data corresponding to each the location and to use the obtained mass spectral data to construct, train or improve a sample classification model.

In exemplary embodiments, the sample may include a biological sample, a biological tissue, human tissue, animal tissue, biological matter, a bacterial colony, a fungal colony or one or more bacterial strains. Corresponding sample classification models may include a biological sample classification model, a biological tissue classification model, a human tissue classification model, an animal tissue classification model, a biological matter classification model, a bacterial colony classification model, a fungal colony classification model or a bacterial strain classification model.

In some embodiments, the ion imager may further include a device arranged and adapted to automatically translate the sample relative to the rapid evaporative ionization mass spectrometry device any one or more of before, during, and after obtaining mass spectral data from at least some of the locations on the sample.

Exemplary rapid evaporative ionization mass spectrometry devices may include one or more electrodes or one or more electrosurgical tips. The one or more electrodes or the one or more electrosurgical tips may include a monopolar device and, in some embodiments, a separate return electrode. In other embodiments, the one or more electrodes or the one or more electrosurgical tips may include a bipolar device.

The ion imager may further include a device arranged and adapted to apply an RF voltage to the one or more electrodes or the one or more electrosurgical tips. In exemplary embodiments, amplitude, peak to peak voltage, or RMS voltage of the RF voltage is selected from the group consisting of: (i) <about 100 V; (ii) about 100-200 V; (iii) about 200-300 V; (iv) about 300-400 V; (v) about 400-500 V; (vi) about 500-600 V; (vii) about 600-700 V; (viii) about 700-800 V; (ix) about 800-900 V; (x) about 900-1000 V; and (xi) >about 1 kV. In exemplary embodiments, the RF voltage has a frequency selected from the group consisting of: (i) <about 1 kHz; (ii) about 1-2 kHz; (iii) about 2-3 kHz; (iv) about 3-4 kHz; (v) about 4-5 kHz; (vi) about 5-6 kHz; (vii) about 6-7 kHz; (viii) about 7-8 kHz; (ix) about 8-9 kHz; (x) about 9-10 kHz; (xi) about 10-20 kHz; (xii) about 20-30 kHz; (xiii) about 30-40 kHz; (xiv) about 40-50 kHz; (xv) about 50-60 kHz; (xvi) about 60-70 kHz; (xvii) about 70-80 kHz; (xviii) about 80-90 kHz; (xix) about 90-100 kHz; (xx) about 100-200 kHz; (xxi) about 200-300 kHz; (xxii) about 300-400 kHz; (xxiii) about 400-500 kHz; (xxiv) about 500-600 kHz; (xxv) about 600-700 kHz; (xxvi) about 700-800 kHz; (xxvii) about 800-900 kHz; (xxviii) about 900-1000 kHz; (xxix) about 1-2 MHz; and (xxx) >about 2 MHz.

Exemplary embodiments of the ion imager may further include a device arranged and adapted to aspirate analyte, smoke, fumes, liquid, gas, surgical smoke, aerosol or vapour produced from the sample. In some embodiments, the device may be arranged and adapted to aspirate the analyte, smoke, fumes, liquid, gas, surgical smoke, aerosol or vapour in a substantially pulsed manner. The device can also be arranged and adapted to aspirate the analyte, smoke, fumes, liquid, gas, surgical smoke, aerosol or vapour substantially only when an electrosurgical cutting applied voltage or potential is supplied to the one or more electrodes or the one or more electrosurgical tips. In some embodiments, the ion imager may further include a control system which is arranged and adapted to vary an aspiration duty cycle during the course of a surgical, non-surgical or other procedure.

In exemplary embodiments, the ion imager may further include a control system which is arranged and adapted to operate the rapid evaporative ionization mass spectrometry device in a cutting mode of operation. In such embodiments, the rapid evaporative ionization mass spectrometry device can form one or more substantially continuous cuts in the sample. In some embodiments, the ion imager may further include a control system which is arranged and adapted to maintain the rapid evaporative ionization mass spectrometry device at substantially the same height whilst performing the one or more substantially continuous cuts in the sample. In some embodiments, the ion imager may further include a control system which is arranged and adapted to maintain the rapid evaporative ionization mass spectrometry device in substantially continuous contact with the sample whilst performing the one or more substantially continuous cuts in the sample. In some embodiments, the ion imager may further include a control system which is arranged and adapted to operate the rapid evaporative ionization mass spectrometry device in a pointing mode of operation. In some embodiments, the control system may be arranged and adapted to lower the rapid evaporative ionization mass spectrometry device so as to contact the sample and to acquire mass spectral data and then raise the rapid evaporative ionization mass spectrometry device after contacting the sample and prior to acquiring further mass spectral data.

In exemplary embodiments, the ion imager may further include a control system which is arranged and adapted to obtain an optical image of the sample. In some embodiments, the control system may be arranged and adapted to substantially co-register the optical image and an ion image. In some embodiments, the control system may be arranged and adapted to define one or more regions of interest in the optical image and/or the ion image. In some embodiments, the control system may be arranged and adapted to determine a class or classification of one or more regions of interest.

The class or classification may include a healthy status, a pre-cancerous status, a cancerous status or a bacterial strain.

Another aspect provides a mass spectrometer including an ion imager as described above. In exemplary embodiments, the mass spectrometer may further include tubing or other means which is arranged and adapted to pass the analyte, smoke, fumes, liquid, gas, surgical smoke, aerosol or vapour into a vacuum chamber of the mass spectrometer. In some embodiments, the mass spectrometer may further include a collision surface located within a vacuum chamber of the mass spectrometer. For example, in use, at least some of the analyte, smoke, fumes, liquid, gas, surgical smoke, aerosol or vapour may be caused to impact upon the collision surface. At least some of the analyte, smoke, fumes, liquid, gas, surgical smoke, aerosol or vapour may be ionized upon impacting the collision surface so as to form analyte ions.

The mass spectrometer can also include a heater which is arranged and adapted to heat the collision surface.

The heater may be arranged and adapted to heat the collision surface to a temperature selected from the group consisting of: (i) <about 100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) >about 1100° C.

In exemplary embodiments, the mass spectrometer may further include a mass analyser for mass analysing the analyte ions.

In some embodiments, the mass spectrometer may further include a device which is arranged and adapted to add a matrix to the analyte, smoke, fumes, liquid, gas, surgical smoke, aerosol or vapour. The device may be arranged and adapted to add the matrix to the analyte, smoke, fumes, liquid, gas, surgical smoke, aerosol or vapour prior to the analyte, smoke, fumes, liquid, gas, surgical smoke, aerosol or vapour impacting upon the collision surface. In exemplary embodiments, the matrix may be selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile. In some embodiments, the matrix may include a lockmass or calibration compound.

Another provides an apparatus including a rapid evaporation ionization mass spectrometry ("REIMS") device and a control system. In exemplary embodiments, the control system is arranged and adapted to sample a plurality of different locations of a sample using the rapid evaporation ionization mass spectrometry ("REIMS") device and to obtain mass spectral data at each the location; and to use a sample classification model which was previously constructed, trained or improved according to a method of ion imaging as described above in order to classify the sample at each the location.

Another aspect provides an electrosurgical apparatus. In exemplary embodiments, the electrosurgical apparatus includes a rapid evaporation ionization mass spectrometry ("REIMS") device comprising one or more electrodes or one or more electrosurgical tips which are arranged and adapted to sample a plurality of different locations of a biological tissue; a mass spectrometer arranged and adapted to obtain mass spectral data at each the location; and a control system which is arranged and adapted to use a biological tissue classification model which was previously constructed, trained or improved according to a method of ion imaging as described above in order to classify the biological tissue at each the location.

BRIEF DESCRIPTION OF THE DRAWINGS

Various embodiments will now be described, by way of example only, and with reference to the accompanying drawings in which:

FIG. 31A shows forceps based rapid evaporative ionization mass spectrometry spectra profiles for *Pseudomonas aeruginosa* with IPA and FIG. 31B shows forceps based rapid evaporative ionization mass spectrometry spectra profiles for *Pseudomonas aeruginosa* without IPA.

DETAILED DESCRIPTION

Figure 1:
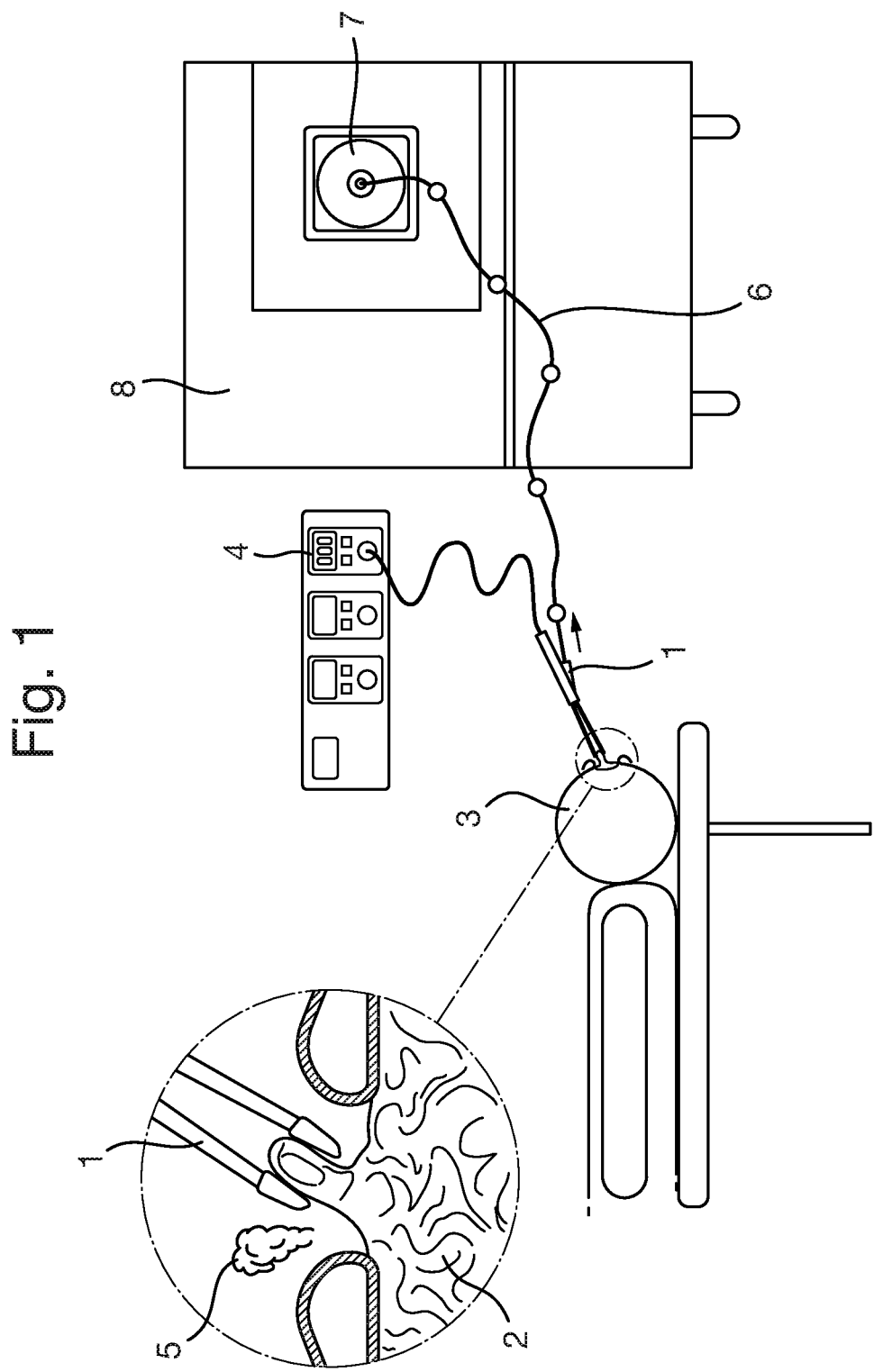
FIG. 1 illustrates a method of rapid evaporative ionization mass spectrometry ("REIMS") wherein an RF voltage is applied to bipolar forceps resulting in the generation of an aerosol or surgical plume which is captured through an irrigation port of the bipolar forceps and is then transferred to a mass spectrometer and/or ion mobility spectrometer for ionization and mass analysis and/or ion mobility analysis.

Various embodiments will now be described in more detail below which in general relate to an ion imager having an ambient ionization ion source device.

A plurality of different locations on a sample are automatically sampled using the device, and mass spectral data and/or ion mobility data corresponding to each location is obtained. The obtained mass spectral data and/or ion mobility data is then used to construct, train or improve a sample classification model.

Ambient Ionization Ion Sources

According to various embodiments a first device is arranged and adapted to generate an aerosol, smoke or vapour from a sample (e.g., in vivo tissue). The device may comprise an ambient ionization ion source which is characterized by the ability to generate analyte aerosol, smoke or vapour from a native or unmodified sample. For example, other types of ionization ion sources such as Matrix Assisted Laser Desorption Ionization ("MALDI") ion sources require a matrix or reagent to be added to the sample prior to ionization.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionization techniques are particularly advantageous since firstly they do not require the addition of a matrix or a reagent (and hence are suitable for the analysis of in vivo tissue) and since secondly they enable a rapid simple analysis of target material to be performed.

A number of different ambient ionization techniques are known and are intended to fall within the scope of the present invention. As a matter of historical record, Desorption Electrospray Ionization ("DESI") was the first ambient ionization technique to be developed and was disclosed in 2004. Since 2004, a number of other ambient ionization techniques have been developed. These ambient ionization techniques differ in their precise ionization method but they share the same general capability of generating gas-phase ions directly from native (i.e. untreated or unmodified) samples. A particular advantage of the various ambient ionization techniques which are intended to fall within the scope of the present invention is that the various ambient ionization techniques do not require any prior sample preparation. As a result, the various ambient ionization techniques enable both in vivo tissue and ex vivo tissue samples to be analyzed without necessitating the time and expense of adding a matrix or reagent to the tissue sample or other target material.

A list of ambient ionization techniques which are intended to fall within the scope of the present invention are given in the following Table 1:

TABLE 1

A list of ambient ionization techniques.

| Acronym | Ionisation technique |
|---|---|
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |

TABLE 1-continued

A list of ambient ionization techniques.

| Acronym | Ionisation technique |
|---|---|
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a $CO_2$ laser having a wavelength of 10.6 µm may be used to generate the aerosol, smoke or vapour.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the first device for generating aerosol, smoke or vapour from one or more regions of a target may comprise an electrosurgical tool which utilises a continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

Rapid Evaporative Ionization Mass Spectrometry ("REIMS")

FIG. 1 illustrates a method of rapid evaporative ionization mass spectrometry ("REIMS") wherein bipolar forceps 1 may be brought into contact with in vivo tissue 2 of a patient 3. In the example shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of a mass spectrometer and/or ion mobility spectrometer 8.

According to various embodiments a matrix comprising an organic solvent such as isopropanol (IPA) may be added to the aerosol or surgical plume 5 at the atmospheric pressure interface 7. The mixture of aerosol 3 and organic solvent may then be arranged to impact upon a collision surface within a vacuum chamber of the mass spectrometer and/or ion mobility spectrometer 8. According to one embodiment the collision surface may be heated. The aerosol is caused to ionize upon impacting the collision surface resulting in the generation of analyte ions. The ionization efficiency of generating the analyte ions may be improved by the addition of the organic solvent. However, the addition of an organic solvent is not essential.

Analyte ions which are generated by causing the aerosol, smoke or vapour 5 to impact upon the collision surface are then passed through subsequent stages of the mass spectrometer and/or ion mobility spectrometer and are subjected to mass analysis and/or ion mobility analysis in a mass analyser and/or ion mobility analyser. The mass analyser may, for example, comprise a quadrupole mass analyser or a Time of Flight mass analyser.

Sample Treatment

For the analysis of human samples, ethical approval was obtained from the National Healthcare Service Research Ethics Committee (Study ID 11/LO/1686).

Figure 2:
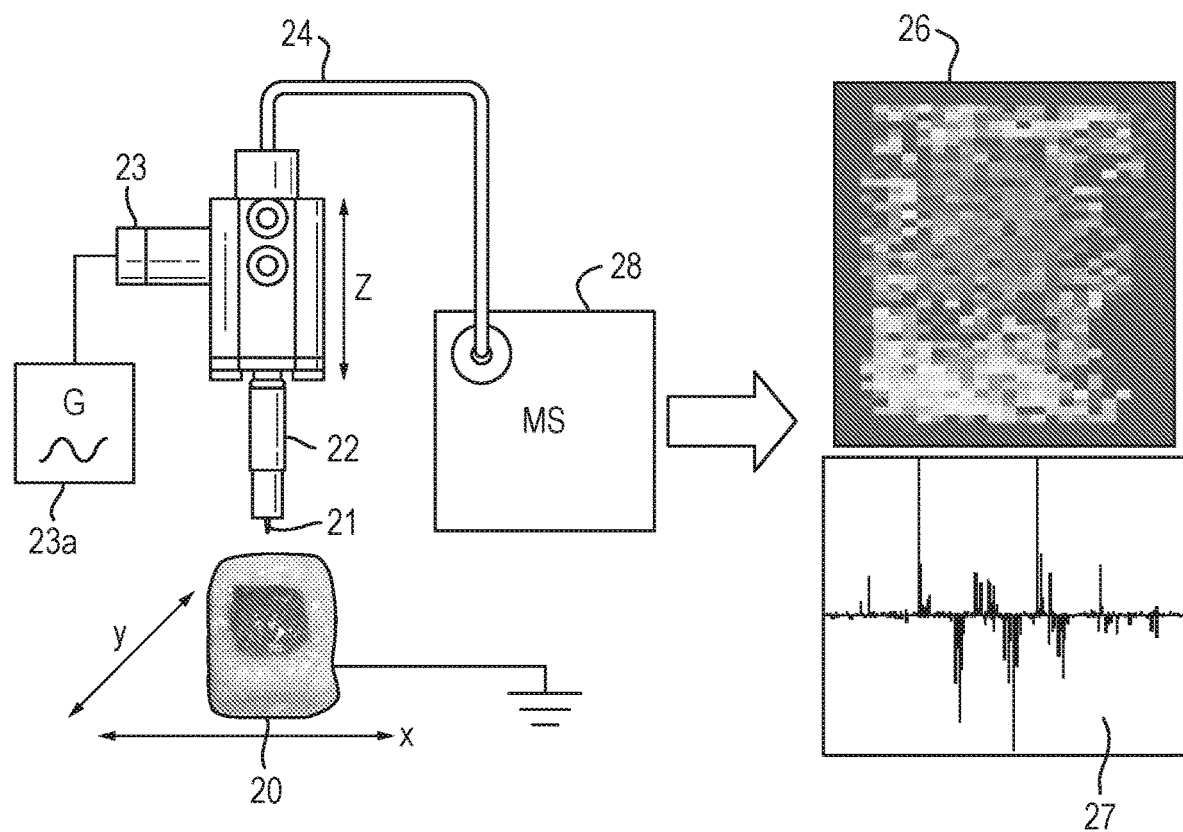
FIG. 2 shows an embodiment in which a rapid evaporative ionization mass spectrometry imaging platform is located above a tissue sample to be imaged.

FIG. 2 shows an embodiment in which a rapid evaporative ionization mass spectrometry imaging platform (i.e. an ion imager) is located above a tissue sample 20 to be imaged. The rapid evaporative ionization mass spectrometry imaging platform includes a first device which may comprise a sampling needle, electrode, tip or probe 21 that is brought into contact with a sample 20 to generate gaseous or aerosolised analyte material by the rapid evaporative ionization process (i.e. a first device arranged and adapted to generate aerosol, smoke or vapour from the sample). Power may be provided to the sampling probe 21 by a high voltage power supply 23, in conjunction with a function generator 23a. The evaporated gaseous or aerosolised analyte material may be captured by suction tubing 22 and transported (i.e. aspirated) through tubing 24 towards a mass spectrometer and/or ion mobility spectrometer 28 for analysis.

The sampling probe 21 may be mounted onto a z-actuator and may be manipulated over the sample 20 in the x-y plane to automatically sample and generate analyte material at a plurality of different locations over the whole area of the sample 20. Correlating the position of the sampling needle 21 relative to the xyz stage 25 with the results of the mass spectrometric and/or ion mobility analysis allows ion imaging of the sample 20.

Thus a plurality of different locations on the sample 20 may be automatically sampled using the first device, which is arranged and adapted to generate aerosol, smoke or vapour from the sample. By obtaining mass spectral data and/or ion mobility data corresponding to each of the locations, an ion image, such as ion image 26, may be generated.

Alternatively or additionally, the obtained mass spectral data and/or ion mobility spectrometer may be used to construct, train or improve a sample classification model. For example, the sample classification model represented by principle components analysis (PCA) loadings 27.

Figure 3:
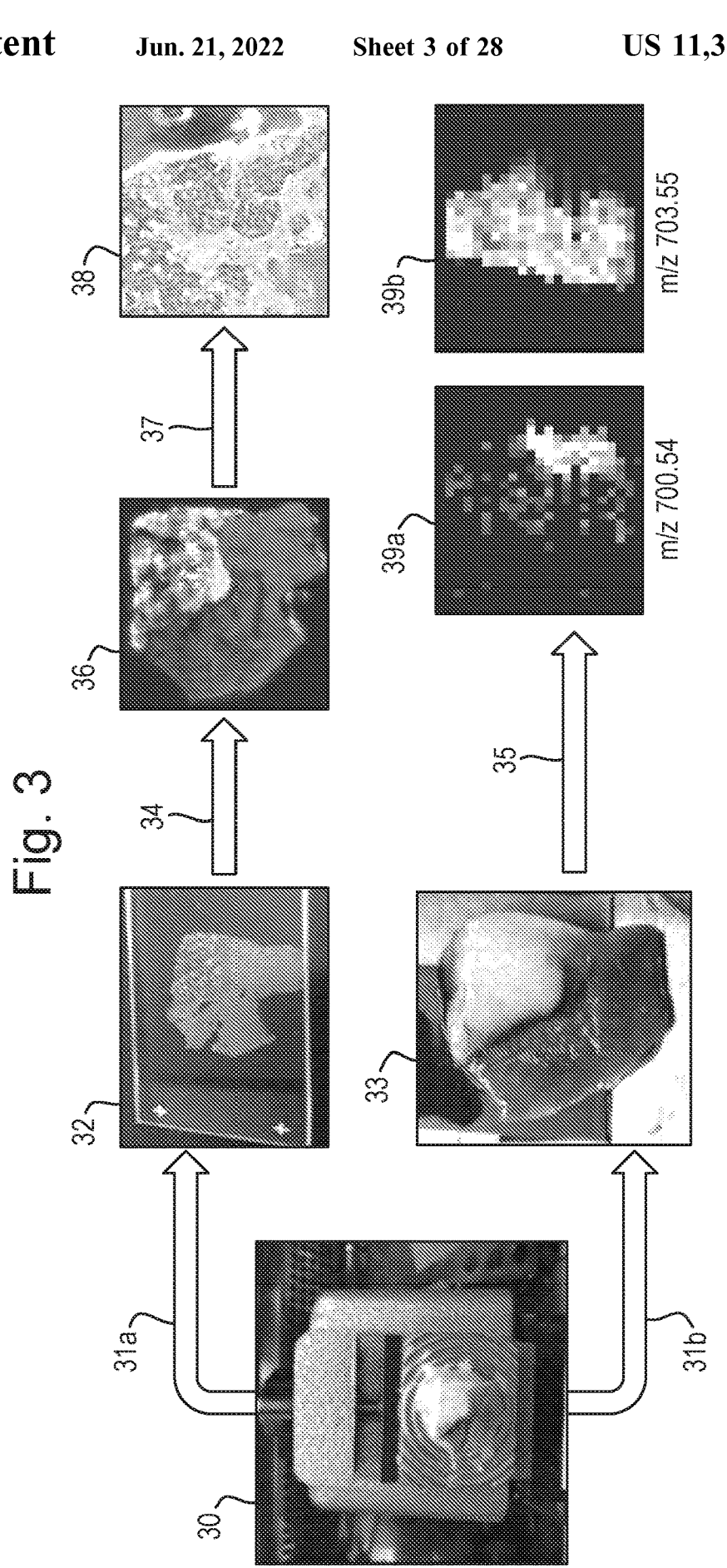
FIG. 3 shows a workflow of a combined Desorption Electrospray Ionisation ("DESI") and rapid evaporative ionization mass spectrometry imaging platform analysis for co-registration of histological features between an optical image and Desorption Electrospray Ionisation ("DESI") and rapid evaporative ionization mass spectrometry data.

FIG. 3 shows a workflow of combined Desorption Electrospray Ionization ("DESI") and rapid evaporative ionization mass spectrometry imaging platform analysis for co-registration of histological features between optical image, Desorption Electrospray Ionization ("DESI") and rapid evaporative ionization mass spectrometry data illustrating various embodiments. Fresh human liver metastasis samples were obtained from surgical resection specimens and immediately frozen to −80° C., at workflow stage 30. At stages 31a and 31b, the tissue samples were cryosectioned (Thermo Microm HM550 Cryostat, Thermo Fisher Scientific®, Germany) to 10 µm thickness and thaw mounted onto glass slides for Desorption Electrospray Ionisation ("DESI") analysis, as illustrated at workflow stage 32. The remaining bulk tissue was used for rapid evaporative ionization mass spectrometry analysis, as illustrated at stage 33.

Desorption Electrospray Ionization ("DESI") imaging analysis on the glass slide mounted tissue sample was carried out using an in-house built Desorption Electrospray Ionization ("DESI") stage at stage 34, to generate a Desorption Electrospray Ionization ("DESI") ion image illustrated at stage 36. At workflow stage 35, rapid evaporative ionization mass spectrometry imaging analysis on the bulk tissue sample was performed using a modified Prosolia® flowprobe stage (Prosolia®, USA), to generate rapid evaporative ionization mass spectrometry ion images, for example ion images illustrated at 39a and 39b.

Desorption Electrospray Ionization ("DESI") analysis of tissues was carried out using a mass spectrometer operated in negative ion mode.

The Desorption Electrospray Ionization ("DESI") imaging pixel size was set to 100 µm, the electrospray solvent was methanol:water (95:5 vol/vol) at a solvent flow rate of 1.5 µL/min and zero-grade nitrogen nebulizing gas at a pressure of 4 bar was used. Following Desorption Electrospray Ionization ("DESI") analysis, at stage 37, tissue sections were stained with H&E (haematoxylin and eosin) and digitally scanned (Nano-Zoomer 2.0-HT, Hamamatsu®, Japan) to create optical images at stage 38 for comparison with the ambient ionization mass spectral (Desorption Electrospray Ionization ("DESI") and rapid evaporative ionization mass spectrometry) images.

A line scan mode (cutting mode of operation) rapid evaporative ionization mass spectrometry analysis of one liver metastasis sample was performed on a mass spectrometer and a spot sampling (pointing mode of operation) analysis of another liver metastasis sample and a microorganism culture were performed on a Waters Xevo G2-S Q-TOF Instrument® (Waters Micromass®, U.K.) in negative ion mode.

Figure 4:
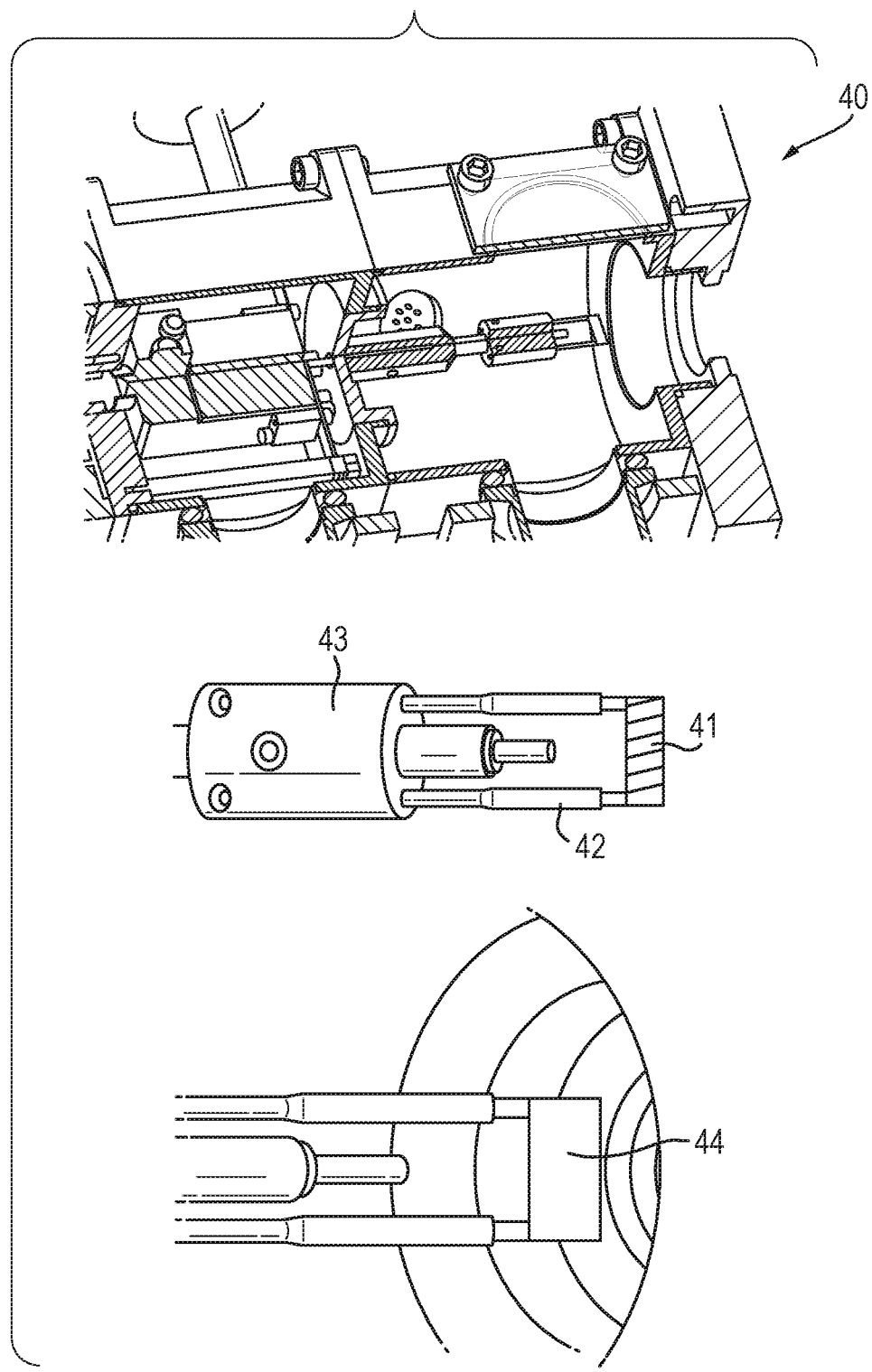
FIG. 4 shows a heated coil interface used on a Waters Xevo G2-S® instrument for improved sensitivity and robustness towards contamination.

The Waters Xevo G2-S® mass spectrometer was equipped with a modified atmospheric interface 40 combining an orthogonal Venturi-pump for aerosol transfer and a heated capillary inlet as shown in FIG. 4. The heated capillary inlet comprises a cylindrical collision surface 44 mounted within a ceramic holder 43 and heated via a sheathed 42 conductive coil 41. The use of such a heated coil interface may provide improved sensitivity and robustness against contamination.

Thus according to this embodiment, at least some aerosol, smoke or vapour generated by a first device operating in a cutting or pointing mode of operation may be caused to impact upon the heated collision surface located within the vacuum chamber of a mass spectrometer and/or ion mobility spectrometer, so as to generate analyte ions.

Rapid evaporative ionization mass spectrometry imaging analysis of liver metastasis was carried out in a (first) cutting mode at 1 bar Venturi gas pressure and about 4 kV p-p amplitude at about 50 kHz alternating current frequency (AC). A blade-shaped electrosurgical tip (sampling probe) was used, about 500 µm pixel size, 1 mm/s cutting speed and 1 mm cutting depth.

Analysis of liver metastasis in a (second) pointing mode was carried out at about 0.25 bar Venturi gas pressure, 2 kV amplitude at about 50 kHz AC and using a wire-shaped electrosurgical tip at about 750 µm pixel size, 0.1 s time remaining inside the sample and a pointing depth of about 1 mm.

Aerosol was transferred (i.e. aspirated) using a ⅛" OD, 2 mm ID PTFE tubing. Since the used power settings were sufficiently high such as potentially to cause severe injury, the instrumental setup was handled with high caution and insulating gloves were worn.

Parameter optimization of the rapid evaporative ionization mass spectrometry imaging platform was carried out using porcine liver samples. For comparison of mass spectral patterns between rapid evaporative ionization mass spectrometry imaging and iKnife technology, porcine liver, porcine kidney cortex, lamb liver and chicken skeletal muscle were analysed using an electrosurgical handpiece (Meyer-Haake GmbH®, Germany) with incorporated PTFE tubing (⅛" OD, 2 mm ID) which was connected to the Venturi pump. Liver, kidney and muscle were food grade and purchased as such. The iKnife technology was operated in a cutting mode at 40 W and 1 bar gas pressure in combination with a Valleylab SurgiStat II® power-controlled electrosurgical generator (Covidien, Ireland).

Data Processing

Raw spectral profiles were loaded into a MATLAB® environment (Version R2014a, Mathworks, USA) for pre-processing, MS-image visualization and pattern recognition analysis. All mass spectra were linearly interpolated to a common interval of 0.1 Da and individually normalized to the total ion count ("TIC") of each mass spectrum. The data was used for univariate comparison of intensity levels across liver tissue types and ionization techniques and for bacterial MS-image visualization of single ions. Peak annotation for liver metastasis samples was based on m/z accuracy obtained from the unprocessed raw files, while bacterial peak annotation was based on mass accuracy and on tandem-MS spectra obtained using bipolar forceps.

Multivariate MS-image visualization was performed on mass spectra additionally binned to 1 Da intervals in the mass range of m/z 600-1000 Da for biological tissue and m/z 400-2000 for bacteria. For multivariate image visualization, MS-images and optical images were co-registered to define regions of interest ("ROIs") for building a supervised training model (i.e. a sample classification model). Defined ROIs (classes) were healthy and cancerous tissue for the liver samples and one region for each bacterium plus agar, resulting overall in two classes for liver samples and four classes for bacterial samples.

The training model was used to classify each pixel of the same sample and colour code the obtained score-values into red-green-blue colour scale. This supervised strategy for image visualization is based on an algorithm that combines recursive maximum margin criterion ("RMMC") with linear discriminant analysis ("LDA"). For unsupervised analysis, principal component analysis ("PCA") was performed on the mass spectra defined by the regions of interest.

Concordance correlation coefficients were used to measure the agreement between rapid evaporative ionization mass spectrometry imaging platform ("RIP") mass spectra and iKnife technology mass spectra. This quantitative measure is defined as:

$$\rho_c = \frac{2\rho\sigma_{RIP}\sigma_{iKnife}}{\sigma_{RIP}^2 + \sigma_{iKnife}^2 + (\mu_{RIP} - \mu_{iKnife})^2} \quad (1)$$

wherein $\rho_c$ is the concordance correlation coefficient, $\rho$ is Pearson's correlation coefficient and $\sigma_{RIP/iKnife}$ is the standard deviation of the mean intensity values of $\mu_{RIP/iKnife}$.

A low concordance correlation coefficient close to the value of zero indicates low agreement while a value close to the value of one suggests high similarity between spectral profiles.

Boxplots show the median at the central mark within the box with $25^{th}$ and $75^{th}$ percentiles at the edges of the box. The upper and lower whiskers account for approximately 2.7 standard deviations (99.3% data coverage). Mass spectra were standardized to 100% intensity scale before their data was visualized with boxplots.

Analysing Sample Spectra

A list of analysis techniques which are intended to fall within the scope of the present invention are given in the following Table 2:

TABLE 2

A list of analysis techniques.
Analysis Techniques

Univariate Analysis
Multivariate Analysis
Principal Component Analysis (PCA)
Linear Discriminant Analysis (LDA)
Maximum Margin Criteria (MMC)
Library Based Analysis
Soft Independent Modelling Of Class Analogy (SIMCA)
Factor Analysis (FA)
Recursive Partitioning (Decision Trees)
Random Forests
Independent Component Analysis (ICA)
Partial Least Squares Discriminant Analysis (PLS-DA)
Orthogonal (Partial Least Squares) Projections To Latent Structures (OPLS)
OPLS Discriminant Analysis (OPLS-DA)
Support Vector Machines (SVM)
(Artificial) Neural Networks
Multilayer Perceptron
Radial Basis Function (RBF) Networks
Bayesian Analysis
Cluster Analysis
Kernelized Methods
Subspace Discriminant Analysis
K-Nearest Neighbours (KNN)
Quadratic Discriminant Analysis (QDA)
Probabilistic Principal Component Analysis (PPCA)
Non negative matrix factorisation
K-means factorisation
Fuzzy c-means factorisation
Discriminant Analysis (DA)

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

According to various embodiments, obtained mass spectral data and/or ion mobility data is used to construct, train or improve a sample classification model. By way of example, a method of building a classification model using multivariate analysis of plural reference sample spectra will now be described.

Figure 5:
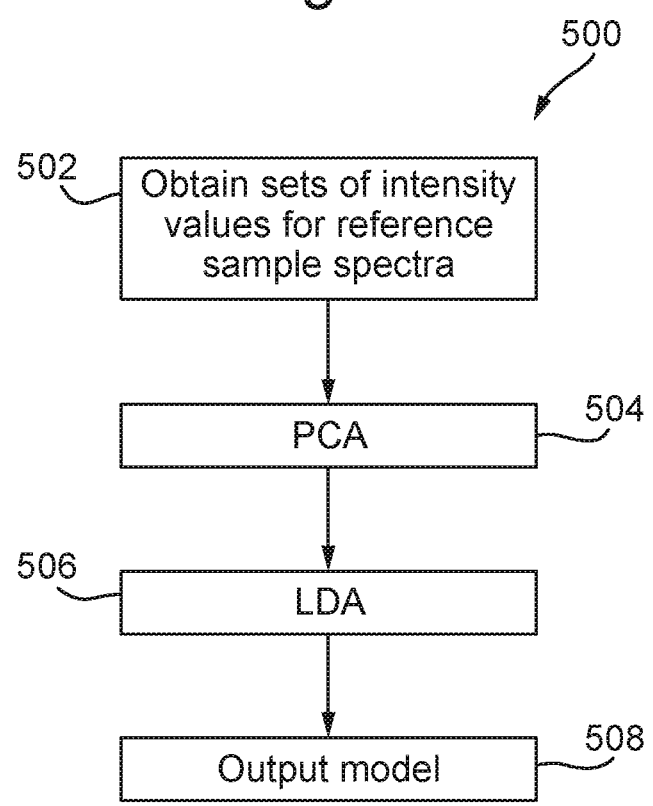
FIG. 5 shows a method of analysis that comprises building a classification model according to various embodiments.

FIG. 5 shows a method 500 of building a classification model using multivariate analysis according to an embodiment. In this example, the method comprises a step 502 of obtaining plural sets of intensity values for reference sample spectra. The method then comprises a step 504 of unsupervised principal component analysis (PCA) followed by a step 506 of supervised linear discriminant analysis (LDA). This approach may be referred to herein as PCA-LDA. Other multivariate analysis approaches may be used, such as PCA-MMC. The PCA-LDA model is then output, for example to storage, in step 508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 6:
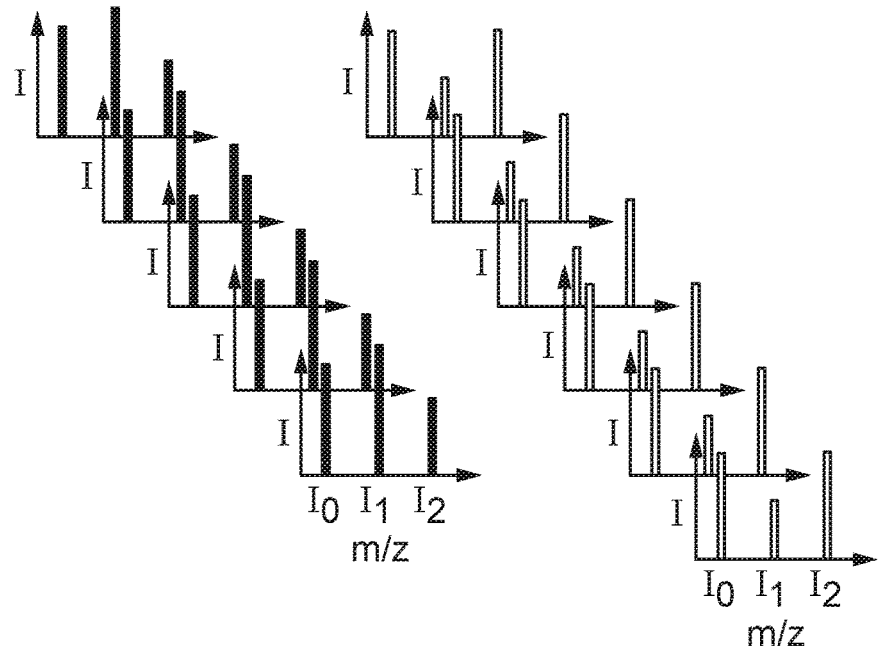
FIG. 6 shows a set of reference sample spectra obtained from two classes of known reference samples.

FIG. 6 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 7:
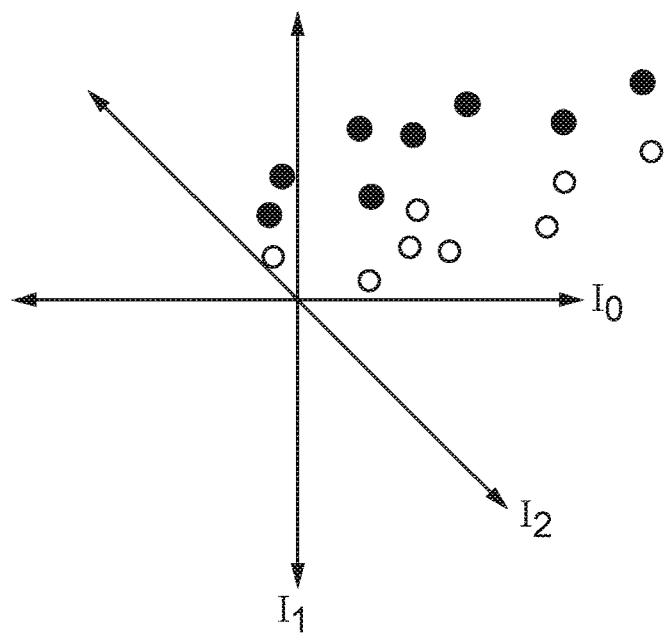
FIG. 7 shows a multivariate space having three dimensions defined by intensity axes, wherein the multivariate space comprises plural reference points, each reference point corresponding to a set of three peak intensity values derived from a reference sample spectrum.

FIG. 7 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 8:
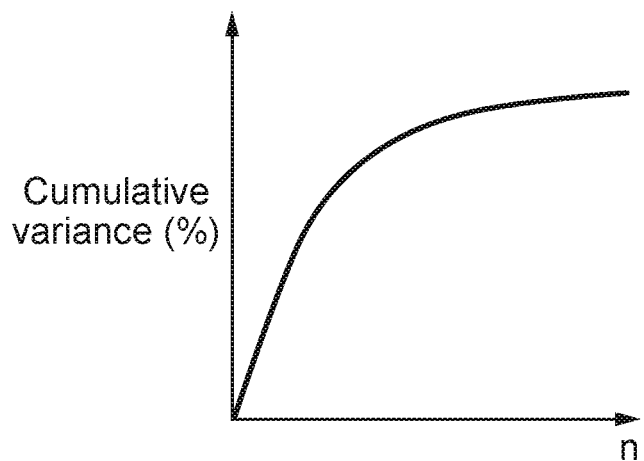
FIG. 8 shows a general relationship between cumulative variance and number of components of a PCA model.

FIG. 8 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \qquad (2)$$

Figure 9:
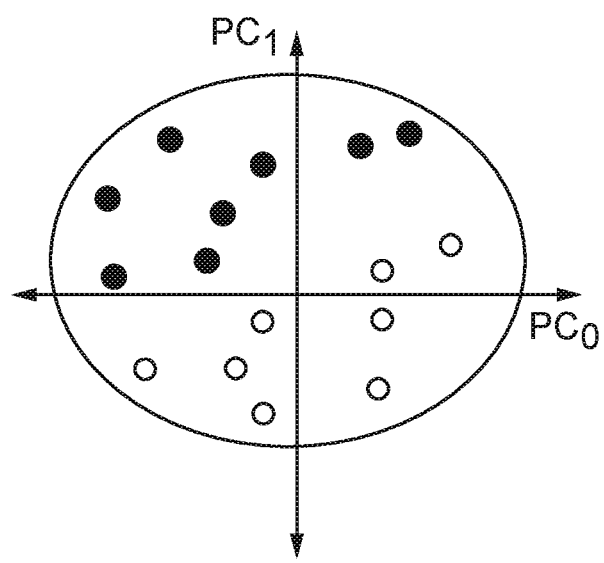
FIG. 9 shows a PCA space having two dimensions defined by principal component axes, wherein the PCA space comprises plural transformed reference points or scores, each transformed reference point or score corresponding to a reference point of FIG. 7.

FIG. 9 shows the resultant PCA space for the reference sample spectra of FIGS. 6 and 7. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 6 and therefore to a reference point of FIG. 7.

As is shown in FIG. 9, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail. The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \qquad (3)$$

where the matrix Z contains the scores transformed into the LDA space.

Figure 10:
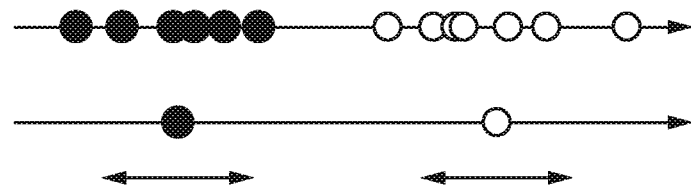
FIG. 10 shows a PCA-LDA space having a single dimension or axis, wherein the LDA is performed based on the PCA space of FIG. 9, the PCA-LDA space comprising plural further transformed reference points or class scores, each further transformed reference point or class score corresponding to a transformed reference point or score of FIG. 9.

FIG. 10 shows a PCA-LDA space having a single dimension or axis, wherein the LDA is performed in the PCA space of FIG. 9. As is shown in FIG. 10, the LDA space comprises plural further transformed reference points or PCA-LDA scores, with each further transformed reference point corresponding to a transformed reference point or PCA score of FIG. 9.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by:

$$V'_g = U^T V_g U \qquad (4)$$

where $V_g$ are the class covariance matrices in the PCA space.

The transformed class average position $z_g$ for class g may be given by:

$$s_g U = z_g \qquad (5)$$

where $s_g$ is the class average position in the PCA space.

Multivariate Analysis—Using a Model for Classification

According to various embodiments, a sample classification model which was previously constructed, trained or improved according to a method described herein is used in order to classify a sample at a location. By way of example, a method of using a classification model to classify an aerosol, smoke or vapour sample will now be described.

Figure 11:
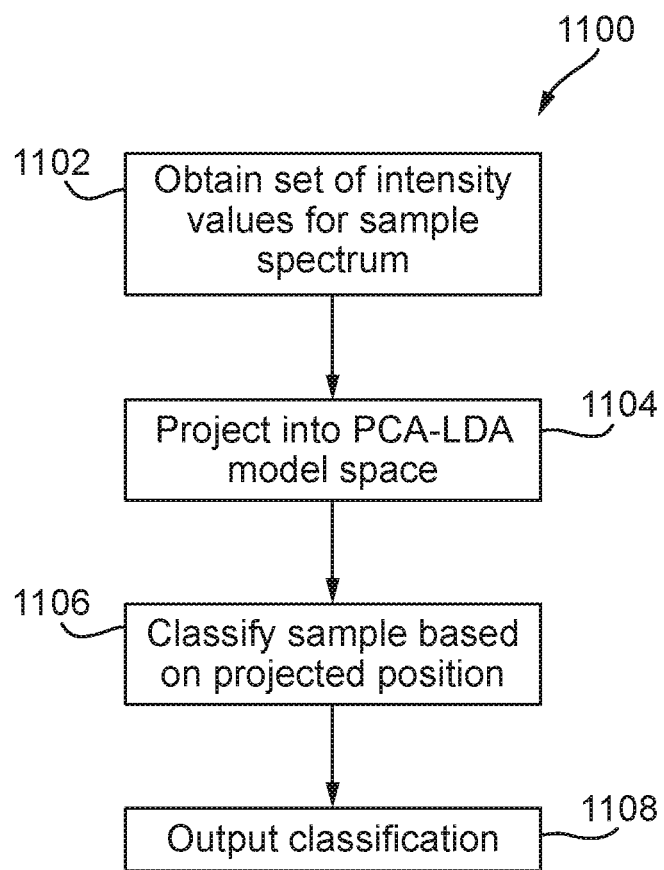
FIG. 11 shows a method of analysis that comprises using a classification model according to various embodiments.

FIG. 11 shows a method 1100 of using a classification model according to an embodiment. In this example, the method comprises a step 1102 of obtaining a set of intensity values for a sample spectrum. The method then comprises a step 1104 of projecting the set of intensity values for the sample spectrum into PCA-LDA model space. Other classification model spaces may be used, such as PCA-MMC. The sample spectrum is then classified at step 1106 based on the project position and the classification is then output in step 1108.

Classification of an aerosol, smoke or vapour sample will now be described in more detail with reference to the simple PCA-LDA model described above.

Figure 12:
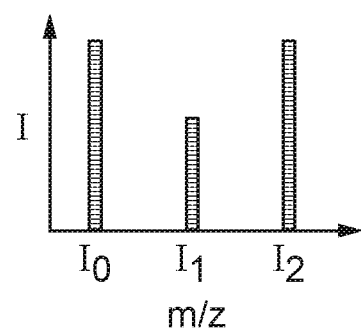
FIG. 12 shows a sample spectrum obtained from an unknown sample.

FIG. 12 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \qquad (6)$$

Then, a transformed PCA-LDA vector $z_x$ for the sample spectrum can be obtained as follows:

$$s_x U = z_x \qquad (7)$$

Figure 13:
FIG. 13 shows the PCA-LDA space of FIG. 10, wherein the PCA-LDA space further comprises a PCA-LDA projected sample point derived from the peak intensity values of the sample spectrum of FIG. 12

FIG. 13 again shows the PCA-LDA space of FIG. 10. However, the PCA-LDA space of FIG. 13 further comprises the projected sample point, corresponding to the transformed PCA-LDA vector $z_x$, derived from the peak intensity values of the sample spectrum of FIG. 12.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \qquad (8)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

Figure 14:
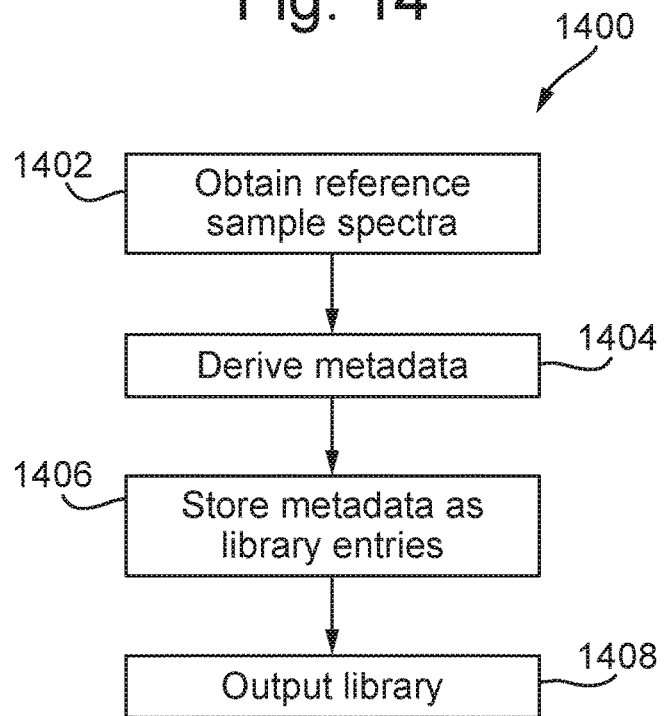
FIG. 14 shows a method of analysis that comprises building a classification library according to various embodiments.

FIG. 14 shows a method 1400 of building a classification library. In this example, the method comprises a step 1402 of obtaining plural input reference sample spectra and a step 1404 of deriving metadata from the plural input reference sample spectra for each class of sample. The method then comprises a step 1404 of storing the metadata for each class of sample as a separate library entry. The classification library is then output, for example to electronic storage, in step 1406.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \middle/ \log \frac{M_{max}}{M_{min}} \right\rfloor$$

where $N_{chan}$ is a selected value and $\lfloor x \rfloor$ denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5.

A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\vec{y}_i$. In one example, $\vec{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i \mid \mu_i, D_i) = \frac{1}{D_i} \frac{C^{C-1/2} \Gamma(C)}{\sqrt{\pi} \Gamma(C - 1/2)} \frac{1}{\left(C + \frac{(y_i - \mu_i)^2}{D_i^2}\right)^C}$$

where $1/2 \leq C < \infty$ and where $\Gamma(C)$ is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i \mid \mu_i, D_i) = \frac{3}{4} \frac{1}{D_i} \frac{1}{(3/2 + (y_i - \mu_i)^2 / D_i^2)^{3/2}}$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library Based Analysis—Using a Library for Classification

By way of example, a method of using a classification library to classify an aerosol, smoke or vapour sample will now be described.

Figure 15:
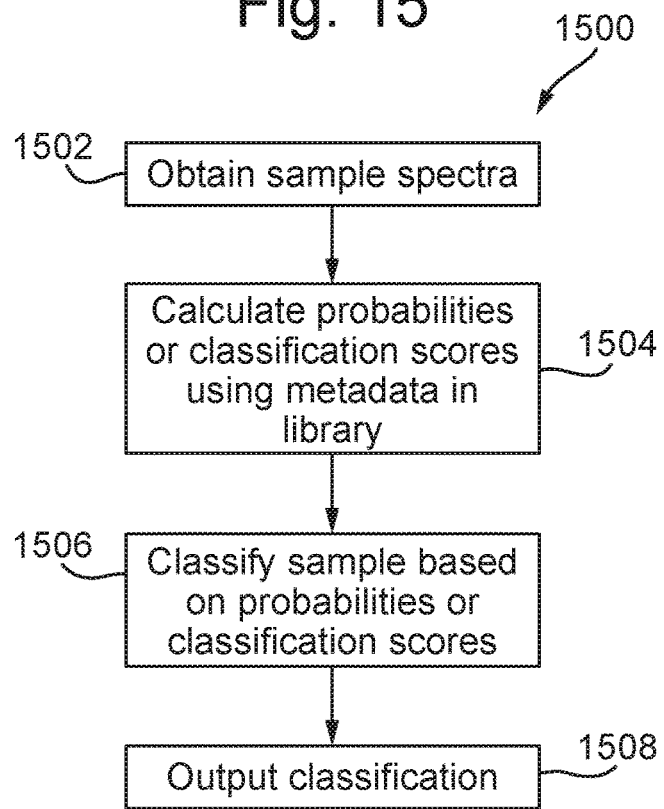
FIG. 15 shows a method of analysis that comprises using a classification library according to various embodiments.

FIG. 15 shows a method 1500 of using a classification library. In this example, the method comprises a step 1502 of obtaining a set of plural sample spectra. The method then comprises a step 1504 of calculating a probability or classification score for the set of plural sample spectra for each class of sample using metadata for the class entry in the classification library. The sample spectra are then classified at step 1506 and the classification is then output in step 1508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y \mid \mu, D) = \prod_{i=1}^{N_{chan}} Pr(y_i \mid \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s} \mid y) = \frac{L_{\tilde{s}}^{(1/F)}}{\sum_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Rapid Evaporative Ionization Mass Spectrometry Imaging Platform

Figure 16:
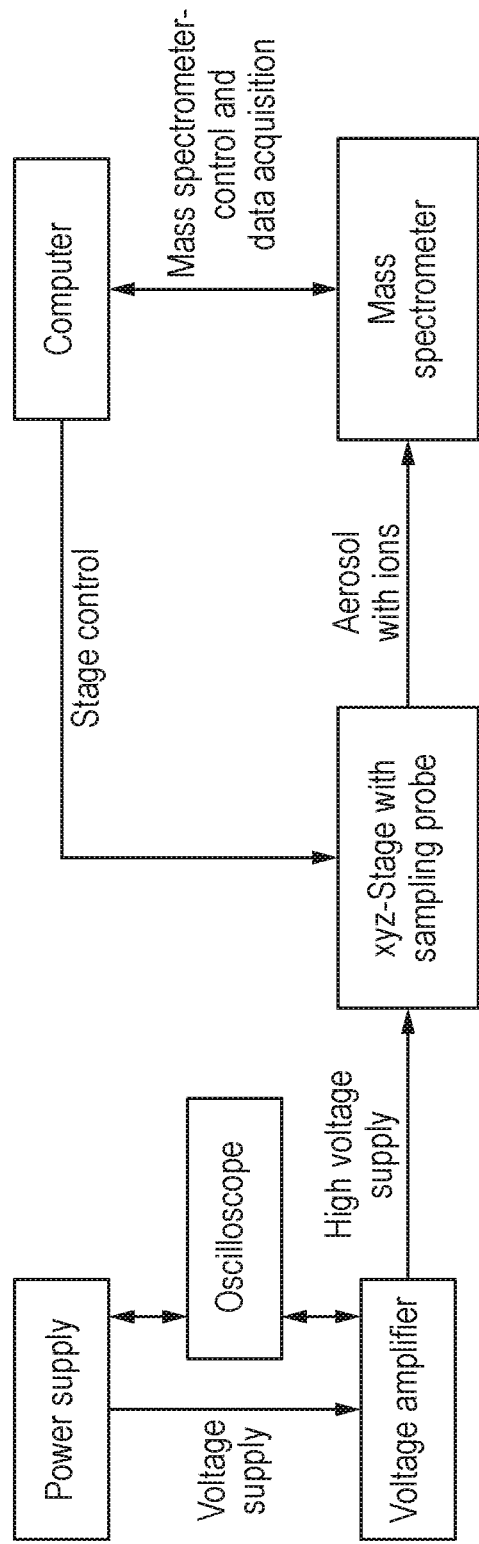
FIG. 16 schematically illustrates a setup of rapid evaporative ionization mass spectrometry imaging instrumentation.
Figure 17A:
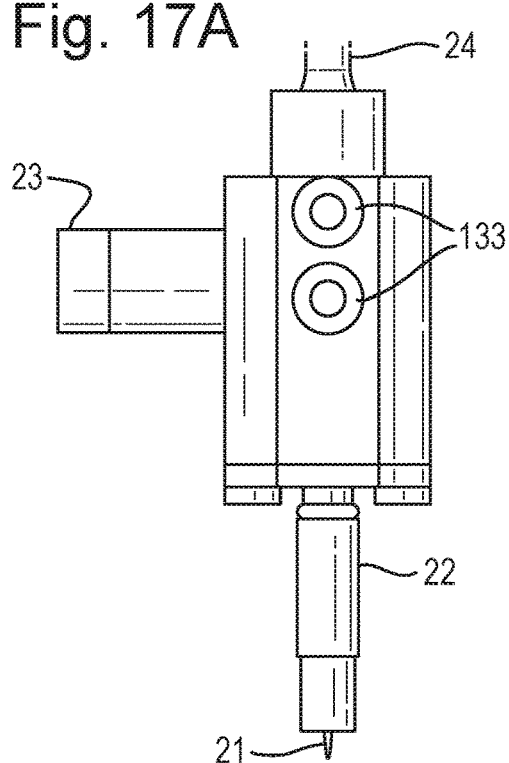
FIG. 17A shows a rapid evaporative ionization mass spectrometry imaging sampling probe.
Figure 17B:
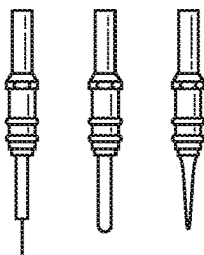
FIG. 17B shows a variety of possible alternatively shaped sampling probes and FIG. 17C shows a setup of a xyz-stage wherein the sampling probe is mounted onto a z-actuator and is connected to a high voltage power supply and wherein evaporated aerosol is captured by suction tubing and is transported to a mass spectrometer according to an embodiment.
Figure 17C:
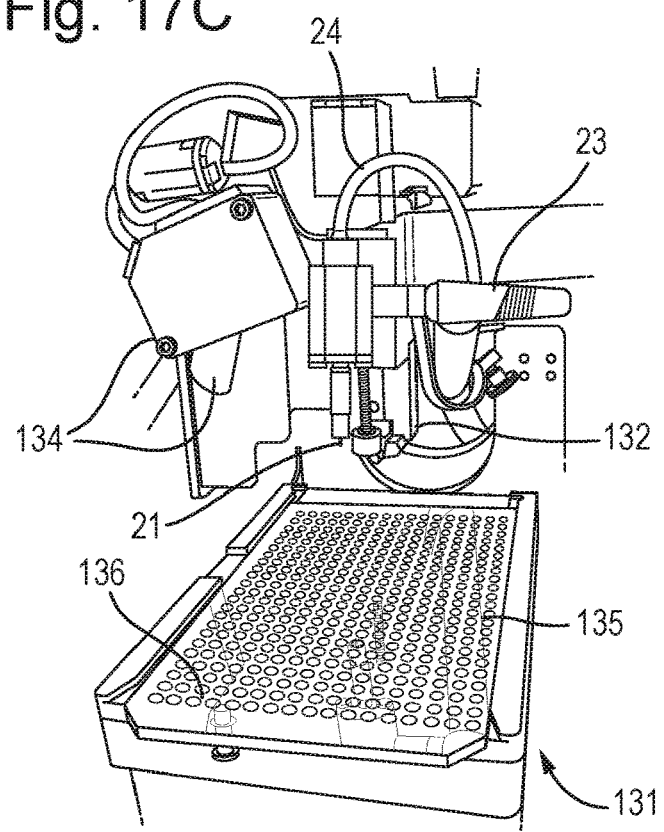

FIG. 16 schematically illustrates and FIGS. 17A-C show a rapid evaporative ionization mass spectrometry imaging platform (i.e. an ion imager) in accordance with an embodiment, which includes three major functional elements that all influence the quality of mass spectra. The imaging platform may include a power generator, a xyz-stage with a sampling probe (i.e. a first device arranged and adapted to generate aerosol, smoke or vapour from a sample) and a mass spectrometer and/or ion mobility spectrometer.

According to an embodiment, the mass spectral data and/or ion mobility data obtained using the rapid evaporative ionization mass spectrometry (or other ambient ionisation) imaging platform may be used to construct, train or improve a sample classification model (e.g., as described above).

The power supply setup used for the platform may comprise a Tektronix® AFG 3022 arbitrary function generator (Tektronix®, USA), a Tektronix® DPO 3014 Oscilloscope and a Trek 10/40A High Voltage Amplifier (Trek®, USA).

The arbitrary function generator was used to generate sinus waveforms with amplitudes between 1 V and 6 V at frequencies in the range of 10 to 60 kHz. The high voltage power amplifier multiplied the voltage by a factor of 1000 and supplied the connected sampling probe with the electric current. The oscilloscope provided feedback to ensure correct working parameters.

The xyz-stage may comprise a modified Prosolia® 2D Desorption Electrospray Ionization ("DESI") stage 131 (as shown in FIG. 17C) and may include a Flowprobe® upgrade (Prosolia®, USA) with a high precision z-axis actuator 132. The sampling probe 21 is mounted onto the actuator 132 via two mounting points 133 and is connected to the power generator setup 23 as well as a MS inlet capillary through tubing 24 (as shown in FIG. 17A).

A laser height sensor 134 may be used to measure the distance or height between an electrosurgical tip of the sampling probe 21 (or more generally the first device) and the sample surface, and can ensure an equal penetration depth of the tip into the sample which is useful for uneven sample surfaces. The laser height sensor 134 may comprise a camera. The electrosurgical tip of the sampling probe 21 may be exchanged for other materials or shapes depending on the field of application. In case of high precision sampling, a small diameter wire may be used, whereas a large surface tip is suitable to maximize mass spectrometric and/or ion mobility signal intensity. A variety of possible alternatively shaped sample probes are shown in FIG. 17B. The electrosurgical tip may be surrounded by suction tubing 22 which is connected to a Venturi air jet pump.

Other embodiments are contemplated wherein other ambient ionisation ion sources may be used and/or an optical fibre in conjunction with a laser source may be used to generate aerosol, smoke or vapour from a target (e.g. tissue sample).

Figure 18A:
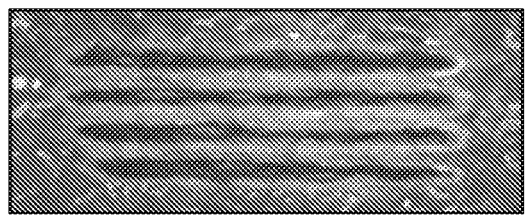
FIG. 18A shows a cutting sampling mode of the rapid evaporative ionization mass spectrometry imaging platform according to an embodiment and FIG. 18B shows a pointing sampling mode of the rapid evaporative ionization mass spectrometry imaging platform according to another embodiment.
Figure 18B:
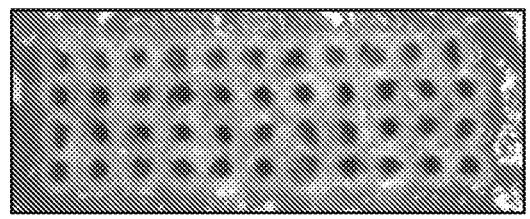

The imaging platform is capable of at least two sampling modes; namely a cutting mode of operation as illustrated in FIG. 18A and a pointing mode of operation as illustrated in FIG. 18B. In a cutting mode of operation, line scans are performed and the electrosurgical tip of the sampling probe 21 may be kept at a constant z-value, i.e. a constant height above the sample, while the x and y values can change in a way such that a macroscopic cut is made in a right to left trajectory through the tissue sample, with each subsequent cut being made at an increment further in the y direction. In this approach, the electrosurgical tip is in substantially continuous contact with the sample and therefore continuously produces aerosol.

Figure 19C:
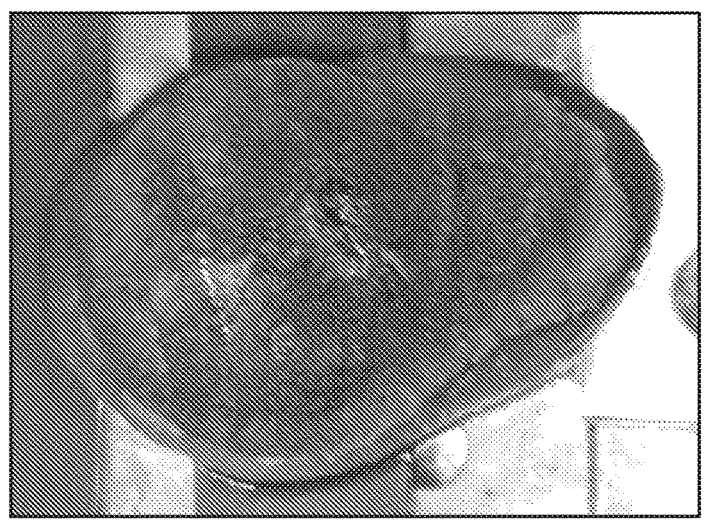
FIG. 19C shows how rapid evaporative ionization mass spectrometry imaging in cutting mode at low spatial resolution evaporates the top surface layer of the sample.
Figure 19B:
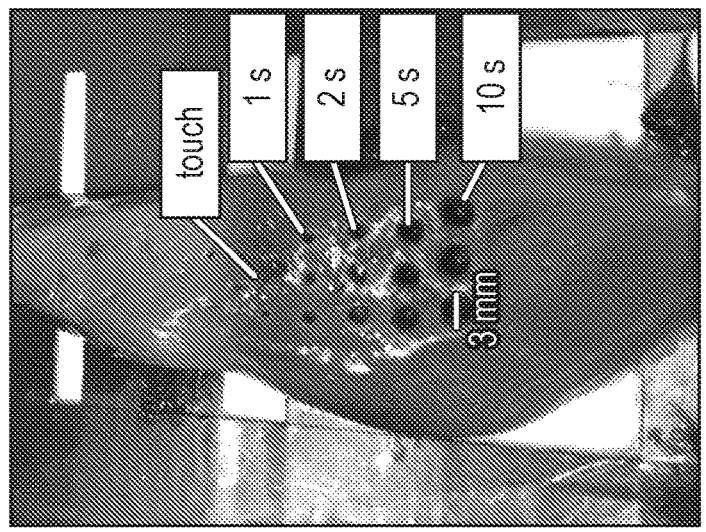
FIG. 19B shows the impact on carbonization, burning-valley and crater size for the time the electrosurgical tip remained inside the sample for a pointing mode of operation
Figure 19A:
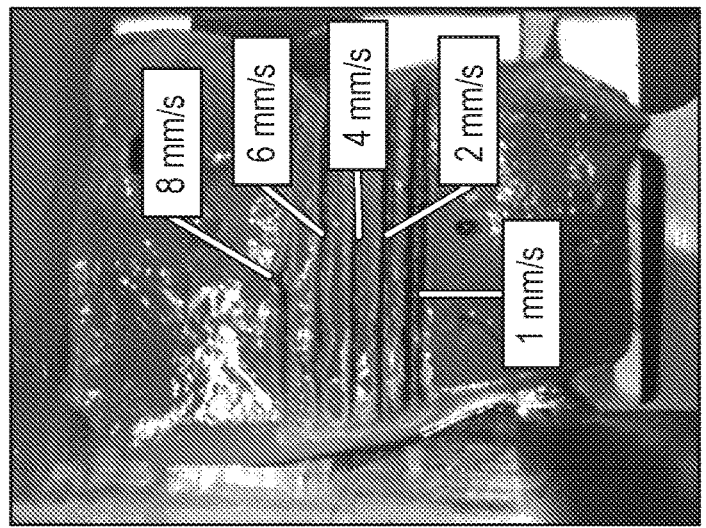
FIG. 19A shows the impact on carbonization, burning-valley and crater size for various cutting speeds in a cutting mode of operation.

The speed of x-movement influences the width of the region of tissue disruption and the amount of aerosol produced (as illustrated in FIG. 19A). If the step size in the y direction is smaller than the burning-valley-width, then a complete surface layer will be evaporated (as illustrated in FIG. 19C).

In a pointing mode of operation, the sampling probe 21 can penetrate the sample for a given depth and time. Both factors influence the amount of evaporated aerosol and burn-crater size as is apparent from FIG. 19B.

In terms of imaging performance, the time of contact between the electrosurgical tip and the sample can influence the achievable spatial resolution which is limited by the width of tissue disruption. As ion current is also a function of cutting speed, there is (like in the case of all other MSI methods) a trade-off between spatial resolution, signal intensity and sampling time. In a cutting mode of operation, the speed of imaging depends on a user defined cutting speed which is usually the already mentioned compromise between mass spectrometer and/or ion mobility spectrometer sampling time and desired spatial resolution.

In the case of a pointing mode of operation, the time necessary to move from one sampling spot or location to the next may be determined by the maximum movement speed of the xyz-stage and the time the sampling probe tip remains inside the sample. An exemplary cutting speed is about 1 mm/s, and the time necessary to record one pixel in a pointing mode of operation may be about 3 s, for example. Using these parameters, imaging of a 2×2 cm sample with 2 mm spatial resolution will take an approximately equal amount of time of about 5 minutes for both pointing and cutting modes of operation (see Table 3 below). The additional time necessary to move the z-actuator in the pointing mode of operation becomes more significant as the pixel size becomes smaller. This leads to a five times higher amount of imaging time at 500 μm pixel size in a pointing mode of operation compared with a cutting mode of operation.

While cutting mode imaging at low resolutions evaporates the whole top sample layer, pointing mode in low resolution leaves the majority of tissue unaffected, allowing the same surface to be characterized at a later time.

In both cases, the user of a preferred rapid evaporative ionization mass spectrometry imaging platform (i.e. ion imager) should be aware of the heterogeneity within the sample, as cutting and pointing depth causes tissue evaporation from the bulk sample.

TABLE 3

Theoretical sampling time and resolution for 2 × 2 cm sample. Cutting mode sampling at 1 mm/s cutting speed and 25 s per row, which includes return time to a new row. Pointing mode sampling at 3 s per pixel.

| Pixel Size | No. of Pixels | Pointing Mode Time/min | Cutting Mode No. of Rows | MS scan time/s | Time/min |
|---|---|---|---|---|---|
| 2 mm | 100 | 5 | 10 | 2 | 4.2 |
| 1 mm | 400 | 20 | 20 | 1 | 8.3 |
| 500 μm | 1600 | 80 | 40 | 0.5 | 16.7 |
| 250 μm | 6400 | 320 | 80 | 0.25 | 33.3 |

The transfer (i.e. aspiration) of aerosol to the mass spectrometer and/or ion mobility spectrometer may be carried out using a Venturi air jet pump mounted to an atmospheric interface of a mass spectrometer and/or ion mobility spectrometer. The aerosol trajectory may be perpendicular to the MS-inlet capillary. As a result, larger particles may be excluded by momentum separation thereby avoiding clogging and contamination of the mass spectrometer and/or ion mobility spectrometer. Excess aerosol may be captured by a surgical smoke trap device.

Frequency and Voltage Dependencies

The imaging platform (i.e. ion imager) can enable automated high-throughput collection of reference mass spectra and/or ion mobility data in order to aid real-time classification in MS-guided electrosurgery (iKnife technology) applications. For example, according to an embodiment, the classification algorithm (i.e. sample classification model) may compare mass spectral and/or ion mobility patterns of spectra created during surgery with mass spectra obtained ex vivo, in vivo or in vitro. Accordingly, it is important that the rapid evaporative ionization mass spectrometry imaging platform provides similar ionization conditions as will be used in surgery.

Thus, according to this embodiment, a plurality of different locations of a sample are sampled using a first device arranged and adapted to generate aerosol, smoke or vapour from the sample to obtain mass spectral data and/or ion mobility data at each location. A sample classification model which was previously constructed, trained or improved according to a method of ion imaging as described herein is then used in order to classify the sample at each location.

Commercially available electrosurgical generators as used in operating theatres provide highly reproducible mass spectral patterns which are unique for different histological tissue types. The power supply setup used in conjunction with the imaging platform (as shown schematically illustrated in FIG. 16) may allow variation in the amplitude and/or frequency and/or waveform, while an oscilloscope may provide feedback ensuring correct working conditions. Depending on the application of the imaging platform, the experimental parameters can thus be changed in order to alter ionization conditions and to meet the requirements for recording reference mass spectra for intra-surgical tissue identification or bacterial classification purposes.

Rapid evaporative ionization mass spectrometry ionization mechanism is based on Joule-heating which is a thermal process wherein the heat created is proportional to the square of electric current and the impedance. As electric current density is also a function of cross sectional area, the contact surface area of the electrosurgical tip of the sampling probe 21 also has an impact on the heating process.

If an electric current is applied to a biological tissue then the intracellular temperature rises up to a point of vaporization where excess heat facilitates evaporation of particles and ions leading to the formation of surgical aerosol. The major ions created in this process are singly charged lipids being most abundant in the m/z 600-1000 mass range for eukaryotic tissue and additionally in the m/z 1100-1500 mass range in case of bacteria in form of e.g. lipid dimers or cardiolipins.

Depending on the thermal stability of the molecules, thermal degradation may occur as it was observed in the case of phosphatidyl-ethanolamine species which are partly ionized to both $[M-NH_4]^-$ and $[M-H]^-$, while other phospholipids species form $[M-H]^-$ ions. The density and frequency of the electric current can therefore have an important influence on the appearance of the mass spectrum.

Electrosurgical generators have an incorporated control loop providing constant power when cutting through tissue, even if the impedance is rapidly changing. This leads to gentle and reproducible cuts with minimized tissue heat exposure. Electrosurgical generators are not easily incorporated into an imaging set up due to a number of safety measures required when used in theatre, hence a simplified power supply was built. Since a p-p voltage amplitude-controlled RF power supply cannot follow the changing impedance of the sample, it was important to determine whether the simplified setup can provide spectra similar to those obtained when using proper electrosurgical equipment.

Optimization of the rapid evaporative ionization mass spectrometry imaging platform was carried out by finding the optimal frequency and voltage values to match the iKnife technology reference mass spectral pattern of porcine liver as shown in FIGS. 20A-B and FIGS. 21A-B. Concordance correlation coefficients ("CCC") between the rapid evaporative ionization mass spectrometry imaging and iKnife technology mass spectra were used as a quantitative measure to find the optimal spectral agreement.

In cutting mode, a factor influencing tissue heat exposure is cutting speed, which leads to high localized temperature for slow speeds and vice versa. Depending on the required ion current, the MS sampling time window needs to be sufficiently long, compromising either spatial resolution or cutting speeds. Therefore, prior to voltage and frequency optimization, a cutting speed should be chosen that satisfies requirements on ion yield and spatial resolution. Once a cutting speed is set, heat exposure can then be controlled by changing the voltage or frequency output of the power generator setup. The cutting speed may need further reiteration if the available range of voltages and frequencies is not sufficient for adequate heat production. An exemplary cutting speed of 1 mm/s was found to gently cut at high ion yields.

Figure 20A:
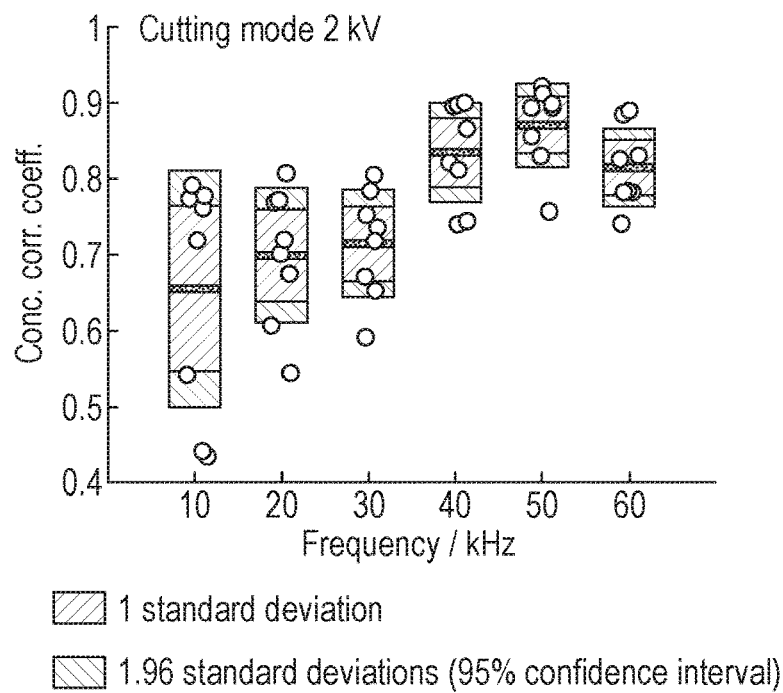
FIG. 20A shows concordance correlation coefficients (CCC) between rapid evaporative ionization mass spectrometry imaging in a cutting mode of operation and iKnife technology mass spectra in dependency on varying frequency at 2 kV for porcine liver and FIG. 20B shows concordance correlation coefficients (CCC) between rapid evaporative ionization mass spectrometry imaging in a cutting mode of operation and iKnife technology mass spectra in dependency on varying voltage at 40 kHz for porcine liver.

As shown in FIG. 20A, at a constant p-p voltage of 2 kV an increase in frequency leads to less thermal degradation and higher similarity to iKnife technology patterns. According to the oscilloscope readout, the power generator setup was not capable of maintaining a constant increase in power output above 50 kHz at a 2 kV amplitude, explaining the stable concordance correlation coefficient between about 40 kHz and about 60 kHz. At lower frequencies more in-depth heat dissipation was observed leading to wide burning valleys, carbonization and inconsistent mass spectral patterns with varying baseline noise levels. This was accompanied by strong soot particle production leading to contamination of the MS-inlet capillary, without contributing to the ion yield (see the total ion counts in FIG. 21A).

At higher frequencies (above about 40 kHz) visible soot particle production was negligible and no carbonization was observed. This led to mass spectral patterns very similar to those produced by electrosurgical equipment, as indicated by concordance correlation coefficients near 0.9. The highest and most consistent TIC was also found to be in that frequency window.

Figure 20B:
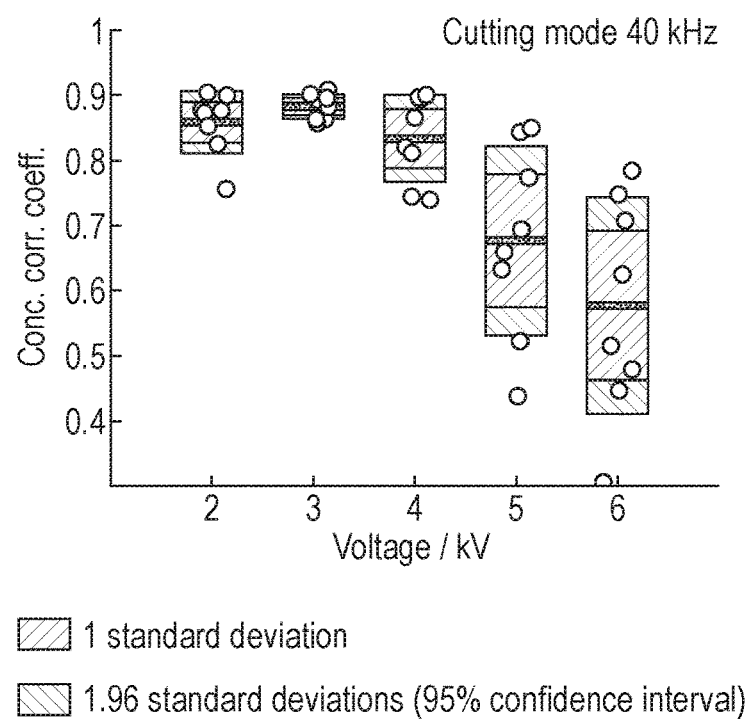
Figure 21A:
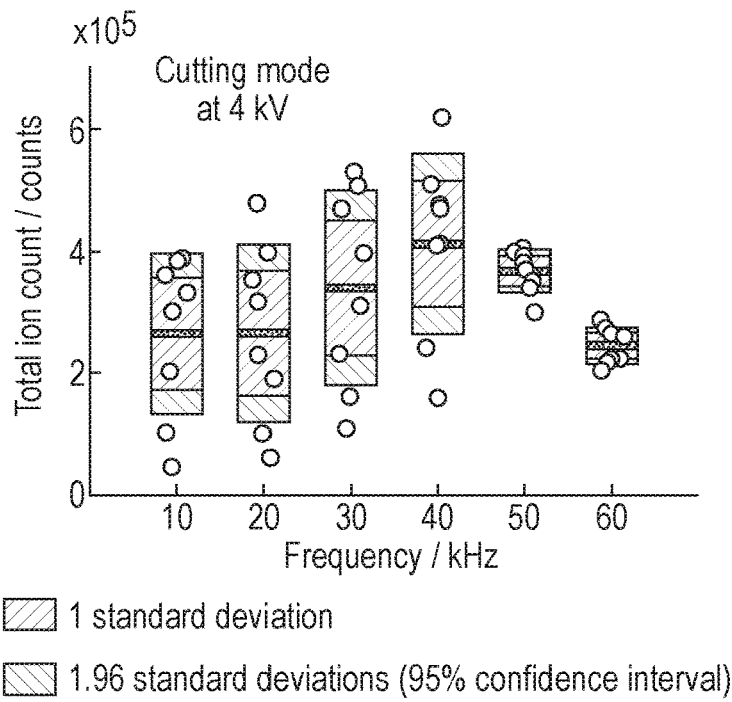
FIG. 21A shows total ion counts (TIC) at different frequencies in a cutting mode of operation and FIG. 21B shows total ion counts (TIC) at different voltages in a cutting mode of operation.
Figure 21B:
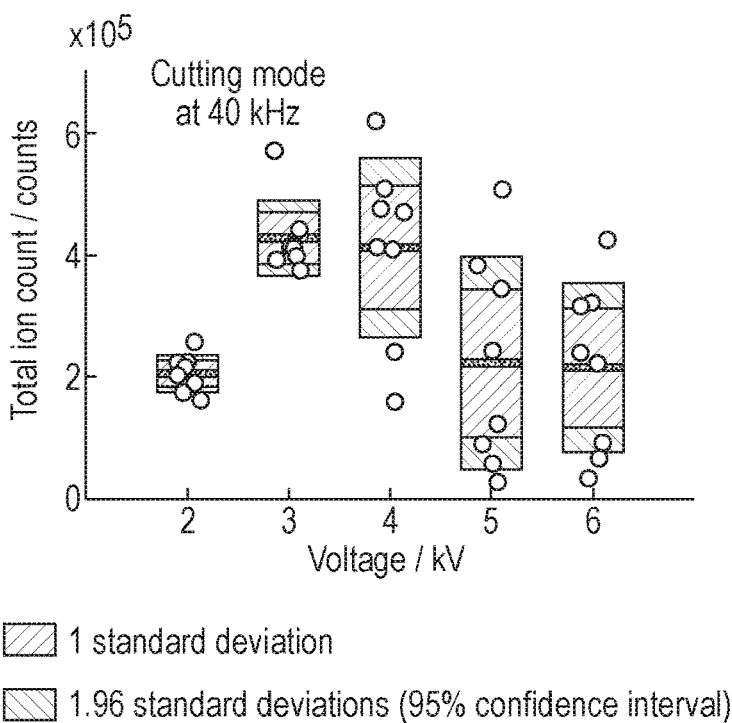
Figure 22A:
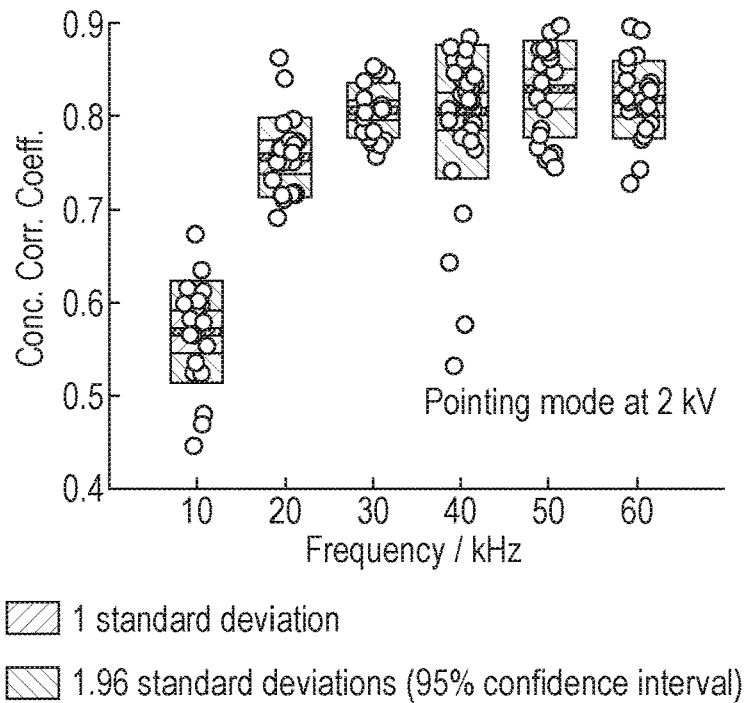
FIG. 22A shows concordance correlation coefficients between rapid evaporative ionization mass spectrometry imaging in a pointing mode of operation and iKnife technology mass spectra in dependency on frequency.
Figure 22B:
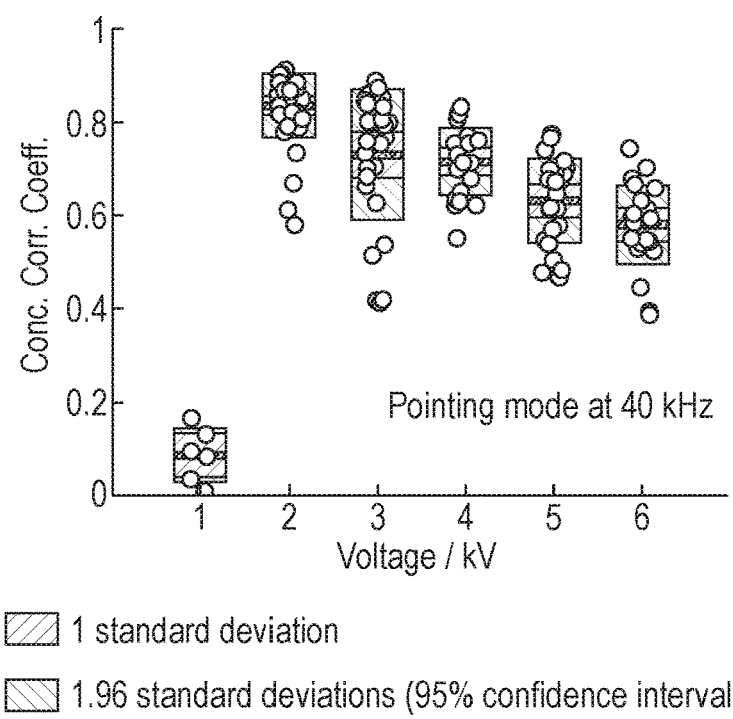
FIG. 22B shows concordance correlation coefficients (CCC) between rapid evaporative ionization mass spectrometry imaging in a pointing mode of operation and iKnife technology mass spectra in dependency on voltage.
Figure 22C:
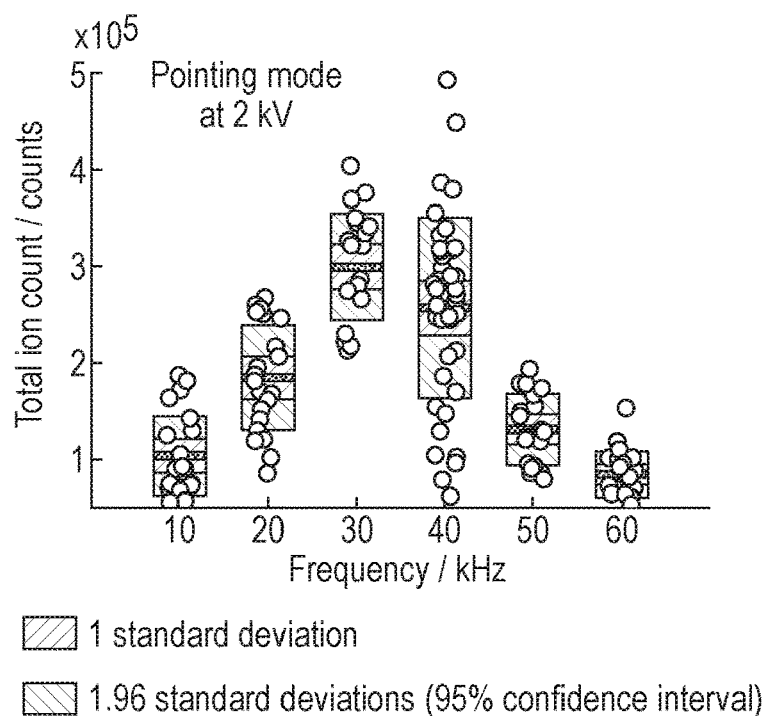
FIG. 22C shows total ion counts (TIC) at different frequencies in a pointing mode of operation and FIG. 22D shows total ion counts (TIC) at different voltages in a cutting mode of operation.
Figure 22D:
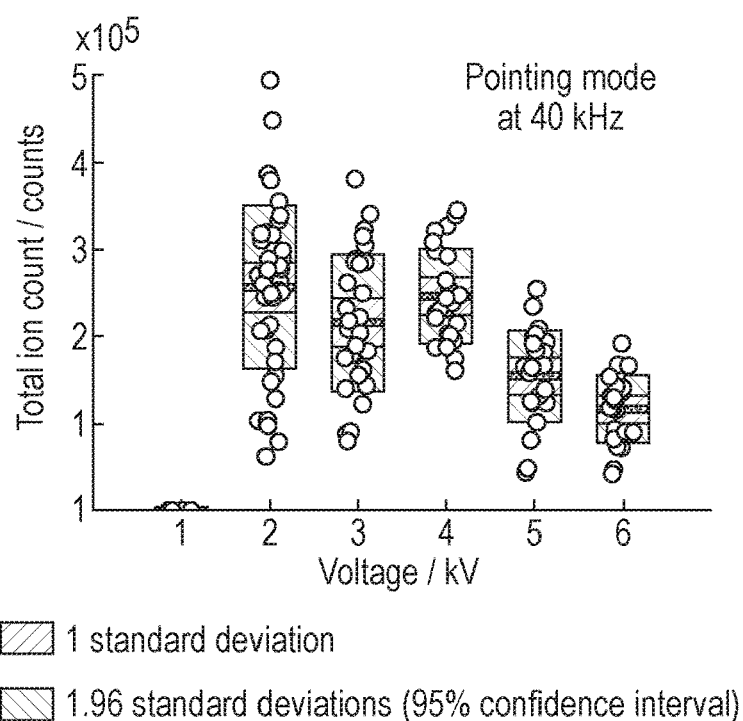

As shown in FIG. 20B, an increase in voltage at 40 kHz frequency resulted in similar phenomena as observed with decreasing frequency, such as carbonization and wide burning valleys, leading to high concordance correlation coefficients to be found at low voltages. However, once the voltage was set below about 2 kV, ion currents dramatically dropped (see the total ion counts in FIG. 21B). This led to an optimal parameter window between about 3-4 kV and about 40-50 kHz where concordance correlation coefficients are high and the total ion yield was also sufficient.

Similar behaviour was observed in a pointing mode of operation, as shown in the parameter optimization plots of FIGS. 22A-D which show the total ion counts and the concordance correlation coefficients between the rapid evaporative ionization mass spectrometry imaging and iKnife technology reference spectra at different operating frequencies and voltages. A difference between a pointing and a cutting mode of operation is the time the electrosurgical tip of the sampling probe 21 is in contact with the same part of tissue. In a cutting mode of operation, the tip is constantly moving and therefore continuously touches fresh tissue, whereas the tip remains at the same tissue spot for a defined amount of time in a pointing mode of operation. This leads to longer exposure of heat, thus voltage and frequency have to be chosen in a way that carbonization is kept at a minimum. At the same time, longer exposure also creates more ions, decreasing the need for higher voltages to gain a sufficiently high TIC. By decreasing the time the tip remained about 1 mm inside the sample to a value of about 0.1 s, the exposure could be successfully decreased so that burn crater diameter was about 500 µm while providing good TICs and concordance correlation coefficients at about 2 kV and about 40 kHz.

Figure 23A:
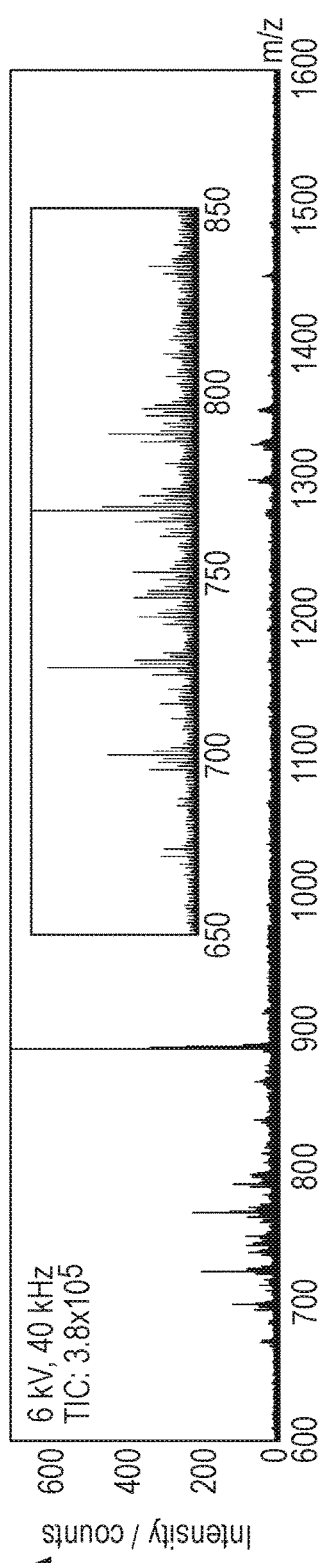
FIG. 23A shows a mass spectral pattern of porcine liver obtained in a cutting mode of operation for high voltages.
Figure 23B:
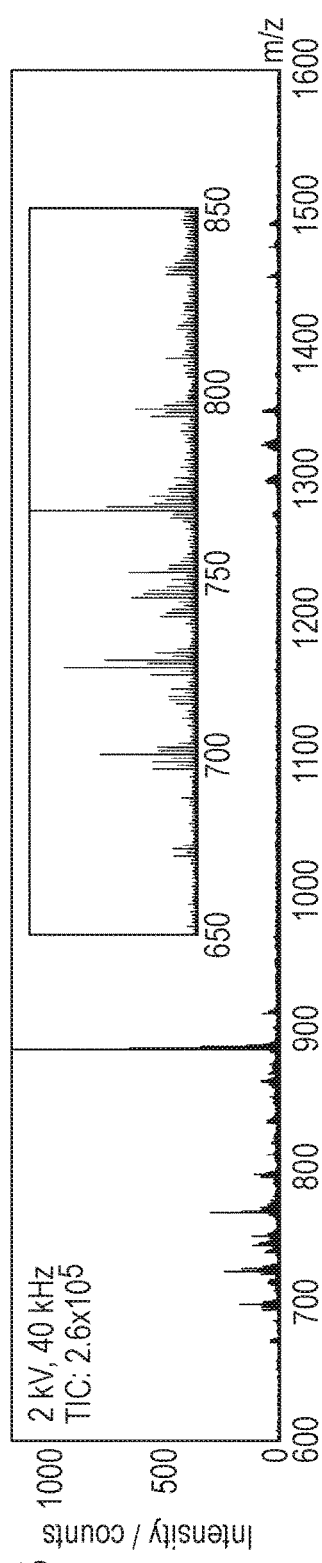
FIG. 23B shows a mass spectral pattern of porcine liver obtained in a cutting mode of operation for low voltages and FIG. 23C shows an iKnife technology reference spectrum.
Figure 23C:
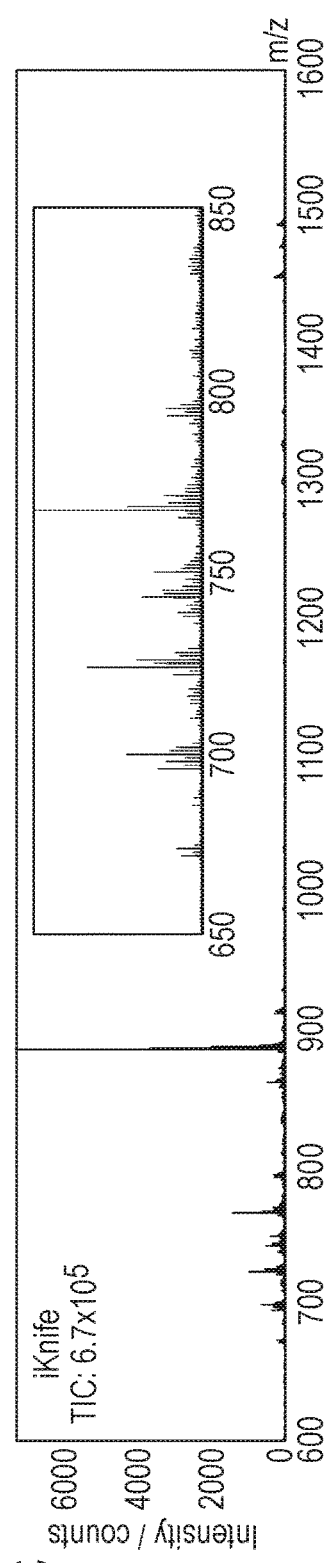

The impact of heat exposure on the mass spectral pattern is shown in FIGS. 23A-C. FIGS. 23A-C illustrate changes in mass spectral patterns of porcine liver obtained in cutting mode for high (FIG. 23A) and low (FIG. 23B) voltages compared to an iKnife technology reference spectrum (FIG. 23C). There is a prominent peak in all mass spectra at m/z=885.5 which is identified as a phosphatidyl-inositol species [PI(38:4)-H]$^-$.

The iKnife technology reference mass spectrum shown in FIG. 23C shows the highest TIC together with the most distinct intensity difference between the PI peak and all other phospholipid signals. The signal to noise ratio decreases with increasing voltage, which particularly impacts the spectral pattern in the mass range between about m/z 600 and 1000, used for classification. Although the intensity difference between the PI peak and all other peaks is larger for the 2 kV (FIG. 23B) compared to the 6 kV spectrum (FIG. 23A), the TIC of the 2 kV spectrum is lower, indicating a lower level of chemical noise.

Figure 24:
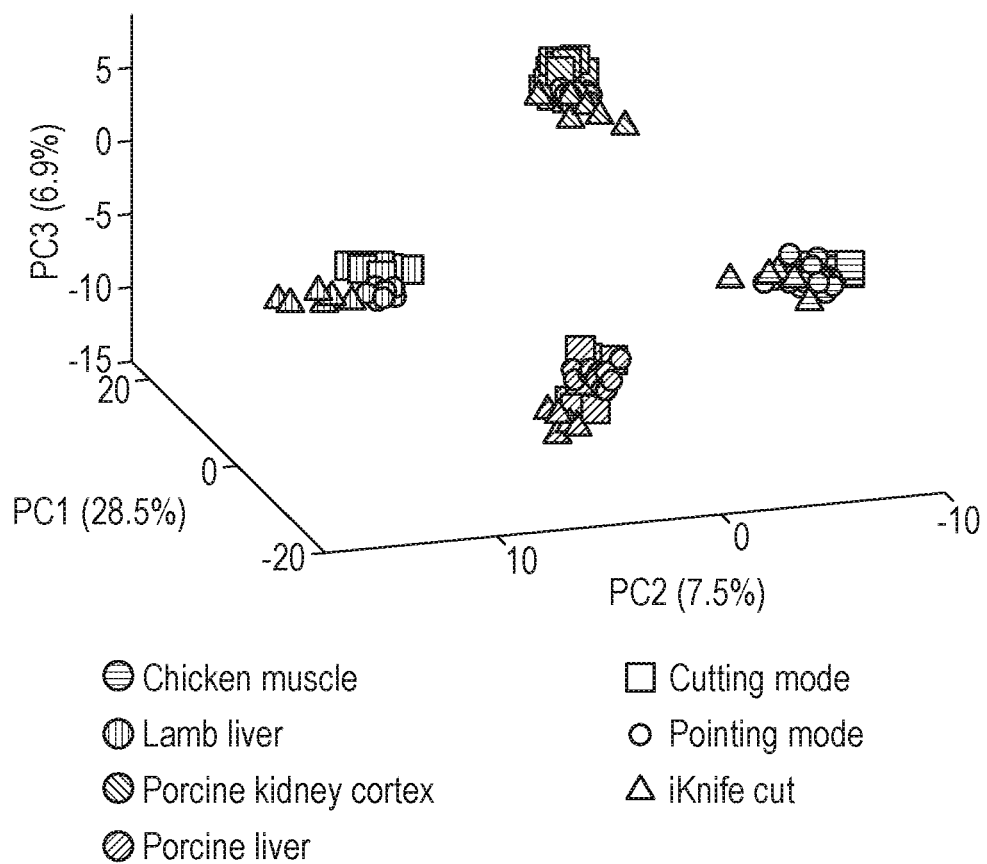
FIG. 24 shows a principal component analysis plot of various kinds of tissue types analysed with the same experimental rapid evaporative ionization mass spectrometry imaging parameters for cutting and pointing modes respectively.

Optimized cutting and pointing mode parameters were used to analyse various types of tissues from different animals, including porcine and lamb liver, porcine kidney cortex and chicken skeletal muscle. Additionally, all samples were analysed by proper electrosurgical equipment ('iKnife' technology setup) to ensure selected experimental rapid evaporative ionization mass spectrometry imaging parameters are suitable for multiple tissue types. Principal component analysis of the data showed that the overall variance is mostly associated with the tissue types, not the modes of analysis (see FIG. 24). This demonstrates that the experimental parameters are universally applicable to various tissue types in terms of matching the iKnife technology reference mass spectral patterns.

Imaging Liver with Metastatic Tumour

Figure 25:
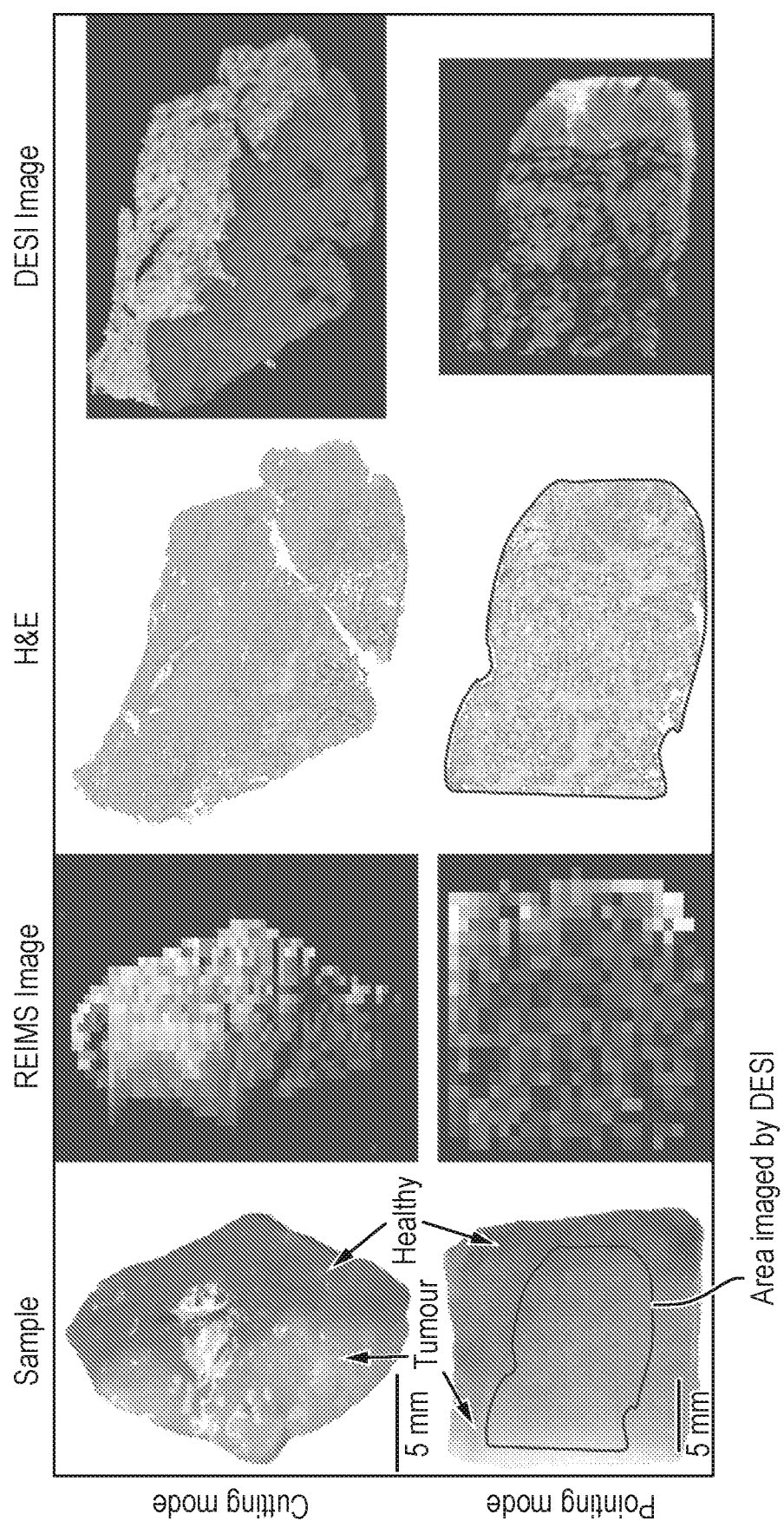
FIG. 25 shows a sample, H&E and mass spectrometric multivariate images of liver samples with metastatic tumour analysed by rapid evaporative ionization mass spectrometry and Desorption Electrospray Ionisation ("DESI") wherein it is apparent that both techniques clearly differentiate the tissue types.

The imaging capability of the novel rapid evaporative ionization mass spectrometry platform (i.e. ion imager) was studied using human liver tumour samples (as illustrated in FIG. 25). For demonstration of the versatility of the platform a cutting mode rapid evaporative ionization mass spectrometry image was obtained on a first instrument whilst a pointing mode image was obtained on a Time of Flight mass spectrometer. Spatially resolved mass spectrometric information was co-registered with H&E images to locate mass spectra with the desired histological identity. Supervised multivariate analysis of the tissues revealed clear distinction between healthy and cancerous tissue for both rapid evaporative ionization mass spectrometry imaging and Desorption Electrospray Ionization ("DESI") imaging data.

The Desorption Electrospray Ionization ("DESI") images show a sharp border between the two tissue types as a result of the high spatial resolution and small pixel size of 100 µm. The upper half of the cutting mode rapid evaporative ionization mass spectrometry image contains pixels of mixed healthy and tumour pattern influences causing a blurred border. A possible explanation is due to the direction of the rapid evaporative ionization mass spectrometry cut that was performed which started at healthy tissue and continued towards the tumour region. This might have caused transport of tumour tissue pieces into the healthy area. Another reason may be inhomogeneous tissue below the surface of the seemingly cancerous area.

Assuming that the mass spectra are to be used as reference data for the iKnife technology, then only pixels with a high class-membership probability should be used for training the multivariate models (i.e. the sample classification model).

Figure 26:
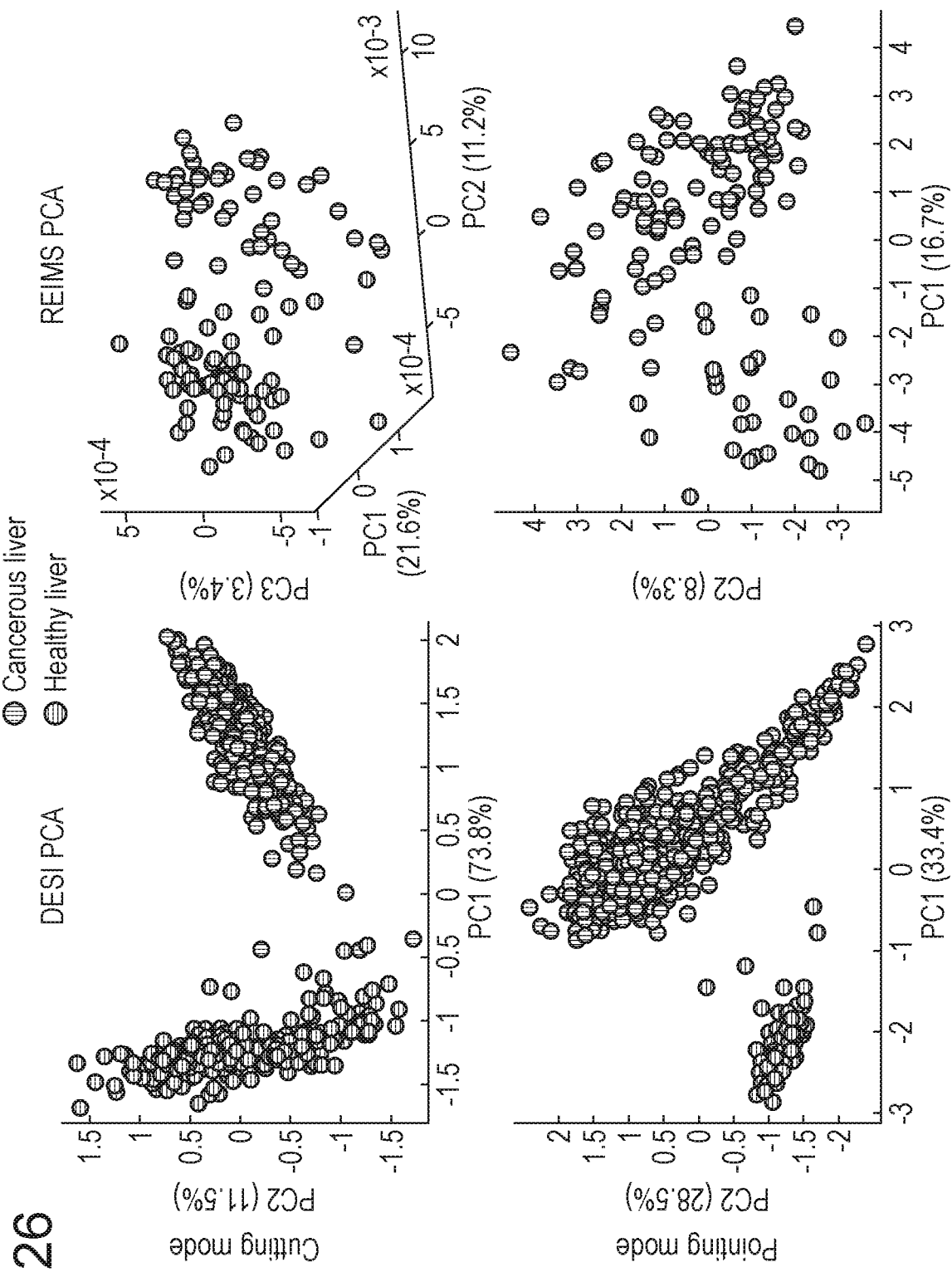
FIG. 26 shows principal component analysis plots of healthy and cancerous liver tissues for rapid evaporative ionization mass spectrometry imaging cutting and pointing modes as well as for Desorption Electrospray Ionisation ("DESI") data wherein PC is the principal component and percentage values are explained variance.

Unsupervised principal component analysis (PCA) demonstrates high intra-tissue-type spectral similarity together with spatially distinct clustering of healthy and cancerous data points in PCA space (see FIG. 26).

Desorption Electrospray Ionization ("DESI") imaging data acquired at high spatial resolution can also be used to locate histological fine structures and their corresponding mass spectra which can then be co-registered with the rapid evaporative ionization mass spectrometry data. A limiting factor for co-registration of Desorption Electrospray Ionization ("DESI") and rapid evaporative ionization mass spectrometry data is the spatial resolution currently achievable with the preferred rapid evaporative ionization mass spectrometry platform. While the cutting mode image was recorded at 500 µm pixel size, the pointing mode image features 750 µm sized pixels. In the case of this liver metastasis sample, the resolution is sufficient. However, in case of tissues with higher heterogeneity, higher spatial resolution images may be advantageous. The spatial resolution may be increased to decrease the diameter of the electrosurgical tip of the sampling probe 21 which would also be accompanied by lower spectral intensities. However, by connecting the sampling probe directly to the mass spectrometer inlet capillary (as is also done in the bipolar forceps approach described above) ion yield improves, thus overcoming the possible sensitivity issue. This also allows less penetration in z-direction, decreasing the probability of ionizing unanticipated tissue types.

Multivariate analysis of the liver metastasis samples shows a clear distinction of tissue types based on their molecular ion patterns. While rapid evaporative ionization mass spectrometry and Desorption Electrospray Ionization ("DESI") exhibit different ionization mechanisms resulting in mass spectrometric patterns that are not directly comparable to each other, univariate biochemical comparison of single ions provides a comparable measure for Desorption Electrospray Ionization ("DESI") and rapid evaporative ionization mass spectrometry co-registration. For certain compounds, the relative intensity difference between two tissue types is similar across all tissue types, ionization techniques and rapid evaporative ionization mass spectrometry analysis modes (cutting and pointing modes). This enables Desorption Electrospray Ionization ("DESI") to be used as a fold-change intensity-predictor for rapid evaporative ionization mass spectrometry based on up- and down-regulated compounds, which ultimately represents additional information for unknown tissue type identification. The higher spatial resolution of Desorption Electrospray Ionization ("DESI") allows the up- and down-regulated ions to be registered with certain histological features which may not be resolvable by rapid evaporative ionization mass spectrometry. This gives insight to the underlying histological composition of a tissue if certain changes in single ion intensities are observed in low resolution rapid evaporative ionization mass spectrometry.

Figure 27:
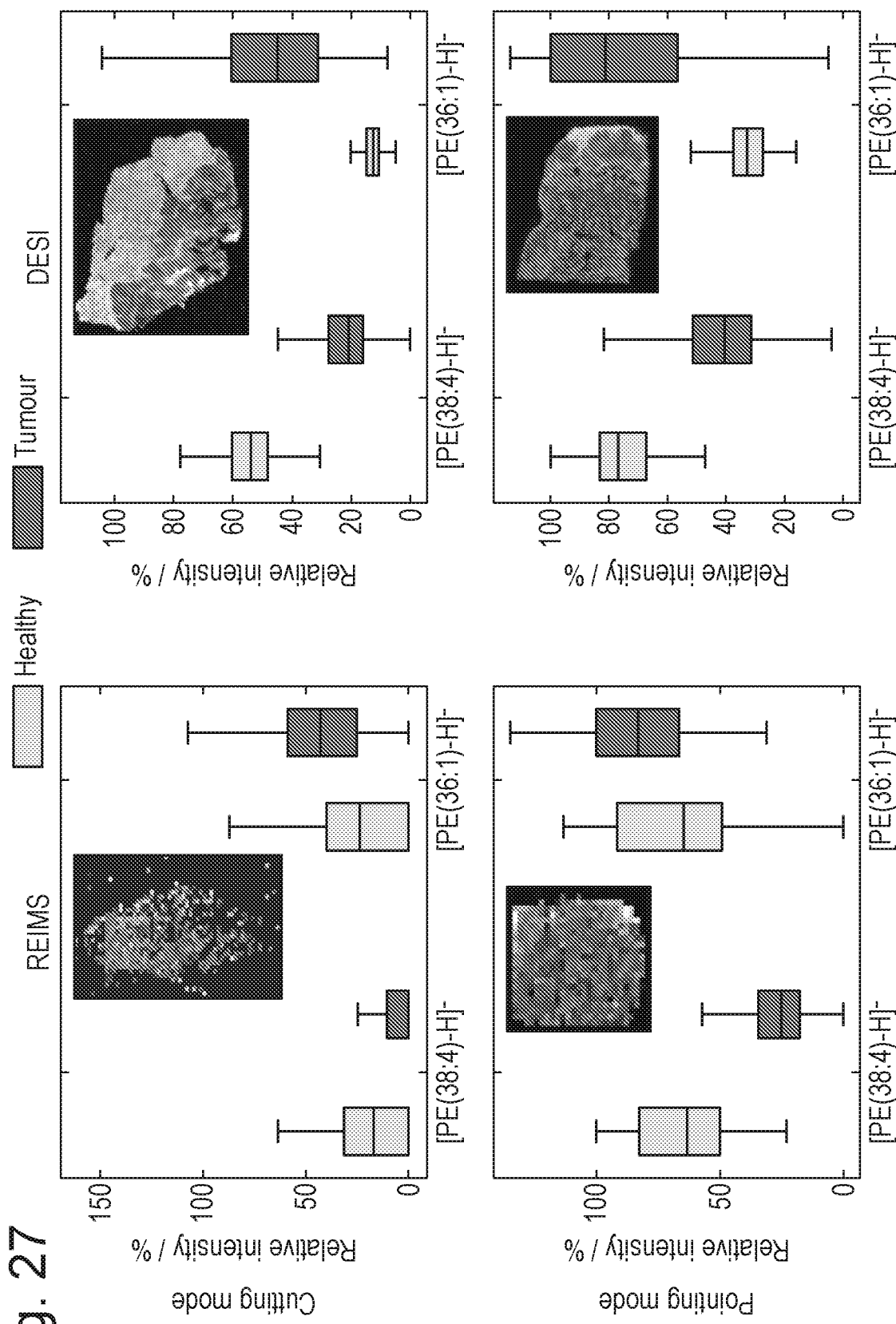
FIG. 27 shows an univariate intensity comparison of single phospholipid ion species wherein the depicted images of samples are ion-images of the respective ions and Desorption Electrospray Ionisation ("DESI") and rapid evaporative ionization mass spectrometry show similar relative intensity values for the same ions wherein PE is phosphatidyl-ethanolamine.

In the case of metastatic liver comparison, two different phosphatidyl-ethanolamine (PE) species were found to possess opposite relative intensities between healthy and metastatic tissue types as shown in FIG. 27. The represented images are ion images of the two PE ion species. PE(38:4) has a higher abundance in healthy tissue in all four cases, with the rapid evaporative ionization mass spectrometry cutting mode image showing barely any presence of this ion in tumour tissue. However, compared to the Desorption Electrospray Ionization ("DESI") images where this lipid is well abundant even in tumour tissue, the absence of intensity has to be associated with the lower sensitivity achieved by rapid evaporative ionization mass spectrometry cutting. Opposite behaviour is seen by the ion [PE(36:1)-H]$^-$ showing elevated intensities in tumour tissue.

Future research will be dedicated to the comparison of multiple samples to obtain cross-validated relative intensity levels for ions of interest. Once enough data is collected, Desorption Electrospray Ionization ("DESI") can serve as a biochemical blueprint, allowing tissue types to be histologically annotated with higher confidence when analysed by rapid evaporative ionization mass spectrometry.

The ion imager may include a monopolar device with a separate return electrode or a bipolar device. Other embodiments are also contemplated in which the ion imager may include a multi-phase or 3-phase device and may include, for example, three or more separate electrodes or probes.

Setting Up High Throughput Culturing, DNA Isolation and MS Data Acquisition, Determination of Minimum Culturing Time A customised Tecan EVO® platform incorporating automated colony imaging and colony picking was used to provide a reproducible system for high throughput workflows utilising rapid evaporative ionization mass spectrometry analysis. Using an automated platform helps minimise user time and errors to ensure the data is accurate and reproducible.

Automated rapid evaporative ionization mass spectrometry analysis was compared to the spectral profiles obtained using forceps. Five isolates of thirty species were examined using both methods and were also tested with and without the introduction of isopropanol ("IPA") matrix.

According to various embodiments a matrix (IPA) may added to the aerosol, smoke or vapour generated by the first device. The matrix may be added to the aerosol, smoke or vapour prior to the aerosol, smoke or vapour impacting upon a collision surface.

Figure 28:
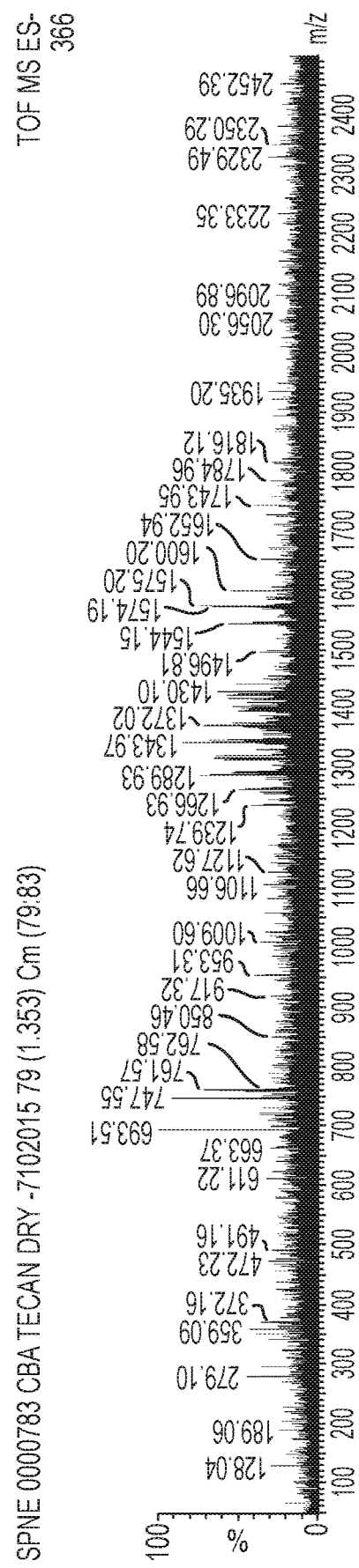
FIG. 28 shows an example profile for *S. pneumoniae* acquired using a modified Tecan EVO® without the introduction of isopropanol (IPA) matrix.

It was apparent that for some bacterial species the Tecan® method generated noisy spectra. For example, *Streptococcus pneumoniae* generally produced noisy spectra with low intensities (see FIG. 28). Although some lipids could be observed, this was not reproducible.

Figure 29A:
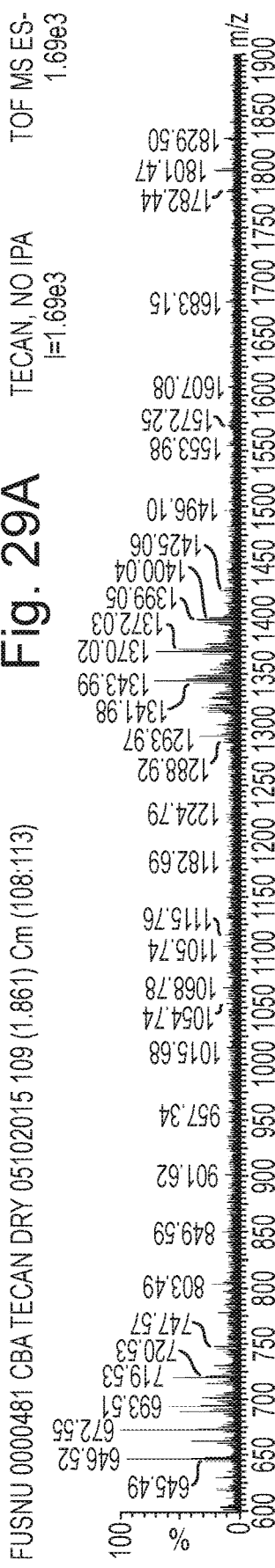
FIG. 29A shows spectral profiles obtained for *Fusobacterium nucleatum* using the Tecan platform without IPA.
Figure 29B:
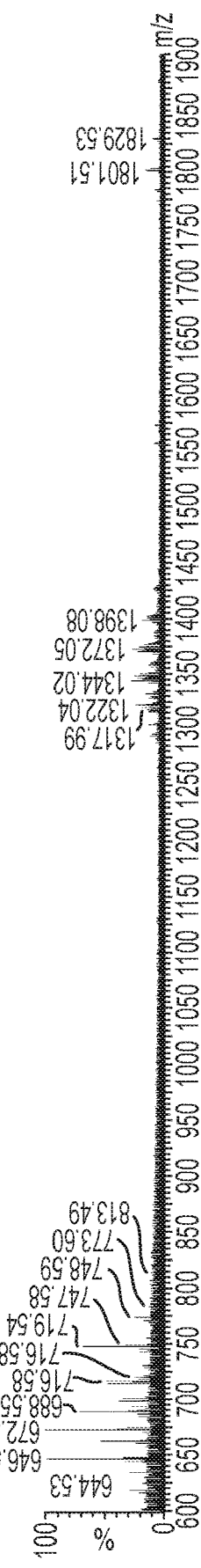
FIG. 29B shows spectral profiles obtained for *Fusobacterium nucleatum* using forceps without IPA and FIG. 29C shows spectral profiles obtained for *Fusobacterium nucleatum* using forceps with IPA.
Figure 29C:
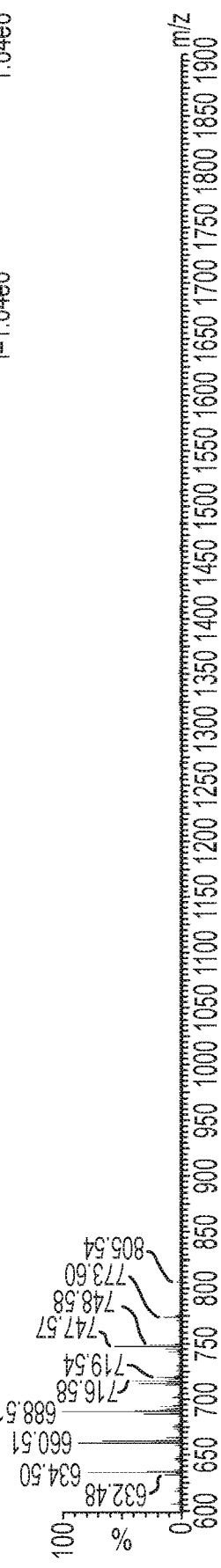

Spectral profiles including both high and low mass lipids were observed for *Fusobacterium nucleatum*, but typically the profiles lacked those within higher mass ranges as in the mass spectrum shown in FIG. 29C. However, as shown by the spectra in FIG. 29A and FIG. 29B, these higher mass components were sometimes apparent and thus it is clear that, with optimisation, good quality spectra may be acquired.

Although a thorough analysis of each species needs to be performed, it was clear that the Tecan® produced data that encompasses higher mass range lipids. For example, as shown in FIGS. 30A-D automated rapid evaporative ionization mass spectrometry produced a higher signal to noise ratio for *Staphylococcus hominis*.

Figure 30A:
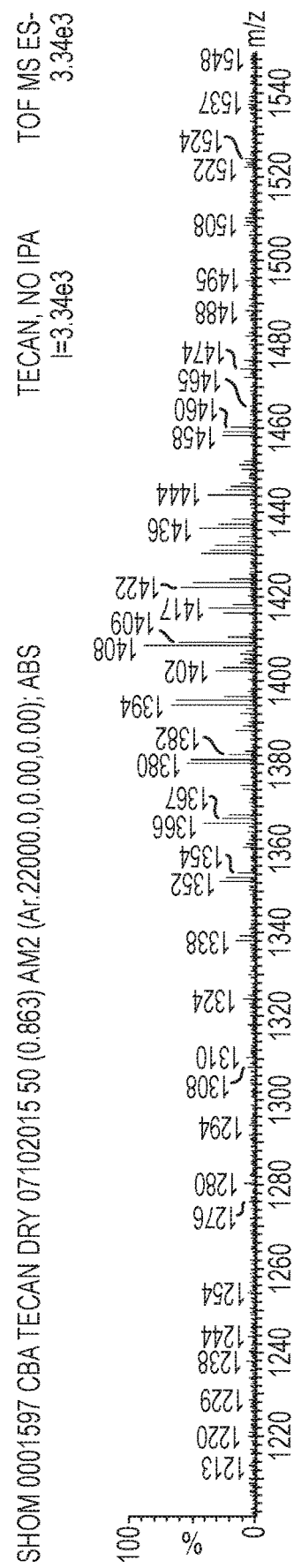
FIG. 30A shows spectral profiles obtained for *Staphylococcus hominis* using automated Tecan based rapid evaporative ionization mass spectrometry without IPA.
Figure 30B:
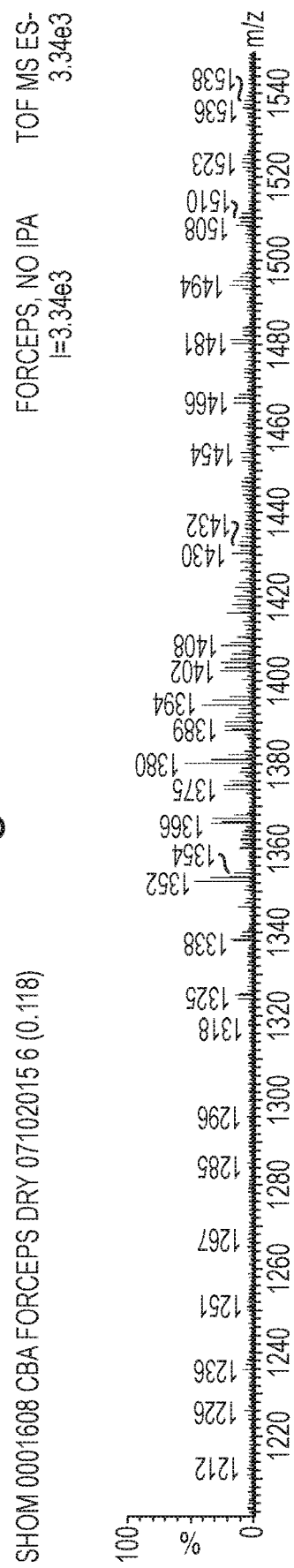
FIG. 30B shows spectral profiles obtained for *Staphylococcus hominis* using forceps based rapid evaporative ionization mass spectrometry without IPA.
Figure 30C:
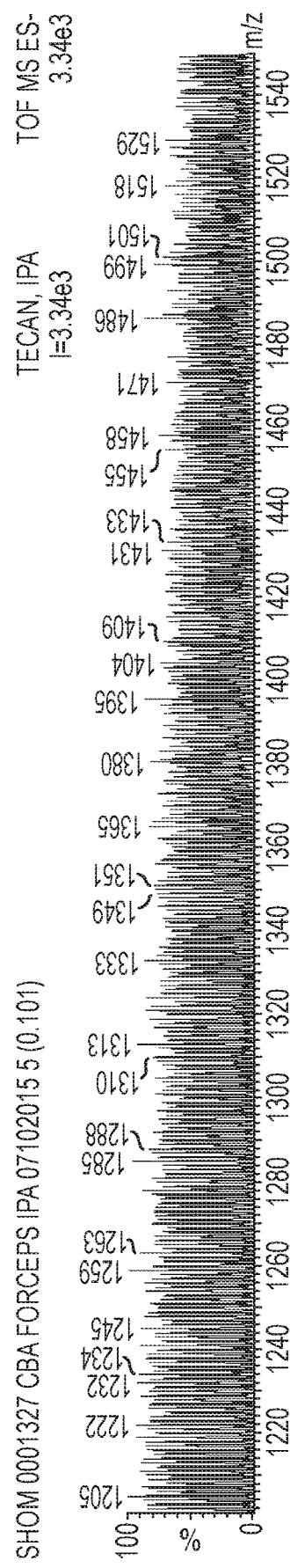
FIG. 30C shows spectral profiles obtained for *Staphylococcus hominis* using automated Tecan based rapid evaporative ionization mass spectrometry with IPA and FIG. 30D shows spectral profiles obtained for *Staphylococcus hominis* using forceps based rapid evaporative ionization mass spectrometry with IPA.
Figure 30D:
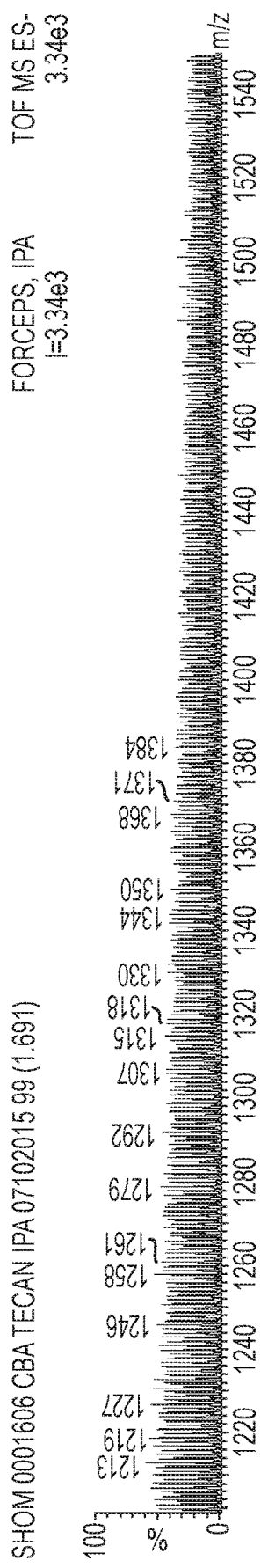

The infusion of IPA, although producing peaks of significantly higher intensities, may result in the loss of higher mass range lipids as shown by the mass spectra in FIG. 30C and FIG. 30D in the case of *S. hominis* and FIGS. 31A-B in the case of *Pseudomonas aeruginosa*. The presence of IPA also seems to increase the quality and reproducibility of the analysis. The statistical differentiation of strains appears to be equally efficient with and without IPA. Nevertheless, the high mass ranges seem to contribute to the separation of the strains in the dry mode, suggesting that, without being required for the separation, they might still bear valuable information.

It is also envisioned that a high-throughput sequencing pipeline may be implemented to attach the 'Gold' standard of taxonomic classification (16S rRNA gene sequence for bacteria and ITS region sequence for fungi) to each isolate rapid evaporative ionization mass spectrometry fingerprint. For instance, a filtration based platform such as the QIAGEN QlAcube that can process 96 isolates may be adapted to encompass the breath of clinical microbiology. Various different automated capillary electrophoresis technologies may be used to ensure PCR have successfully been generated. It is also contemplated that agarose gel electrophoresis may be used. A bioinformatic pipeline may be developed to allow for the automated analysis of sequence data and taxonomic classification against established sequence databases.

Many of the techniques described above are presented in the context of utilising rapid evaporative ionization mass spectrometry as an ionisation method. However, it will be appreciated that the techniques and apparatus described herein are not limited to rapid evaporative ionization mass spectrometry devices and may also be extended to other ambient ion sources and other methods of ambient ionisation. For example, a tool having fenestrations or aspiration ports may be provided as part of a laser surgery probe for aspirating aerosol, smoke or vapour generated using the laser. Further details of known ambient ion sources that may be suitable for use with the techniques and apparatus described herein are presented above.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue.

Various surgical, therapeutic, medical treatment and diagnostic methods are contemplated.

However, other embodiments are contemplated which relate to non-surgical and non-therapeutic methods of mass spectrometry and/or ion mobility spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

Although the present invention has been described with reference to preferred embodiments, it will be understood by those skilled in the art that various changes in form and detail may be made without departing from the scope of the invention as set forth in the accompanying claims.

The invention claimed is:

1. A method of ion imaging comprising:
automatically sampling a plurality of different locations on a sample using a laser device arranged and adapted to generate aerosol, smoke or vapour from the sample;
automatically translating said sample relative to said laser device before and/or during and/or after obtaining mass spectral data and/or ion mobility data from at least some of said locations on said sample;
providing a collision surf surface located within a vacuum chamber of a mass spectrometer and/or ion mobility spectrometer so as to generate analyte ions;
adding a matrix to said aerosol, smoke or vapour generated by said laser device to form a mixture of said aerosol, smoke or vapour and said matrix prior to said aerosol, smoke or vapour impacting upon said collision surface;
passing said mixture of said aerosol, smoke or vapour and said matrix into the vacuum chamber of the mass spectrometer and/or ion mobility spectrometer;
causing at least some of said mixture of said aerosol, smoke or vapour and said matrix to impact upon said collision surface wherein at least some of said aerosol, smoke or vapour is ionized upon impacting said collision surface so as to generate analyte ions;
obtaining mass spectral data and/or ion mobility data corresponding to each said location; and
using said obtained mass spectral data and/or ion mobility data to construct, train or improve a sample classification model;
wherein said matrix comprises isopropanol.

2. The method as claimed in claim 1, wherein said sample comprises a biological sample, biological tissue, human tissue, animal tissue, biological matter, a bacterial colony, a fungal colony or one or more bacterial strains.

3. The method as claimed in claim 1, wherein said sample comprises native or unmodified sample material, optionally wherein said native or unmodified sample material is unmodified by the addition of a matrix or reagent.

4. The method as claimed in claim 1, wherein said sample classification model comprises a biological sample classification model, a biological tissue classification model, a human tissue classification model, an animal tissue classification model or a bacterial strain classification model.

5. The method as claimed in claim 1, further comprising constructing, training or improving said sample classification model in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of sample material; (v) to determine whether or not one or more desired or undesired substances are present in said sample; (vi) to confirm the identity or authenticity of said sample; (vii) to determine whether or not one or more impurities, illegal substances or undesired substances are present in said sample; (viii) to determine whether a human or animal patient is at an increased risk of suffering an adverse outcome; (ix) to make or assist in the making a diagnosis or prognosis; and (x) to inform a surgeon, nurse, medic or robot of a medical, surgical or diagnostic outcome.

6. The method as claimed in claim 1, wherein the step of using said obtained mass spectral data and/or ion mobility data to construct, train or improve said sample classification model comprises performing a supervised or unsupervised multivariate statistical analysis of said mass spectral data and/or ion mobility data, optionally wherein said multivariate statistical analysis is selected from the group consisting of: (i) principal component analysis ("PCA"); and (ii) linear discriminant analysis ("LDA").

7. The method as claimed in claim 1, further comprising heating said collision surface optionally to a temperature selected from the group consisting of: (i) 200-300° C.; (ii) 300-400° C.; (iii) 400-500° C.; (iv) 500-600° C.; (v) 600-700° C.; (vi) 700-800° C.; (vii) 800-900° C.; (viii) 900-1000° C.; (ix) 1000-1100° C.; and (x) >1100° C.

8. A mass spectrometer and/or ion mobility spectrometer comprising:
a laser device arranged and adapted to generate aerosol, smoke or vapour from a sample;
a device arranged and adapted to automatically translate said sample relative to said laser device any one or more of before, during, and after obtaining mass spectral data and/or ion mobility data from at least some of said locations on said sample;
a device arranged and adapted to add a matrix to said aerosol, smoke or vapour generated by said laser device to form a mixture of said aerosol, smoke or vapour and said matrix;
a collision surface located within a vacuum chamber of a mass spectrometer and/or ion mobility spectrometer wherein in use at least some of said mixture of said aerosol, smoke or vapour and said matrix is caused to impact upon said collision surface and at least some of said aerosol, smoke or vapour is ionized upon impacting said collision surface so as to generate analyte ions; and
a control system arranged and adapted:
(i) to automatically sample a plurality of different locations on said sample using said first laser device and to obtain mass spectral data and/or ion mobility data corresponding to each said location; and
(ii) to use said obtained mass spectral data and/or ion mobility data to construct, train or improve a sample classification model;
wherein said matrix comprises isopropanol.

9. The mass spectrometer and/or ion mobility spectrometer as claimed in claim 8, wherein said sample comprises a biological sample, biological tissue, human tissue, animal tissue, biological matter, a bacterial colony, a fungal colony or one or more bacterial strains.

10. The mass spectrometer and/or ion mobility spectrometer as claimed in claim 8, wherein said sample classification model comprises a biological sample classification model, a biological tissue classification model, a human tissue classification model, an animal tissue classification model or a bacterial strain classification model.

11. The mass spectrometer and/or ion mobility spectrometer as claimed in claim 8, further comprising a heater which is optionally arranged and adapted to heat said collision surface to a temperature selected from the group consisting of: (i) 200-300° C.; (ii) 300-400° C.; (iii) 400-500° C.; (iv) 500-600° C.; (v) 600-700° C.; (vi) 700-800° C.; (vii) 800-900° C.; (viii) 900-1000° C.; (ix) 1000-1100° C.; and (x) >1100° C.

* * * * *